(12) United States Patent
Tokida et al.

(10) Patent No.: US 8,003,346 B2
(45) Date of Patent: Aug. 23, 2011

(54) MUTANT PCNA

(75) Inventors: Tadaaki Tokida, Chiba (JP); Satoshi Hihara, Chiba (JP); Takashi Kudou, Chiba (JP); Akira Kawamura, Chiba (JP); Hirofumi Doi, Chiba (JP); Yoshizumi Ishino, Fukuoka (JP)

(73) Assignee: Celestar Lexico-Sciences, Inc., Chiba (JP)

( * ) Notice: Subject to any disclaimer, the term of this patent is extended or adjusted under 35 U.S.C. 154(b) by 555 days.

(21) Appl. No.: 11/994,437

(22) PCT Filed: Jul. 4, 2006
(Under 37 CFR 1.47)

(86) PCT No.: PCT/JP2006/313337
§ 371 (c)(1),
(2), (4) Date: Sep. 2, 2008

(87) PCT Pub. No.: WO2007/004654
PCT Pub. Date: Jan. 11, 2007

(65) Prior Publication Data
US 2009/0209003 A1     Aug. 20, 2009

(30) Foreign Application Priority Data
Jul. 4, 2005   (JP) ................. 2005-195530

(51) Int. Cl.
*G01N 33/52* (2006.01)
*C07H 17/00* (2006.01)
*C07K 14/00* (2006.01)

(52) U.S. Cl. ............. 435/69.1; 435/320.1; 435/325; 435/253.2; 536/23.1; 530/350

(58) Field of Classification Search .......... None
See application file for complete search history.

(56) References Cited

U.S. PATENT DOCUMENTS

| | | | |
|---|---|---|---|
| 5,338,671 A | 8/1994 | Scalice et al. | |
| 5,436,149 A | 7/1995 | Barnes | |
| 6,218,150 B1 * | 4/2001 | Uemori et al. | 435/91.1 |
| 7,384,739 B2 * | 6/2008 | Kitabayashi et al. | 435/6 |
| 2005/0003401 A1 | 1/2005 | Hogrefe et al. | |

FOREIGN PATENT DOCUMENTS

| | | |
|---|---|---|
| JP | 2002-360261 | 12/2002 |
| JP | 2003-506048 | 2/2003 |

OTHER PUBLICATIONS

Randall K. Saiki et al., "Primer-Directed Enzymatic Amplification of DNA with a Thermostable DNA Polymerase", Science, vol. 239, Jan. 29, 1988, pp. 487-491.
Janice Cline et al., "PCR fidelity of *Pfu* DNA polymerase and other thermostable DNA polymerases", Nucleic Acids Research, 1996, vol. 24, No. 18, 3546-3551.
Shou Waga et al., "The DNA Replication Fork in Eukaryotic Cells", Annu. Rev. Biochem. 1998, 67, 721-751.
Arthur Kornberg, "Minireview: DNA Replication", The Journal of Biological Chemistry, vol. 263, No. 1, Issue of Jan. 8, 1988, pp. 1-4.
Isaac K. O. Cann et al., "Functional Interactions of a Homolog of Proliferating Cell Nuclear Antigen with DNA Polymerases in *Archaea*", Journal of Bacteriology, Nov. 1999, vol. 181, No. 21, pp. 6591-6599.
Wayne M. Barnes, "PCR amplification of up to 35-kb DNA with high fidelity and high yield from λ bacteriophage templates", Proc. Natl. Acad. Sci, USA, vol. 91, pp. 2216-2220, Mar. 1994, pp. 2216-2220.
Isaac K. O. Cann et al., "Biochemical Analysis of Replication Factor C from the Hyperthermophilic Achaeon *Pyrococcus furiosus*", Journal of Bacteriology, Apr. 2001, vol. 183, No. 8, pp. 2614-2623.
Masahiro Takagi et al., "Characterization of DNA Polymerase from *Pyrococcus* sp. Strain KOD1 and Its Application to PCR", Applied and Environmental Microbiology, Nov. 1997, vol. 63, No. 11, pp. 4504-4510.
Shigeki Matsumiya et al., "Intermolecular ion pairs maintain the toroidal structure of *Pyrococcus funosus* PCNA", Protein Science (2003), 12:823-831.
Shigeki Matsumiya et al., "Crystal structure of an archaeal DNA sliding clamp: Proliferating cell nuclear antigen from *Pyrococcus furiosus*", Protein Science (2001), 10:17-23.
Masao Kitabayashi et al., "Gene Cloning and Polymerase Chain Reaction with Proliferating Cell Nuclear Antigen from *Thermococcus kodakaraensis*KOD1", Biosci. Biotechnol. Biochem. 66 (10), 2194-2200, 2002.
Masao Kitabayashi et al., "Gene Cloning and Function Analysis of Replication Factor C from *Thermococcus kodakaraensis* KOD1", Biosci. Biotechnol. Biochem., 67 (11), 2373-2380, 2003.
Tomoko Miyata et al., "The clamp-loading complex for processive DNA replication", Nature Structural and Molecular Biology, vol. 11, No. 7, Jul. 2004, pp. 632-636.
Stanislav N. Naryzhny et al., "Proliferating Cell Nuclear Antigen (PCNA) May Function as a Double Homotrimer Complex in the Mammalian Cell", The Journal of Biological Chemistry, vol. 280, No. 14, Issue of Apr. 8, pp. 13888-13894, 2005.
Hirokazu Nishida et al., "Identification of the critical region in Replication factor C from *Pyrococcus furiosus* for the stable complex formation with Proliferating cell nuclear antigen and DNA", Genes Genet. Syst. (2005) 80, pp. 83-93.
Yoshizumi Ishino et al., "Biochemical and three-dimensional structural analyses of PCNA-RFC-DNA complex", 2003, pp. 333(S1A-2).
Tomoko Miyata et al., "Open clamp structure in the clamp-loading complex visualized by electron microscopic image analysis", PNAS, Sep. 27, 2005, vol. 102, No. 39, 13795-13800.

* cited by examiner

*Primary Examiner* — Karen Carlson
(74) *Attorney, Agent, or Firm* — Stephen A. Bent; Foley & Lardner LLP

(57) ABSTRACT

The present invention is to construct a DNA replication reaction system which is excellent in versatility and is easily used. An amino acid sequence of a PCNA monomer which is one of factors involved in DNA replication is prepared so that amino acid residues causing mutual charge repulsion constitute a site which causes, when an N terminal region of the PCNA monomer and a C terminal region of another PCNA monomer act as an interface to form a multimeric complex, an intermolecular interaction of the monomers in an interface region of the monomers.

11 Claims, 43 Drawing Sheets

Gel: 10-20% Polyacrylamide.
Amount for application: set to 4 μg.
Electrophoresis was performed as to four samples each from a different purification lot Size marker available from BioRad was used Effect of addition of PCNA 13 on Pyrobest
--Amplification length (2 kb) and extension time--

| Extension Time (min) | 0.5 | | 1 | | 2 | |
|---|---|---|---|---|---|---|
| PCNA13 | - | + | - | + | - | + |

Marker; 5 μL of lambda/Sty I
Sample; 10 μL of 50 μL reaction liquid was subjected to electrophoresis Effect of addition of PCNA 13 on Pyrobest
--Amplification length (8.4 kb) and extension time--

Marker; 5 μL of lambda/Sty I
Sample; 10 μL of 50 μL reaction liquid was subjected to electrophoresis Effect of addition of PCNA 13 on Pyrobest
--Amplification length (15.8 kb) and extension time--

Marker; 5 μL of lambda/Sty I
Sample; 10 μL of 50 μL reaction liquid was subjected to electrophoresis Effect of addition of PCNA 13 on Extaq
--Amplification length (2 kb) and extension time--

Marker; 5 μL of lambda/Sty I
Sample; 10 μL of 50 μL reaction liquid was subjected to electrophoresis Effect of addition of PCNA 13 on Extaq
--Amplification length (8.4 kb) and extension time--

| Extension Time | 1.5 min | | 2 min | | 3 min | |
|---|---|---|---|---|---|---|
| PCNA13 | - | + | - | + | - | + |

Marker; 5 μL of lambda/Sty I
Sample; 10 μL of 50 μL reaction liquid was subjected to electrophoresis Effect of addition of PCNA 13 on Extaq
--Amplification length (15.8 kb) and extension time--

Marker; 5 μL of lambda/Sty I
Sample; 10 μL of 50 μL reaction liquid was subjected to electrophoresis Effect of addition of PCNA 13 on Vent DNA Polymerase
--Amplification length (2 kb) and extension time--

Marker; 5 μL of lambda/Sty I
Sample; 10 μL of 50 μL reaction liquid was subjected to electrophoresis Effect of addition of PCNA 13 on Vent DNA Polymerase
--Amplification length (8.4 kb) and extension time--

| Extension Time | 1 min | | 3 min | | 5 min | |
|---|---|---|---|---|---|---|
| PCNA13 | - | + | - | + | - | + |

Marker; 5 μL of lambda/Sty I
Sample; 10 μL of 50 μL reaction liquid was subjected to electrophoresis Effect of addition of PCNA 13 on Pfu Turbo DNA Polymerase

| Length | 2 kb | | 8.4 kb | | 15.8 kb | |
|---|---|---|---|---|---|---|
| PCNA13 | - | + | - | + | - | + |

Marker; 5 μL of lambda/Sty I
Sample; 10 μL of 50 μL reaction liquid was subjected to electrophoresis Marker; 5 μL of lambda/Sty I
Sample; 10 μL of 50 μL reaction liquid was subjected to electrophoresis Effect of addition of PCNA 13 on Pwo DNA Polymerase

| | 2 kb | | | | 8.4 kb | | | |
|---|---|---|---|---|---|---|---|---|
| Extension Time | 30 sec | | 1 min | | 2 min | | 4 min | |
| PCNA13 | − | + | − | + | − | + | − | + |

Marker; 5 μL of lambda/Sty I
Sample; 10 μL of 50 μL reaction liquid was subjected to electrophoresis M: Size marker from NEB
1: KOD-PCNA01
2: KOD-PCNA13

Gel: 10-20% Polyacrylamide
Amount for application: set to 4 μg

| M | lambda/ Sty I marker |
|---|---|
| 1 | No KOD-PCNA nor KOD RFC |
| 2 | KOD-PCNA01 (0.6 ng/μL) |
| 3 | KOD-PCNA01 (0.6 ng/μL)+ KOD-RFC (4 ng/μL) |
| 4 | KOD-PCNA01 (0.6 ng/μL)+ KOD-RFC (8 ng/μL) |
| 5 | KOD-PCNA13 (0.6 ng/μL) |
| 6 | KOD-PCNA13 (0.6 ng/μL)+ KOD-RFC(4 ng/μL) |
| 7 | KOD-PCNA13 (0.6 ng/μL)+ KOD-RFC (8 ng/μL) |

Effect of addition of a variety of PCNA mutants and RFC on Pyrobest --(8.4 kbp)--

MUTANT PCNA

TECHNICAL FIELD

The present invention relates to a DNA replication factor, and more particularly relates to a proliferating cell nuclear antigen (PCNA) which has excellent function to assist DNA replication.

BACKGROUND ART

Gene amplification technology and PCR method

A technology to amplify nucleic acids such as DNA and RNA has been widely disseminated in both basic research and industrial application along with development of gene engineering technology. At an early stage, in order to obtain a particular target nucleic acid sequence, the sequence were in general prepared by cutting out the necessary sequence with restriction enzymes from nucleic acids amplified in yeast or *Escherichia coli* cells. Subsequently, it became possible to amplify a target particular nucleic acid region in vitro by the development of PCR by Mullis et al and dissemination thereof. For the PCR method, various experimental and industrial applications have been developed in parallel with active commercialization and distribution of specific apparatuses and related reagents. Thus the PCR method became the substantial standard method for amplifying the gene. As the research for the DNA replication has advanced, various technologies whose principals are different from that of PCR have been designed and developed, but they are less common in terms of operationality, cost and quality, and no technology which sweeps aside the PCR method has appeared.

Points for Evaluating PCR Method

The principle of the PCR method is thought to be based on minimally mimicking the intracellular DNA replication. That is, the principle is based on (1) dissociation of a target nucleic acid template by thermal denaturation, (2) pairing of the target sequence with a pair of complementary primers and (3) extension of the primer complementary to the template by DNA polymerase. The objective nucleic acid sequence is exponentially amplified by repeating these reactions continuously. In a general protocol of PCR, several kb of the target sequence in the template in nano gram order is often amplified to obtain a product in μg order by the reaction for about two hours.

The PCR method has technical restrictions, which representatively include the following 4 points: (1) fidelity to the template (performance to amplify the sequence precisely corresponding to the template), (2) extendibility (performance to amplify the longer sequence), (3) efficiency to amplify the target sequence, and (4) reaction specificity. These are also often addressed as the points which evaluate PCR. Reagents and kits for PCR have been being developed for the purpose of overcoming these restrictions.

Improvement of PCR

As DNA polymerase for PCR, DNA polymerase derived from a thermophilic bacterium *Thermus.aquaticus* (Taq DNA polymerase) used to be generally used in the initial period (Non-patent Document 1). Based on this enzyme, subsequently various enzymes and reagents/kits for PCR have been developed and distributed. Most of them have an improved feature on any of the aforementioned technical restrictions, and the reagents/kits having such characteristics have been distributed by various manufacturers. Some examples of the improved PCR methods are shown below.

As an example of enhancing the fidelity to the template, DNA polymerase with high fidelity is generally used for the PCR method. Taq DNA polymerase is a PolI type DNA polymerase having only 5→-->3' polymerase activity and having no 3'-->5' exonuclease activity. On the contrary, DNA polymerase derived from an ultrathermophilic archaebacterium, *Pyrococcus.furiosus* is an α type DNA polymerase which has both the 5'-->3' polymerase activity and the 3'-->5' exonuclease activity. The 3'-->5' exonuclease activity works as a proof reading activity. Thus, when this DNA polymerase is used for PCR, the fidelity to the template upon amplification is strikingly enhanced compared to amplification with Taq DNA polymerase having no 3'-->5' exonuclease activity (Non-Patent Document 2).

Examples of commercially available products among such DNA polymerases may include Pyrobest DNA polymerase (TAKARA BIO INC.), Pfu DNA polymerase (Stratagene), KOD DNA polymerase (Toyobo Co., Ltd.), DeepVent DNA polymerase (New England Biolabs (NEB)), Vent DNA polymerase (NEB) and Pwo DNA polymerase (Roche Diagnostics).

Barns et al. has reported that when the a type DNA polymerase having the proof reading function and the PolI type DNA polymerase having no proof reading function were mixed at an appropriate ratio and used for PCR, the length of the extendable target sequence was increased and the amplification efficiency was also enhanced (Non-patent Document 3, Patent Document 1). Examples of the commercially available products of such mixed DNA polymerases may include TaKaRa EX Taq DNA polymerase (TAKARA BIO INC.) and Taq Plus Long (Stratagene).

As one example of the strategy directing to enhancement of the reaction specificity of PCR, a hot start method has been known. Non-specificity in PCR is often caused by non-specific annealing of the primer to the template DNA. To prevent this phenomenon, the hot start method is effective in which the PCR is started immediately after completely mixing a PCR reaction solution at high temperature. Several methods for the hot start method have been reported. In a current mainstream, DNA polymerase is complexed with its specific antibody and inactivated at low temperature, and the DNA polymerase is activated under a high temperature condition upon hot start to initiate the PCR reaction. It has been reported that the specificity of the PCR reaction is enhanced by this method (Patent Document 2). Products associated with this hot start method are also distributed by gene engineering manufacturers, and generally utilized.

The aforementioned methods for improving the PCR method all have come into practical use, commercialized and generally used, but all have both advantages and disadvantages, and do not satisfy all the points for improvement in the PCR method discussed in the above. For example, the α type DNA polymerase with high fidelity is often inferior to the PolI type DNA polymerase in terms of extendibility. As to the PCR method using the mixture of the α type DNA polymerase and the PolI type DNA polymerase, the fidelity thereof is inferior to that of DNA polymerase with high fidelity. Thus it is desired to develop DNA polymerase or a DNA amplification system which is excellent in all of the points.

DNA Replication Process

Generally, it is required for initiation of the DNA replication that a double strand structure is unpaired at an origin of the replication. DNA helicase is required for that process. A single strand DNA binding protein is bound to the unpaired DNA to stabilize the single strand. Furthermore, primase works on each chain to synthesize the primer. Subsequently, a replication factor C (RFC) recognizes the primer and binds thereto for inducing a proliferation cell nuclear antigen (PCNA) on the DNA chain. PCNA serves as a clump to fasten the DNA polymerase on the DNA chain. And DNA polymerase complexed with PCNA synthesizes a new chain. In a process of continuous synthesis, the long new chain is synthesized in accordance with the aforementioned manner. In a process of discontinuous synthesis, RNA primer attached to each Okazaki fragment is decomposed with nuclease whereby it is replaced with the DNA chain. Subsequently the fragments are connected with DNA ligase, to complete one new chain (Non-patent Documents 4 and 5).

Pfu-PCNA and RFC

It has been reported that *Pyrococcus.furiosus* PCNA (hereinafter represented by "Pfu-PCNA" or "PfuPCNA") has a molecular weight of 28.0 kDa, forms a homotrimer in a similar manner to PCNA in eukaryotic organisms and works by interacting with polymerase (Non-Patent Document 6). Meanwhile, *Pyrococcus.furiosus* RFC (hereinafter represented by "Pfu-RFC" or "PfuRFC") has a structure constituted by subunits RFCS and RFCL. The open reading frame for Pfu-RFCS encodes one intein and mature Pfu-RFCS has the molecular weight of 37.4 kDa. Pfu-RFCL has the molecular weight of 55.3 kDa. It has been reported that an addition of Pfu-RFC and Pfu-PCNA remarkably promoted the DNA extension activity of Pfu DNA polymerase in a primer extension analysis (Non-patent Document 7).

Structure and nature of Pfu-PCNA

A crystal structure analysis of Pfu-PCNA was performed (Non-patent Document 8). According to that analysis, a Pfu-PCNA trimer is formed with hydrogen bonds between main chain anti-parallel β strands, βI1 and βD2, of two subunits (T108-K178, T110-E176, R112-E174). Further, an intermolecular ion pair network consisting of acidic and basic amino acid side chains is involved in keeping the trimer structure. There is a report on investigation for two mutants, PfuPCNA (D143A) and PfuPCNA (D143A/D147A), obtained by substituting D143 and D147 with alanine, which is a neutral amino acid, among residues involved in the ion pair network (R82, K84 and R109 in an N terminal region and E139, D143 and D147 in a C terminal region) (Non-patent Document 9). In this report, it has been described that PfuPCNA (D143A) and PfuPCNA (D143A/D147A) are eluted in gel filtration at positions corresponding to monomers, and that the crystal is obtained as not the trimers but V-shaped dimers. The report also describes additional results of measuring the activity in the primer extension analysis. In the report, it is concluded that PfuPCNA (D143A/D147A) did not exhibit a DNA synthesis promoting activity both in the cases of PCNA alone and in combination with RFC, whereas PfuPCNA (D143A) exhibited the DNA synthesis promoting activity regardless of the presence or absence of RFC and, in the case of PCNA alone, showed better result than a wild type PCNA.

KOD-PCNA and RFC

KOD-PCNA (hereinafter represented by "KOD-PCNA" or "KODPCNA") and KOD-RFC (hereinafter represented by "KOD-RFC" or "KODRFC") are PCNA and RFC obtained from *Themmococcus.kodakaraensis* KOD-1 strain.

KOD-PCNA has been reported in Non-patent Document 12. According to this report, KOD-PCNA has 249 residues and its theoretical molecular weight is 28.2 kDa. Pfu-PCNA reported previously also has 249 residues, and 84.3% of amino acid residues in both amino acid sequences are identical. KOD-PCNA as well as Pfu-PCNA keeps all of the conservative regions characteristic for PCNA. Although the crystal structure analysis of KOD-PCNA is not performed, it has been described that it is highly likely that KOD-PCNA forms the homotrimer in the same form as in Pfu-PCNA assumed on the basis of its high homology to Pfu-PCNA.

KOD-RFC has been reported in Non-patent Document 10. According to the report, KOD-RFC takes the same subunit structure consisting of RFCL and RFCS as the other RFCs. KOD-RFCL has the molecular weight of 57.2 kDa. The RFCS gene encodes one intein in the open reading frame, and mature KOD-RFCS has the molecular weight of 37.2 kDa.

The above two documents have also reported the effects when KOD-PCNA and KOD-RFC were added to the DNA synthesis system with KOD-DNA polymerase. In the reports, it has been described that KOD-PCNA alone and KOD-PCNA in combination with KOD-RFC promoted the extension activity in the primer extension experiment, and the "sensitivity" was enhanced when KOD-PCNA was added in the PCR reaction system.

Patent Document 1: U.S. Pat. No. 5,436,149
Patent Document 2: U.S. Pat. No. 5,338,671
Nonpatent Document 1: Saiki, R. K., Gelfand, D. H., Stoffel, S., Scharf, S. J., Higuchi, R., Horn, G. T., Mullis, K. B. and Erlich, H. A., Science, 239, 487-491 (1988)
Nonpatent Document 2: Cline, J C Braman, and H H Hogrefe Nucl. Acids Res., 24, 3546-3551 (1996)
Nonpatent Document 3: Barnes, W. M., Proc. Natl. Acad. Sci., 91, 2216-2220 (1994)
Nonpatent Document 4: Waga, S, and Stillman, B. Annu. Rev. Biochem., 67, 721-751 (1998)
Nonpatent Document 5: Kornberg, A. and Baker, T. A., DNA replication, 2nd ed. W.H. Freeman, New York. (1992)
Nonpatent Document 6: Cann et al., J. Bacteriol., 181, 6591-6599 (1999)
Nonpatent Document 7: Cann et al., J. Bacteriol., 183, 2614-2623 (2001)
Nonpatent Document 8: Matsumiya et al., Protein Sci., 10, 17-23 (2001)
Nonpatent Document 9: Matsumiya et al., Protein Sci., 12, 823-831 (2003)
Nonpatent Document 10: Kitabayashi et al. Biosci Biotechnol Biochem., November; 67(11): 2373-2380 (2003)
Nonpatent Document 11: Takagi et al., Appl. Environ. Microbiol., November; 63(11): 4504-4510 (1997)
Nonpatent Document 12: Kitabayashi et al., Biosci. Biotechnol. Biochem., October; 66(10): 2194-2200 (2002)

DISCLOSURE OF INVENTION

Problem to be Solved by the Invention

Under such a circumstance, it is an object to construct a DNA amplification system which is excellent in general versatility and is used easily.

Means for Solving Problem

The present inventors have attempted to establish a novel DNA amplification system which overcomes shortcomings in the existing PCR technology by reconstructing an intracellular DNA replication system in vitro using a variety of factors utilized in the aforementioned DNA replication process (hereinafter also represented by an "accessory protein or "AP") and DNA polymerase. In particular, the present inventors focused on DNA polymerase derived from an ultrathermophilic archaebacterium, *Pyrococcus.furiosus*, which has the 3'-->5' exonuclease activity and the high fidelity to the template, and PCNA and RFC which are highly likely to directly interact with DNA polymerase among various factors (accessory proteins) in the intracellular DNA replication system, and advanced the extensive study.

As a result, the present inventors have obtained findings that a PCNA which can promote a DNA extension reaction with well-balanced extendibility and the fidelity without depending on the presence or absence of RFC can be obtained by preparing PCNA so as to include a site which causes, when an N terminal region of the PCNA monomer and a C terminal region of another PCNA monomer act as an interface to form a multimeric complex, an intermolecular interaction of the monomers in an interface region of the monomers, said PCNA monomer further comprising amino acid residues in said site causing mutual charge repulsion, and thereby have completed the present invention. The present invention thus provides the following PCNA and other inventions.

(1) A mutant PCNA monomer comprising a site which causes, when an N terminal region of the PCNA monomer and a C terminal region of another PCNA monomer act as an interface to form a multimeric complex, an intermolecular interaction of the monomers in an interface region of the monomers, said PCNA monomer further comprising amino acid residues in said site causing mutual charge repulsion;

said monomer itself or the multimeric complex thereof having an activity to promote DNA replication.

(2) The mutant PCNA monomer according to (1) wherein said PCNA monomer has an amino acid sequence obtained by substituting an amino acid residue at least at one position selected from the group consisting of positions 82, 84, 109, 139, 143 and 147 in an amino acid sequence according to SEQ ID NO:2 or 32 with another amino acid residue, and wherein amino acid residues are composed so that one or more amino acid residues selected from the group (i) and one or more amino acid residues selected from the group (ii) cause the mutual charge repulsion:

(i) a group of amino acid residues at positions 82, 84 and 109, and (ii) a group of amino acid residues at positions 139, 143 and 147.

(3) The mutant PCNA monomer according to (2) comprising mutations of one or several amino acid residues selected from the group consisting of an addition, an insertion, a substitution and a deletion at position(s) other than the positions 82, 84, 109, 139, 143 and 147.

(4) The mutant PCNA monomer according to (3) having a sequence obtained by substituting the amino acid residue at position 73 with leucine in an amino acid sequence according to SEQ ID NO:2 or 32.

(5) The mutant PCNA monomer according to any one of (2) to (4) wherein one or more amino acids selected from said group (i) and one or more amino acids selected from said group (ii) are both acidic amino acids or both basic amino acids.

(6) The mutant PCNA monomer according to any one of (2) to (5) having the sequence obtained by substituting the amino acid residue at position 143 with arginine in the amino acid sequence according to SEQ ID NO:2 or 32.

(7) A polynucleotide encoding an amino acid sequence of the PCNA monomer according to any one of (1) to (6).

(8) A transformant in which the polynucleotide according to (7) has been introduced.

(9) A method for producing a mutant PCNA wherein the transformant according to (8) is cultured in a medium and a PCNA monomer and/or a multimeric complex composed of said monomer is accumulated in said transformant and/or the medium.

(10) A reagent for DNA replication comprising the PCNA monomer according to any one of (1) to (6) and/or a multimeric complex composed of said monomer.

(11) A kit for DNA replication comprising the reagent according to (10).

(12) The kit for DNA replication according to (11) further comprising a reagent for PCR.

(13) A method for replicating DNA wherein DNA synthesis is performed in the presence of the PCNA monomer according to any one of (1) to (6) and/or a multimeric complex composed of said monomer, and DNA polymerase.

(14) The method for replicating the DNA according to (13) wherein said DNA synthesis is PCR.

The present invention has specified the amino acid sequence in the interface region of PCNA monomers so that the DNA replication reaction can be further promoted. The PCNA of the present invention has applicability to many DNA polymerases derived from different bacterial hosts and the high versatility. The PCNA of the present invention can exert an extremely unique performance compared with conventional ones in terms of exerting the excellent DNA extension promoting activity even when RFC is not used in combination.

Effect of the Invention

According to the present invention, a DNA replication promoting factor which promotes a DNA extension reaction and has the high versatility is provided. According to the present invention, it is possible to perform the DNA extension reaction which is excellent in various properties such as extendibility and reaction rate.

EXPLANATIONS OF LETTERS OR NUMERALS

Figure 1:
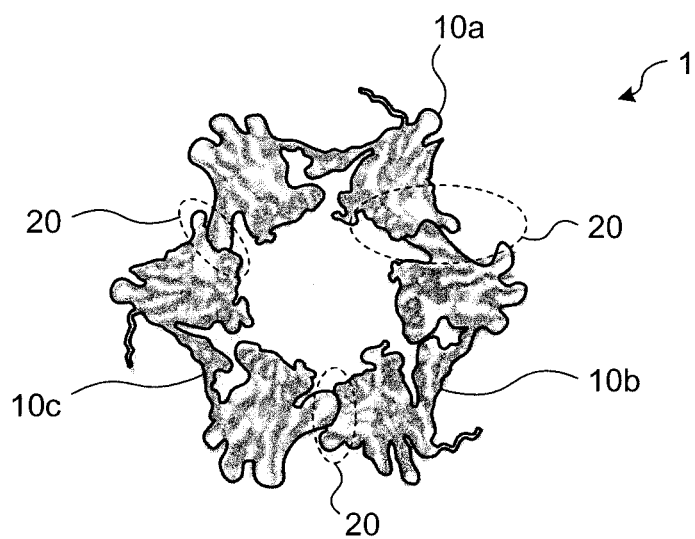
FIG. 1 is a view schematically showing a trimer of PCNA.

1 PCNA trimer
10a, 10b and 10c PCNA monomer
20 Joint of PCNA monomers
PCNA gene PCNA gene ORF
T7 promoter: T7 promoter
rbs Ribosome binding site
T7 terminator: T7 terminator
Amp Ampicillin resistant gene
Ori Origin of replication
RFCL gene RFCL gene ORF
RFCSm gene Mature RFCS gene ORF
Kan Kanamycin resistant gene

BEST MODE FOR CARRYING OUT THE INVENTION

The present invention will be described in more detail below with referring to embodiments of the present invention. Upon carrying out biochemical or gene engineering techniques in the present invention, descriptions in various experimental manuals, e.g., Molecular Cloning: A LABORATORY MANUAL, 3rd edition, Cold Spring Harbor Laboratory Press, Cold Spring Harbor, N.Y. (2001); *Shin-Idenshi Kogaku Handbook* (New Genetic Engineering Handbook; edited by Masami Muramatsu, Yodosha, Experimental Medicine, Supplementary Volume, 3rd edition, 1999); *Tanpakushitsu Jikken no Susumekata* (How to Proceed with Experiments on Proteins; edited by Masato Okada and Kaori Miyazaki, Yodosha, 1st edition, 1998); *Tanpakushitsu Jikken Note* (Notebook for Experiments on Proteins; edited by Masato Okada and Kaori Miyazaki, Yodosha, 2nd edition, 1999); *Tanpakushitsu Jikken Handbook* (Handbook for Experiments on Proteins; edited by Tadaomi Takenawa, Experimental Medicine, Supplementary Volume, 1st edition, Aug. 15, 2003); and *PCR Jikken Note* (Notebook for Experiments for PCR; edited by Taketoshi Taniguchi, Yodosha, 1st edition, 1997) are available as references.

For base sequences, amino acid sequences and individual components thereof, symbols simplified by alphabetical representation are sometimes used herein, and the representation in all cases comply with common practice in the molecular biological and gene engineering fields.

To simply show the mutation in the amino acid sequence herein, for example, the representation such as "D143A" is used. "D143A" indicates that aspartic acid at position 143 was substituted with alanine, i.e., indicates the type of the amino acid residue before the substitution, its position and the type of the amino acid residue after the substitution. Unless otherwise specified, each sequence ID number corresponds to SEQ ID NO described in Sequence Listing.

1. PCNA in the Present Invention

In the PCNA monomer of the present invention, the amino acid residue at a certain location in the interface region which contributes to the multimeric formation is specified. That is, in the PCNA monomer of the present invention, the site at which the intermolecular interaction is formed in the interface region is composed of the amino acid residues which generate a mutual charge repulsion between the monomers.

Here the "intermolecular interaction" refers to the physical, chemical or electric interaction which occurs between the molecules, and examples thereof may include actions caused by a molecular structure such as a conformation and a steric structure, as well as various intermolecular actions such as ion bonds, hydrogen bonds and a hydrophobic interaction. When the PCNA monomers form a multimeric complex, the multimeric complex is formed by the intermolecular interaction, e.g., mutual attraction or joining of the interface regions of the monomers. In one preferable embodiment, the amino acid residues are composed so that the amino acid residues which form intermolecular ion pairs or an ion pair network are mutually repulsed in terms of electrical charge. The PCNA monomer of the present invention has an activity to promote the DNA replication. The activity is excerted by the monomer itself or the multimeric complex thereof. The "mutant" when referred to as the "mutant PCNA" herein means comprising the amino acid sequence different from that of conventionally known PCNA, and does not distinguish whether the mutant is artificially mutated or naturally occurs.

Figure 2:
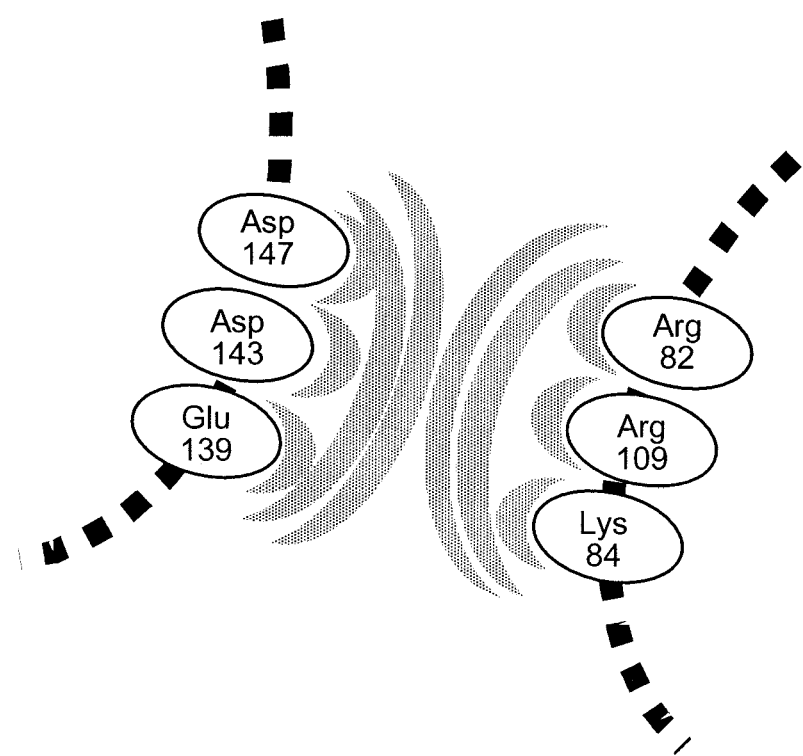
FIG. 2 is a view showing one example of an intermolecular interaction site of monomers formed in a mutual interface region which is a joint of the monomers when PCNA monomers form a multimeric complex.

The multimeric complex of PCNA which is one of the factors involved in the DNA replication reaction is formed by joining of the monomers on an interface of an N terminal region of one monomer and a C terminal region of another monomer. The N terminal region herein means the portion from the center to the N terminus and the C terminal region herein means the portion from the center to the C terminus when the protein is regarded as one chain. In eukaryotic cells and archaebacteria, PCNA forms the trimer in many cases. A trimer model of PCNA was illustrated in FIG. 1. As shown in FIG. 1, the PCNA monomer 10a, 10b or 10c is joined with another monomer in each terminal region to form the multimeric complex 1 having a ring structure. At a joint 20, the terminal region of the monomers makes the interface, and the intermolecular interaction which attracts the monomers is formed inside thereof. A model of the intermolecular interaction in *Pyrococcus.furiosus* PCNA is shown in FIG. 2. In FIG. 2, PCNA having the amino acid sequence described in SEQ ID NO:2 (amino acid sequence of wild type Pfu-PCNA) is described. The amino acid residues contained in the N terminal region of one monomer 10a and the amino acid residues contained in the C terminal region of another monomer 10c form an intermolecular pair. As shown in FIG. 2, it is conceivable that the amino acid residue group at positions 139, 143 and 147 and the amino acid residue group at positions 82, 84 and 109 in the amino acid sequence described in SEQ ID NO:2 form the network of mutual affection.

On the contrary, in the present invention, the interface is constituted so that at least some amino acid residues at the site at which the intermolecular interaction occurs are positively repulsed mutually. "Mutual charge repulsion" herein refers to the mutual repulsion by the charges of the amino acid residues in the interface region. Therefore, examples of such a combination may include an combination where the amino acid residues contained in the interface region are both composed of positively charged molecules and an combination where the amino acid residues contained in the interface region are both composed of negatively charged molecules. More specifically, it is preferable that combination consists of amino acid residues both of which are acidic amino acids or both of which are basic amino acids. The acidic amino acid may include aspartic acid (abbreviated as Asp or D) and glutamic acid (abbreviated as Glu or E). The basic amino acid may include lysine (abbreviated as Lys or K), arginine (abbreviated as Arg or R) and histidine (abbreviated as His or H).

Therefore, on the basis of the PCNA having the amino acid sequence described in SEQ ID NOS: 2 or 32, the PCNA of the present invention is obtainable by altering the amino acid residue at least at one position selected from the group consisting of positions 82, 84, 109, 139, 143 and 147 in the amino acid sequence described in SEQ ID NOS: 2 or 32. As a preferable embodiment of the present invention, an embodiment composed of the amino acid residues where one or more amino acid residues selected from the following group (i) and one or more amino acid residues selected from the following group (ii) cause the mutual charge repulsion is exemplified.
(i) Amino acid residue group at positions 82, 84 and 109; and
(ii) amino acid residue group at positions 139, 143 and 147.

More specifically, it is suitable that the combination of one or more amino acid residues selected from the aforementioned (i) and one or more amino acid residues selected from the aforementioned (ii) are both the acidic amino acids or are both the basic amino acids. That is, the preferable embodiments may include an embodiment in which at least one amino acid residue selected from the group (i) and at least one amino acid residue selected from the group (ii) are both the acidic amino acids selected from the group consisting of aspartic acid and glutamic acid, and an embodiment in which at least one amino acid residue selected from the group (i) and at least one amino acid residue selected from the group (ii) are both the basic amino acids selected from the group consisting of lysine, arginine and histidine.

The activity to promote the DNA replication (DNA replication promoting activity) means that the DNA replication is promoted compared with the replication with the original wild type PCNA. Specifically, it is more preferable that the DNA replication promoting activity is higher than that of the PCNA monomer having the amino acid sequence described in SEQ ID NOS:2 and 32 or the multimeric complex thereof. As another specific indicator, it is preferable to have the DNA replication promoting activity which increases the activity to an equivalent extent and up to 10 times or more compared with the activity of Taq polymerase in terms of extendibility and reaction rate when the extendibility and the reaction rate are measured according to the method of measuring the DNA replication activity shown in the Examples mentioned below.

The PCNA of the present invention includes a PCNA which is substantially identical to the PCNA having the aforementioned mutation-containing amino acid sequence. Specifically, the PCNA of the present invention includes a mutant PCNA having the preferable DNA replication promoting activity as described above and comprising mutations of one or several amino acid residues selected from the group consisting of an addition, an insertion, a substitution and a deletion in the range of not inhibiting the effect of the present invention at positions other than the positions 82, 84, 109, 139, 143 and 147. "Several amino acids" are specifically 2 to 50, preferably 2 to 30, more preferably 2 to 10 and particularly preferably 2 to 5 amino acids. In such a protein, the amino acid residues corresponding to the positions selected from the group (i) and the group (ii) in the amino acid sequence described in SEQ ID NOS:2 and 32 are constituted to mutually cause the charge repulsion. That is, other mutations are acceptable in the amino acid residues other than the predetermined amino acid residues according to the positions of the group (i) and/or the group (ii), provided that the activity is not remarkably impaired. Such a mutation may include a so-called conservative substitution of the amino acid residue. When the mutation e.g., the deletion, the insertion or the addition is introduced into the position other than the positions 82, 84, 109, 139, 143 and 147, the number of the amino acid residues after introducing the mutation may be different from the number of the amino acid residues before introducing the mutation. However, insofar as the position corresponds to the position shown in the aforementioned (i) and (ii) which locate in the interface and mutually give the intermolecular interaction for forming the multimeric complex, the PCNA having the shifted number is included in the PCNA of the present invention. Among the aforementioned mutant PCNA, particularly those containing only the substitution of the amino acid residue at position 73 with leucine or those containing the other mutation in addition thereto are preferable because they can easily prepared and purified.

An action mechanism whereby the PCNA of the present invention can promote the DNA replication reaction is not exactly clear. However, it is speculated that the ring structure formed by the multimeric complex becomes in a form such that the complex is dissociated upon temperature elevation, whereby the DNA replication reaction is smoothly repeated and consequently the DNA replication reaction is further promoted. Conventionally, the idea which has been widely accepted was that PCNA monomers joined firmly to form the multimeric complex would exert a role as a stable clamp and working as the DNA replication promoting factor. However, in this point, the present invention provides findings different from conventional one. That is, without concurrent use of RFC, too firm bonds in the multimeric complex are not good for the PCNA activity. In particular upon repetition of the DNA replication such as PCR, when the ring structure is weakened so that the complex is dissociated upon temperature elevation, the PCNA exerts higher promoting activity than that the wild type PCNA exerts in combination with RFC.

A specific example of the preferable PCNA of the present invention may include the PCNA monomer having the sequence (D143R) in which aspartic acid at position 143 has been substituted with arginine. The amino acid residue at position 143 belongs to the group (ii). In this case, the amino acid residues at positions 82, 84 and 109 belonging to the group (i) are arginine, lysine and arginine, respectively, and the intermolecular interaction may be in a state where the interface regions are mutually repulsed more strongly than usual. The PCNA in this form has well-balanced extendibility and reaction rate in the DNA replication reaction and exerts a particularly excellent ancillary action.

The present invention also provides a polynucleotide encoding the PCNA of the present invention. The amino acid is deduced from the base sequence by a codon table, and due to degeneracy of the codons, one amino acid sequence may be encoded by a plurality of base sequences. For example, the amino acid sequences described in SEQ ID NOS:2 and 32 are encoded by the base sequences described in SEQ ID NOS:1 and 31. Therefore, an embodiment of the polynucleotide of the present invention may be the following polynucleotide (a).

(a) Polynucleotide having a base sequence encoding an amino acid sequence in which one or more amino acid residues selected from the group (i) and one or more amino acid residues selected from the group (ii) in the amino acid sequence described in SEQ ID NOS:2 and 32 have been substituted to mutually cause the charge repulsion.

The polynucleotide having the base sequence such as (a) may be easily prepared by modifying the base sequence at the positions corresponding to the amino acid residues at the predetermined positions in the base sequence described in SEQ ID NOS:1 and 31. Conversion of the base sequence based on the type of the amino acid may be easily performed based on the codon table. The polynucleotide referred to herein may include both DNA and RNA, a double strand and a single strand, and may also include chimeric molecules of DNA and RNA and hybrids of DNA and RNA.

The following polynucleotide (b) may also be included in the polynucleotide of the present invention.

(b) Polynucleotide which hybridizes with the polynucleotide having the base sequence complementary to the base sequence of the aforementioned polynucleotide (a) under a stringent condition; which has the base sequence encoding the amino acid sequence combining the amino acid residues so that one or more amino acid residues selected from the group (i) and one or more amino acid residues selected from the group (ii) mutually cause the charge repulsion; and which encodes the PCNA having the aforementioned DNA replication promoting activity.

A probe which may be used for obtaining the gene to be hybridized may be prepared by standard methods based on the base sequence described in SEQ ID NO:1 or 31. The objective polynucleotide may also be isolated by using the probe to pick up the polynucleotide to be hybridized therewith according to the standard method. For example, the probe may be prepared by amplifying the base sequence cloned in a plasmid or a phage vector, and cutting out and extracting the base sequence for use as the probe with restriction enzymes. A site to be cut out may be regulated depending on the objective DNA.

The "stringent condition" refers to the condition where a so-called specific hybrid is formed whereas no non-specific hybrid is not formed. Examples thereof may be conditions where hybridization occurs at salts concentrations equivalent to 1×SSC and 0.1% SDS at 60° C. and preferably 0.1×SSC and 0.1% SDS at 60° C., which is a washing condition of an ordinary Southern hybridization. As the polynucleotide to be hybridized under the "stringent condition", it is suitable that the aforementioned polynucleotide (b) has preferably 50% or more, more preferably 80% or more, still more preferably 90% or more and still more preferably 95% or more homology to the polynucleotide (a). As the method for calculating the homology, for example BLAST, FASTA, Clustal W and the like may be used.

The protein comprising the amino acid sequence obtained by translating the base sequence of the aforementioned polynucleotide (b) has the DNA replication promoting activity. More specifically, this protein has the same DNA replication promoting activity as the activity of the aforementioned protein of the present invention.

The polynucleotide of the present invention can be incorporated into an appropriate vector and used as a recombinant polynucleotide. The recombinant polynucleotide herein refers to a hybrid molecule obtained by ligating two or more polynucleotides. The preferable embodiment of the recombinant polynucleotide of the present invention may include an expression vector. Various forms of the expression vectors have been already known and some of them are commercially available. The embodiment of the recombinant polynucleotide may be appropriately selected depending on the intended use, and the publicly known expression vectors such as commercially available expression vectors can be used. Specific examples related to the expression vectors are shown below in a non-limited manner.

As the vector, plasmids derived from *Escherichia coli* (e.g., pBR322, pBR325, pUC12, pUC13, commercially available pBT Vector and pTRG Vector (Stratagene)); plasmids derived from yeast (e.g., YEp24, YCp50); bacteriophages such as λ phage; animal viruses such as retrovirus, vaccinia virus and baculovirus; plasmids suitably used for *Bacillus subtilis* (e.g., pUB110, pTP5, pC194); as well as pA1-11, pXT1, pRc/CMV, pRc/RSV, pcDNAI/Neo and the like are used.

Any promoters may be used as long as they are suitably associated with host cells for the gene expression. For example, when the host cell is derived from genus *Escherichia*, a trp promoter, a lac promoter, a recA promoter, a λPL promoter, an lpp promoter and a T7 promoter may be used. When the host cell is derived from genus *Bacillus*, an SPO1 promoter, an SPO2 promoter and a penP promoter may be used. When the host cell is yeast, a PHO5 promoter, a PGK promoter, a GAP promoter and an ADH promoter may be used. When the host cell is an insect cell, a polyhedrin promoter and a P10 promoter may be used. When an animal cell is used as the host cell, an SRα promoter, an SV40 promoter, an HIV/LTR promoter, a CMV (cytomegalovirus) promoter and an HSV-TK promoter may be used.

It is preferable in terms of easy recombination manipulation that the expression vector has multicloning sites. In addition to the aforementioned, a selection marker, an enhancer, a splicing signal, a poly A addition signal, an SV40 replication origin (hereinafter sometimes abbreviated as SV40ori) and a terminator can be incorporated into the expression vector if desired. Examples of the selection marker may include an ampicillin resistant gene (also referred to as a carbenicillin resistant gene, sometimes abbreviated as Amp), a kanamycin resistant gene (sometimes abbreviated as Kam), a tetracycline resistant gene (sometimes abbreviated as Tet), a dihydrofolic acid reducing enzyme (sometimes abbreviated as dhfr) gene (methotrexate [MTX] resistant) and a neomycin resistant gene (sometimes abbreviated as Neo, G418 resistant). If necessary, a signal sequence adapted for the host cell is added to the N terminal side of a random oligonucleotide or a cassette of the present invention.

When the host cell is derived from genus *Escherichia*, a PhoA signal sequence and an OmpA signal sequence can be utilized. When the host cell is derived from genus *Bacillus*, an α-amylase signal sequence and a subtilisin signal sequence can be utilized. When the host cell is yeast, an MFα signal sequence and an SUC2 signal sequence can be utilized. When the host cell is an animal cell, an insulin signal sequence, an α-interferon signal sequence and an Ras farnesylation signal sequence can be utilized.

A transformant which expresses the DNA polymerase of the present invention can be produced by preparing the expression vector containing the polynucleotide of the present invention as discussed above and then introducing this into the host cell.

Examples of the host cells may include bacterial cells derived from streptococci, staphylococci, *Escherichia coli*, *Streptomyces* and *Bacillus subtilis*; fungal cells derived from yeast and *Aspergillus*; insect cells such as *Drosophila* S2 and Sf9 (Spodoptera Sf9); animal cells such as CHO, COS, HeLa, C127, 3T3, BHK, HEK293, Bows cells, melanoma cells and hematopoietic cells as well as plant cells.

The expression vector can be introduced into the host cell by the method described in many standard experimental manuals such as Davis et al., BASIC METHODS IN MOLECULAR BIOLOGY (1986); Sambrook et al., MOLECULAR CLONING: A LABORATORY MANUAL, 3rd edition, Cold Spring Harbor Laboratory Press, Cold Spring Harbor, N.Y. (2001). More specifically, calcium phosphate transfection, the transfection mediated through DEAE-dextran, microinjection, the transfection mediated through cation lipid, electroporation, transduction, biolistics introduction or infection is available.

The transformant may be cultured by controlling conditions depending on the type of the host. Many types of the hosts are available, and some specific examples of the conditions are as follows. For example, when a transformant derived from *Escherichia* or *Bacillus* as the host is cultured, the medium used for culturing may be a liquid medium or an agar medium, to which carbon sources, nitrogen sources, inorganic matters and others required for the growth of the transformant may be added. Examples of the carbon sources may include glucose, dextrin, soluble starch and sucrose. Examples of the nitrogen sources may include inorganic or organic substances such as ammonium salts, nitrate salts, corn steep liquor, peptone, casein, meat extracts, soybean cakes and potato extracts. Examples of the inorganic salts may include calcium chloride, sodium dihydrogen phosphate and magnesium chloride. Yeast extracts, vitamins and growth promoting factors may also be added. A pH value of the medium is desirably about 5 to 8. As the suitable medium when the *Escherichia* cells are cultured, specifically LB medium containing yeast extract, trypton and the salt (NaCl) is exemplified. In order to make the promoter work efficiently as needed, an inducer such as isopropyl 1-thio-β-galactoside (IPTG) may be added thereto. When the host is *Escherichia*, culturing is typically performed at about 15 to 43° C. for about 3 to 24 hours, and if necessary ventilation and stirring may be performed. When the host is *Bacillus*, culturing is typically performed at about 30 to 40° C. for about 6 to 24 hours, and if necessary ventilation and stirring may be performed.

When the transformant derived from the yeast as the host is cultured, examples of the medium therefor may include a Burkholder minimum medium and an SD medium containing 0.5% casamino acids. It is preferable that the pH value in the medium is adjusted to about 5 to 8. Culturing is typically performed at about 20 to 35° C. for about 24 to 72 hours, and if necessary ventilation and stirring may be performed.

When the transformant derived from the insect cell or the insect as the host is cultured, those obtained by appropriately adding an additive such as 10% inactivated bovine serum to Grace's Insect Medium (Grace, T. C. C., Nature, 195, 788 (1962) may be used as the medium. It is preferable that the pH value in the medium is adjusted to about 6.2 to 6.4. Culturing is typically performed at about 27° C. for about 3 to 5 days, and if necessary ventilation and stirring may be performed.

When the transformant derived from the animal cell as the host is cultured, a MEM medium, a DMEM medium, an RPMI1640 medium (The Journal of the American Medical Association, 199: 519 (1967)) and a 199 medium (Proceeding of the Society for the Biological Medicine, 73: 1 (1950)) containing about 5 to 20% fetal calf serum may be used. It is preferable that the pH value is adjusted to about 6 to 8. Culturing is typically performed at about 30 to 40° C. for about 15 to 60 hours, and if necessary ventilation and stirring may be performed. If necessary, a concentration of $CO_2$ is controlled.

The protein of the present invention produced by the transformant can be purified and isolated if necessary by the standard methods for protein purification. As discussed above, the PCNA of the present invention can be obtained using the transformant.

2. Method for DNA Replication Using PCNA of the Present Invention

The method for DNA replication of the present invention is characterized in that DNA is synthesized in the presence of the PCNA monomer and/or the multimeric complex composed of the PCNA monomers with DNA polymerase. The method for synthesizing the DNA may be PCR, a primer extension, a nick translation, and the synthesis of the first strand cDNA by reverse transcriptase.

A preferable example of the method for DNA replication of the present invention may be the DNA amplification by PCR. In the PCR, the DNA replication using the primers and the template DNA is repeated to amplify the DNA exponentially.

Thus, it is desirable that the PCNA serves as a function of a clamp for DNA polymerase, and the PCNA is rapidly removed from the template after DNA polymerase is stabilized on the template or after the predetermined region is amplified. It is speculated that the PCNA of the present invention has such properties.

The PCNA of the present invention is well-compatible with various DNA polymerases and thus has high versatility. In general, DNA polymerases are excellent in either one of extendibility and fidelity, and thus has both advantages and disadvantages. However, by combining with the PCNA of the present invention, it is possible to enhance the extendibility without reducing the fidelity. Thus, the DNA replication activity can be augmented with reinforcing the shortcoming of DNA polymerase. Examples of the DNA polymerase which is applicable to the method for DNA replication of the present invention may include most DNA polymerases mainly used at present, e.g., Pyrobest DNA Polymerase (TAKARA BIO INC.), TaKaRa EX Taq (TAKARA BIO INC.), Vent DNA Polymerase (NEW ENGLAND BioLabs), Deep VentR DNA Polymerase (New England Biolabs), Pfu Turbo DNA Polymerase (Stratagene), KOD DNA Polymerase (Toyobo Co., Ltd.) and Pwo DNA Polymerase (Roche Diagnostics). The PCNA of the present invention is particularly effective for enhancing the extendibility, and is particularly useful when used in combination with α-type DNA polymerase which is superior in fidelity but inferior in extendibility.

In the method for DNA replication of the present invention, the PCNA of the present invention requires no RFC, and thus, RFC need not be added to a reaction system. No RFC preparation is commercially available in general, and preparation thereof is a burden. Even if the RFC preparation is available, when it is added to use, it is necessary to determine the conditions such as appropriate amount ratios to various factors other than RFC in the DNA replication system. The present invention has an advantage that these need not be considered. Particularly in the use for PCR, the PCNA of the present invention even without RFC exerts better promoting activity than the wild type PCNA in combination with RFC.

As to the specific conditions for PCR, many instruction manuals have been already published, and the conditions in the method of the present invention may be controlled appropriately with reference to those references. As the conditions for PCR, for example, the amount of DNA polymerase to be added, the reaction time of PCR, the temperature of the reaction solution, components of the reaction solution, pH in the reaction solution and the amount of the template polynucleotide to be added are controlled.

3. Reagent Kit

The reagent kit of the present invention is a reagent kit for DNA replication comprising the aforementioned PCNA of the present invention and if necessary another reagents. The PCNA of the present invention can be suitably used in an embodiment comprising the monomer and/or the multimeric complex composed of the monomers, as one ingredient of the reagents for DNA replication. The reagent kit of the present invention is particularly suitable as the reagent kit for PCR because the PCNA of the present invention can be used particularly suitably in PCR.

The PCNA in the reagent kit of the present invention may be any form such as a purified protein, a recombinant polynucleotide in which the polynucleotide encoding the protein has been incorporated, and a transformant in which this recombinant polynucleotide has been introduced. The preferable forms of the recombinant polynucleotide and the transformant are as described above. The PCNA of the present invention may be combined with another PCNA. When the PCNA of the present invention is provided in the form of the recombinant DNA or the transformant, the kit may comprise reagents used for expressing the PCNA of the present invention. If necessary, the reagent kit containing the PCNA of the present invention may also contain other components and media which are generally used as biotechnology reagents.

EXAMPLES

The present invention will be described in more detail with reference to the following Examples, but the present invention is not limited to these Example at all.

1. Preparation of Pfu-PCNA and RFC Proteins

A Pfu-PCNA mutant protein preparation and an RFC protein preparation were prepared by expressing these genes in large amounts in *Escherichia coli* and purifying the proteins from those protein-expressing microbial cells.

1.1: Acquisition of Microbial Cells and Preparation of Genomic DNA 1.1.1: Acquisition of Pfu Microbial Cells and Preparation of Genomic DNA

*Pyrococcus.furiosus* DSM3638 strain was obtained from Deutsche Sammlung von Mikrooganismen und Zelkuluren GmbH (English name: German Collection of Microorganisms and Cell Cultures, address: Mascheroder Weg 1b, 38124 Braunschweig, Germany). The DSM3638 strain was cultured according to the method described in the reference (Uemori et al., Nucl. Acids Res. 21: 259-265 (1993)). About 1.2 g of microbial cells were obtained from 500 ml of cultured medium. These were suspended in 10 mL of buffer (10 mM Tris-Cl pH8.0, 1 mM EDTA, 100 mM NaCl), and 1 mL of 10% SDS was added. After stirring, 50 μL of proteinase K (20 mg/mL) was added and the mixture was left stand at 55° C. for 60 minutes. Subsequently, the reaction solution was extracted sequentially with phenol, phenol/chloroform and chloroform, and then ethanol was added to insolubilize DNA. The collected DNA was dissolved in 1 mL of TE solution (10 mL of Tris-Cl, pH 8.0, 1 mM EDTA), and 0.75 mg of RNase A was added to react at 37° C. for 60 minutes. Subsequently, the reaction solution was extracted again sequentially with phenol, phenol/chloroform and chloroform, and subsequently ethanol was added to collect the DNA.

1.2: Cloning of PCNA Gene

Figure 3:
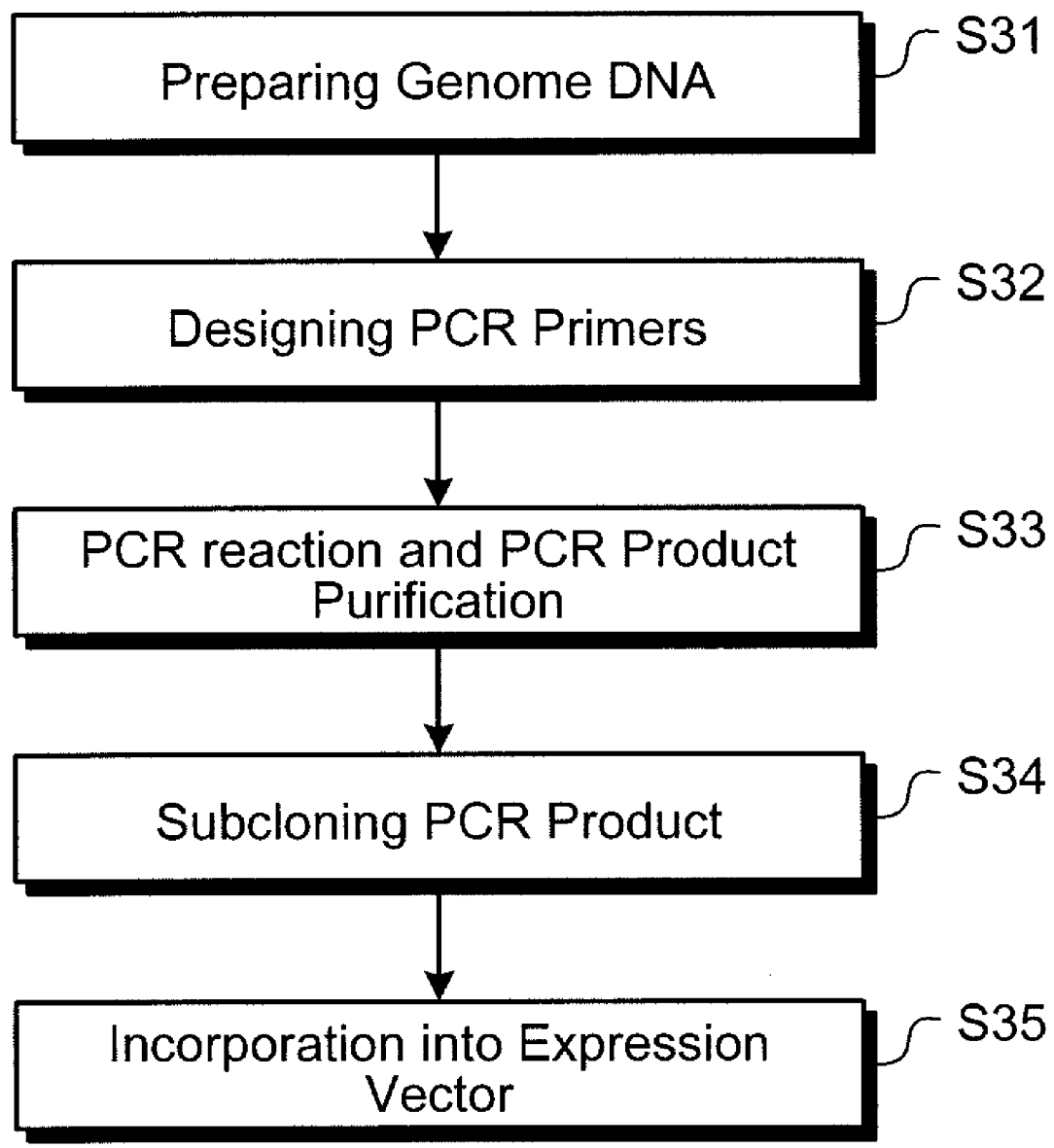
FIG. 3 is a view showing a flowchart for preparing an expression vector for a PCNA or RFC gene.

A Pfu-PCNA gene was acquired by cloning (FIG. 3) utilizing PCR with reference to the base sequence information AB 017486 (SEQ ID NOS: 1 and 2) registered in NCBI database. The detail thereof will be described below.

1.2.1: PCR Primer

Pfu-PCNA-F and Pfu-PCNA-R were used for the amplification of the pfu-PCNA gene. These sequences are designed so that a region corresponding to the region extending from an initiation codon methionine to a termination codon is amplified and further the sites recognized by the restriction enzymes NdeI and XhoI are added at a 5' side. The sequence of each primer was shown in Table 1 (SEQ ID NOS:3 and 4).

TABLE 1

Primers for amplification of PCNA gene

| name | Primer sequence 5'==>3' | SEQ ID NO |
|---|---|---|
| Pfu-PCNA-F | cat atg cca ttt gaa atc gta tt | 3 |
| Pfu-PCNA-R | ctc gag tca ctc ttc aac tct | 4 |

1.2.2: Template DNA

As the template for the PCR, the Pfu genomic DNA prepared in the aforementioned 1.1.1 was used.

1.2.3: Composition of PCR Reaction Solution

The PCR reaction solution has the following composition (amounts to be added to 50 μL of the reaction solution).

Template DNA: 100 ng,
Primers: each 10 pmol,
dNTP: each 10 nmol,
Ex Taq*: 1.25 U and
10× Ex Taq buffer: 5 μL were mixed, and sterilized water was added thereto up to the total volume of 50 μL.
(*supplied from TAKARA BIO INC.)

1.2.4.: Reaction Conditions for PCR

The PCR reaction was performed by using the reaction solution prepared in the aforementioned procedure and a PCR apparatus and using a program repeating 30 cycles of the reaction at 95° C. for 30 seconds-->55° C. for 30 seconds-->72° C. for one minute.

1.2.5: Purification of PCR Product

The PCR product obtained in the aforementioned procedure was subjected to 1% agarose gel electrophoresis, and stained with ethidium bromide. Subsequently a gel fragment containing a band around 800 bp was cut out under ultraviolet light irradiation, and the PCR product in the gel fragment was purified using GFX PCR DNA and Gel Band Purification kit (Amersham Bioscience) according to its manipulation manual.

1.2.6: Subcloning of PCR Product

The purified PCR product was ligated to pUC118-HincII/BAP using TaKaRa BKL kit (TAKARA BIO INC.) according to the manipulation manual. *Escherichia coli* DH5α (TAKARA BIO INC.) was transformed with this ligated PCR product, which was then seeded on an LB agar plate (containing 100 μg/mL of ampicillin, 40 μg/mL of IPTG, and 40 μg/mL of X-GAL), and cultured by leaving stand at 37° C. overnight to yield an *Escherichia coli* clone having the PCR product.

An *Escherichia coli* colony exhibiting white color on the agar plate was cultured in 3 mL of an LB liquid medium (containing 100 μg/mL of ampicillin) at 37° C. overnight with shaking, and then a plasmid DNA was prepared according to the standard method.

1.2.7: Confirmation of Sequence by Sequencing

Concerning the aforementioned plasmid DNA, the DNA sequence inserted into the recognition site of the restriction enzyme HincII in the plasmid vector pUC118 was examined using a DNA sequencer. As a result, it was confirmed that the open reading frame of the Pfu-PCNA gene was retained, the restriction enzyme NdeI recognition sequence was added to the 5' end and the restriction enzyme XhoI recognition sequence was added the 3' end in the inserted portion. This plasmid vector having the open reading frame of the pfu-PCNA gene was designated as pUC/PPC.

1.3: Preparation of PCNA Expression Plasmid

The plasmid pUC/PPC was doubly cleaved with restriction enzymes NdeI and XhoI to prepare a PCNA gene fragment. The gene fragment was inserted into an expression vector to produce the expression vector of Pfu-PCNA.

1.3.1: Preparation of PCNA DNA Fragment

The plasmid pUC/PPC was doubly cleaved with restriction enzymes NdeI and XhoI in the following reaction system.

Plasmid DNA: 5 μg
10× Restriction enzyme buffer: 5 μL
Restriction enzyme NdeI: 5 units
Restriction enzyme XhoI: 5 units Sterile water was added to the aforementioned mixture up to the total volume of 50 μL, and the plasmid DNA was cleaved with the restriction enzymes at 37° C. for 30 minutes. After completing the reaction, the reaction product was run on 2% agarose gel electrophoresis. A band (around about 800 bp) corresponding to the Pfu-PCNA gene was cut out and the PCNA DNA fragment was purified from the gel using GFX PCR DNA and Gel Band Purification kit (Amersham Bioscience) according to its manipulation manual.

1.3.2: pET-21a Expression Vector

A vector DNA pET-21a (Novagen, US) was doubly cleaved with the restriction enzymes NdeI and XhoI by the following reaction.

Plasmid DNA: 2 μg
10× Restriction enzyme buffer: 5 μL
Restriction enzyme NdeI: 5 units
Restriction enzyme XhoI: 5 units Sterile water was added to the aforementioned mixture up to the total volume of 50 μL, which was then left stand at 37° C. for 2 hours. After completing the reaction, the reaction product was run on 1% agarose gel electrophoresis. A band (around about 5.4 kb) corresponding to the straight form of the vector DNA pET-21a was cut out and the pET-21a DNA fragment was purified from the gel using GFX PCR DNA and Gel Band Purification kit (Amersham Bioscience) according to its manipulation manual.

1.3.3: Ligation Reaction and Transformation

The Pfu-PCNA DNA fragment (100 ng) and the pET-21a DNA fragment (50 ng) obtained in the aforementioned procedure were reacted using DNA Ligation Kit V2 (TAKARA BIO INC.) as follows.

PCNA DNA fragment: 100 ng
pET-21a DNA fragment: 50 ng
DNA Ligation Kit V2 enzyme solution: 5 μL Sterile water was added to the aforementioned mixture up to the total volume of 10 μL, which was then reacted at 16° C. for 30 minutes.

100 μL of *Escherichia coli* (*E. coli*) BL21 (DE3) (Novagen) was transformed with this ligation product (3 μL). The solution of transformed *E. coli* was seeded on the LB agar plate (100 μg/mL ampicillin) and left stand to culture at 37° C. overnight. Three colonies in *E. coli* colonies formed on the agar plate were cultured with shaking in 3 mL of the LB liquid medium (containing 100 μg/mL ampicillin) at 37° C. overnight, and a plasmid DNA was prepared according to standard methods.

1.3.4: Confirmation of Sequence by Sequencing

Concerning the aforementioned plasmid DNA, the DNA sequence inserted in the plasmid vector pET-21a and the sequence in the vicinity of the inserted site were examined using the DNA sequencer. As a result, the ORF (open reading frame) of the Pfu-PCNA gene was completely inserted between NdeI and XhoI sites which were multicloning sites. This plasmid retaining the Pfu-PCNA gene was designated as pPPCNA (FIG. 4).

Figure 4:
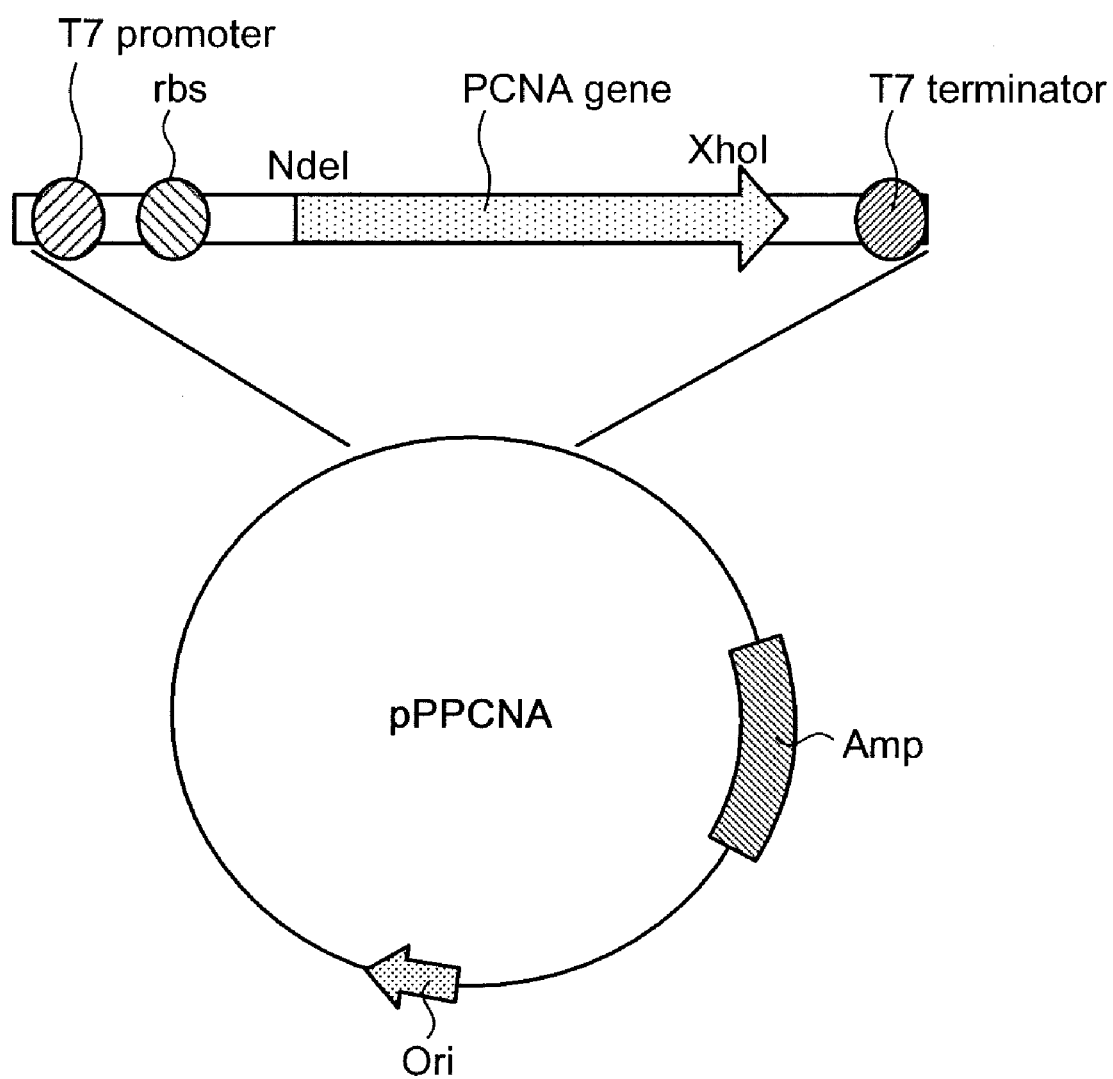
FIG. 4 is a view showing an expression plasmid for the PCNA gene.

As shown in FIG. 4, it was confirmed that a T7 promoter and rbs (ribosome binding site) which pET-21a had, the PCNA gene ORF (open reading frame) and a T7 terminator were aligned in this order in pPPCNA. It was expected that this plasmid would express the PCNA gene in a large amount.

1.4: Introduction of Mutation into PCNA Gene

For the purpose of producing the PCNA having a higher function, the amino acid in Pfu-PCNA was substituted. The amino acid was substituted by substituting the base in the codon encoding that amino acid. An amino acid mutation was introduced into a mutation site shown in Table 2.

TABLE 2

Mutation site in PCNA

| Mutant ID | Mutation site |
| --- | --- |
| Pfu-PCNA01 | M73L |
| Pfu-PCNA10 | M73L + D143A |
| Pfu-PCNA12 | M73L + R82C |
| Pfu-PCNA13 | M73L + D143R |
| Pfu-PCNA16 | M73L + R82C + D143R |
| Pfu-PCNA70 | M73L + D143K |
| Pfu-PCNA71 | M73L + D143H |
| Pfu-PCNA72 | M73L + R109E |
| Pfu-PCNA77 | M73L + D147R |
| Pfu-PCNA78 | M73L + E139A |
| Pfu-PCNA79 | M73L + E139R |

1.4.1: Introduction of Substitution Mutation

The mutation was introduced into the PCNA gene by utilizing the plasmid to be mutated, an oligo pair for mutation introduction (SEQ ID NOS:5 to 12 in Table 3) and Quick Change II Site-Directed Mutagenesis Kit (Stratagene) according to its manipulation manual.

TABLE 3

Oligo DNA sequence for introducing mutation into PCNA

| Primer name | Sequence 5'=>3' | SEQ ID NO |
| --- | --- | --- |
| Pfu_M73L-F | CA ATT GGA GTT AAC CTG GAC CAC CTA AAG | 5 |
| Pfu_M73L-R | CTT TAG GTG GTC CAG GTT AAC TCC AAT TG | 6 |
| Pfu_D143A-F | TT CTT GGA GAA GTC CTA AAA GCT GCT GTT AAA GAT GCC TCT CTA GTG AGT GAC AG | 7 |
| Pfu_D143A-R | CT GTC ACT CAC TAG AGA GGC ATC TTT AAC AGC AGC TTT TAG GAC TTC TCC AAG AA | 8 |
| Pfu_R82C-F | CCT AAA GAA GAT CCT AAA GTG CGG TAA AGC AAA GG | 9 |
| Pfu_R82C-R | CCT TTG CTT TAC CGC ACT TTA GGA TCT TCT TTA GG | 10 |
| Pfu_D143R-F | GGA GAA GTC CTA AAA CGT GCT GTT AAA GAT GCC | 11 |
| Pfu_D143R-R | GGC ATC TTT AAC AGC ACG TTT TAG GAC TTC TCC | 12 |
| Pfu_D143K-F | GGA GAA GTC CTA AAA AAA GCT GTT AAA GAT | 62 |
| Pfu_D143K-R | ATC TTT AAC AGC TTT TTT TAG GAC TTC TCC | 63 |
| Pfu_D143H-F | GGA GAA GTG CTA AAA CAT GCT GTT AAA GAT | 64 |
| Pfu_D143H-R | ATC TTT AAC AGC ATG TTT TAG GAC TTC TCC | 65 |
| Pfu_R109E-F | CAA GGA ACT GCA ACA GAA ACA TTT AGA GTT CCC C | 66 |
| Pfu-R109E-R | GGG AAC TCT AAA TGT TTC TGT TGC AGT TCC TTG | 67 |
| Pfu_D147R-F | CCT AAA AGA TGC TGT TAA AAG AGC CTC TCT AGT GAG TGA C | 68 |
| Pfu_D147R-R | GTC ACT CAC TAG AGA GGC TCT TTT AAC AGC ATC TTT TAG G | 69 |
| Pfu_E139A-F | GGT TGT AGT TCT TGG AGC AGT CCT AAA AGA TGC TG | 70 |
| Pfu_E139A-R | CAG CAT CTT TTA GGA CTG CTC CAA GAA CTA CAA CC | 71 |
| Pfu_E139R-F | GGT TGT AGT TCT TGG AAG AGT CCT AAA AGA TGC TG | 72 |
| Pfu_E139R-R | CAG CAT CTT TTA GGA CTC TTC CAA GAA CTA CAA CC | 73 |

After introducing the mutation, the DNA sequence was checked by sequencing to confirm that the mutation had been introduced into an objective site and no mutation other than the objective one was present. The design for each PCNA mutant will be described below.

1.4.1.1: Pfu-PCNA01

According to the report for the Pfu-PCNA (Non-patent Document 6), the following has been reported: when the natural Pfu-PCNA is prepared as the recombinant protein using *Escherichia coli* as the host, in addition to the original protein as a result of translation from Met, another protein of about 20 kDa with the N terminus beginning from the 73rd residue is produced as a byproduct. It is also reported that when Met at position 73 is substituted with Leu using the gene engineering technique, the production of this protein of about 20 kDa is inhibited. It has been further reported that the Pfu-PCNA produced in this way has the nature indistinguishable from the nature of the wild type PCNA protein. Based on these facts, the mutant Pfu_M73L is addressed as a quasi-wild type in the present specification.

This mutant Pfu_M73L was designated as Pfu-PCNA01, and this mutant was produced. Pfu-PCNA01 was produced using pPPCNA as a template plasmid and the oligo pair for introducing the mutation (Pfu_M73L-F and Pfu_M73L-R).

1.4.1.2: Pfu-PCNA10

Pfu-PCNA10 is a mutant obtained by a single residue substitution by substituting the amino acid D at position 143 with A in Pfu-PCNA01, and its structure and nature have been reported by Matsumiya (Non-patent Document 9). According to the report, aspartic acid at position 143 is located on the interface when the Pfu-PCNA forms the homotrimer and is a part of the amino acid residues involved in trimer formation. It is further reported that, when this aspartic acid at position 143 is substituted with alanine, the trimer formation is inhibited but stimulation itself to the DNA polymerase activity is kept.

This PCNA mutant having double mutations of D143A and M73L was designated as Pfu-PCNA10, and produced using the Pfu-PCNA01-producing plasmid as the template and oligos Pfu_D143A-F and Pfu_D143A-R for introducing the mutation.

1.4.1.3: Pfu-PCNA12

Pfu-PCNA12 is the mutant obtained by the single residue substitution by substituting the amino acid R at position 82 with C. According to Matsumiya (Non-patent Document 9), it has been reported that arginine at position 82 is located on the interface when the pfu-PCNA forms the homotrimer.

This PCNA mutant having the double mutations of R82c and M73L was designated as Pfu-PCNA12, and produced using the Pfu-PCNA01-producing plasmid as the template and oligos Pfu_R82C-F and Pfu_R82C-R for introducing the mutation.

1.4.1.4: Pfu-PCNA13

Pfu-PCNA 13, aiming at examining how intentional inhibition of PCNA trimer formability would affect on DNA replication, was prepared by substituting the residue at position 143 with arginine (basic amino acid), whereby the electric nature thereof became completely different from aspartic acid (acidic amino acid) in the quasi-wild type (Pfu-PCNA01) and alanine (neutral amino acid) in Pfu-PCNA10. Specifically, the mutant Pfu-PCNA13 was produced using the Pfu-PCNA01-producing plasmid as the template and oligos Pfu_D143R-F and Pfu_D143R-R for introducing the mutation.

1.4.1.5: Pfu-PCNA16

This mutant was produced aiming at examining the effect of substituting two amino acid residues that probably have close relationship with trimer formation, i.e., arginine at position 82 and aspartic acid at position 143. Specifically, the mutant Pfu-PCNA16 was produced using the Pfu-PCNA12-producing plasmid as the template and oligos Pfu_D143R-F and Pfu_D143R-R for introducing the mutation.

1.4.1.6: Pfu-PCNA70

For the purpose of comparing activities depending on the amino acid introduced into the position 143, this mutant was produced by substituting the amino acid at position 143 with lysine (basic amino acid). Even though both belong to the category of basic amino acid, guanidinium group in the side chain of arginine has a $pK_R$ value of 12.48 whereas butyl ammonium group in the side chain of lysine has a $pK_R$ value of 10.54. Thus lysine is less basic. The expression plasmid was produced using the Pfu-PCNA01-producing plasmid as the template and oligos Pfu_D143K-F and Pfu_D143K-R for introducing the mutation.

1.4.1.7: Pfu-PCNA71

For the purpose of comparing activities depending on the amino acid introduced into the position 143, this mutant was produced by substituting the amino acid at position 143 with histidine (basic amino acid). The side chain of histidine has the $pK_R$ value of 6.0 and is dissociated at physiological pH. At pH 6.0, 50% of imidazole group in histidine is charged and the remaining 50% is not charged. Thus, histidine becomes neutral at higher pH in the range of physiological pH. Therefore, it was anticipated that the amino acid to be introduced would exert a different nature from that of arginine and lysine. The expression plasmid was produced using the Pfu-PCNA01-producing plasmid as the template and oligos Pfu_D143H-F and Pfu_D143H-R for introducing the mutation.

1.4.1.8: Pfu-PCNA72

The mutant was produced by substitution with glutamic acid (acidic amino acid) of arginine (basic amino acid) at position 109, which is one of amino acids located on the interface when the Pfu-PCNA forms the homotrimer and involved in the trimer formation. The expression plasmid was produced using the Pfu-PCNA01-producing plasmid as the template and oligos Pfu_R109E-F and Pfu_R109E-R for introducing the mutation.

Pfu-PCNA77

The mutant was produced by substitution with arginine (basic amino acid) of aspartic acid (acidic amino acid) at position 147, which is one of the amino acids located on the interface when the Pfu-PCNA forms the homotrimer and involved in the trimer formation. The expression plasmid was produced using the Pfu-PCNA01-producing plasmid as the template and oligos Pfu_D147R-F and Pfu_D147R-R for introducing the mutation.

1.4.1.10: Pfu-PCNA78

The mutant was produced by substitution with alanine (neutral amino acid) of glutamic acid (acidic amino acid at position 139, which is one of the amino acids located on the interface when the Pfu-PCNA forms the homotrimer and involved in the trimer formation. The expression plasmid was produced using the Pfu-PCNA01-producing plasmid as the template and oligos Pfu_E139A-F and Pfu_E139A-R for introducing the mutation.

1.4.1.11: Pfu-PCNA79

The mutant was produced by substitution with arginine (basic amino acid) of glutamic acid (acidic amino acid) at position 139, which is one of the amino acids located on the interface when the Pfu-PCNA forms the homotrimer and involved in the trimer formation. The expression plasmid was produced using the Pfu-PCNA01-producing plasmid as the template and oligos Pfu_E139R-F and Pfu_E139R-R for introducing the mutation.

1.4.2: Production of Expression Strain

*Escherichia coli* BL21 CodonPlus (DE3) RIL (Stratagene) was transformed with the plasmid vectors for expressing the mutant PCNA obtained in the aforementioned procedure, to yield *E. coli* strains each expressing mutant gene.

1.4.3: Culturing of Microbial Cells and Induction of Expression

Each mutant PCNA expression strain was cultured in 1.5 Liters of the LB medium (containing 50 μg/mL of ampicillin) at 37° C. with shaking. The expression was induced by adding IPTG (isopropyl-β-D-thiogalactopyranoside) at a final concentration of 0.1 mM when $OD_{600}$ at a logarithmic growth phase was 0.3 to 0.5, and after inducing the expression, the culturing after the induction was continued for about 3 hours. Microbial cells after the culturing were collected by centrifugation (4° C., 6,000×g, 6 minutes).

1.4.4: Purification of PCNA Protein (FIG. 5)

Figure 5:
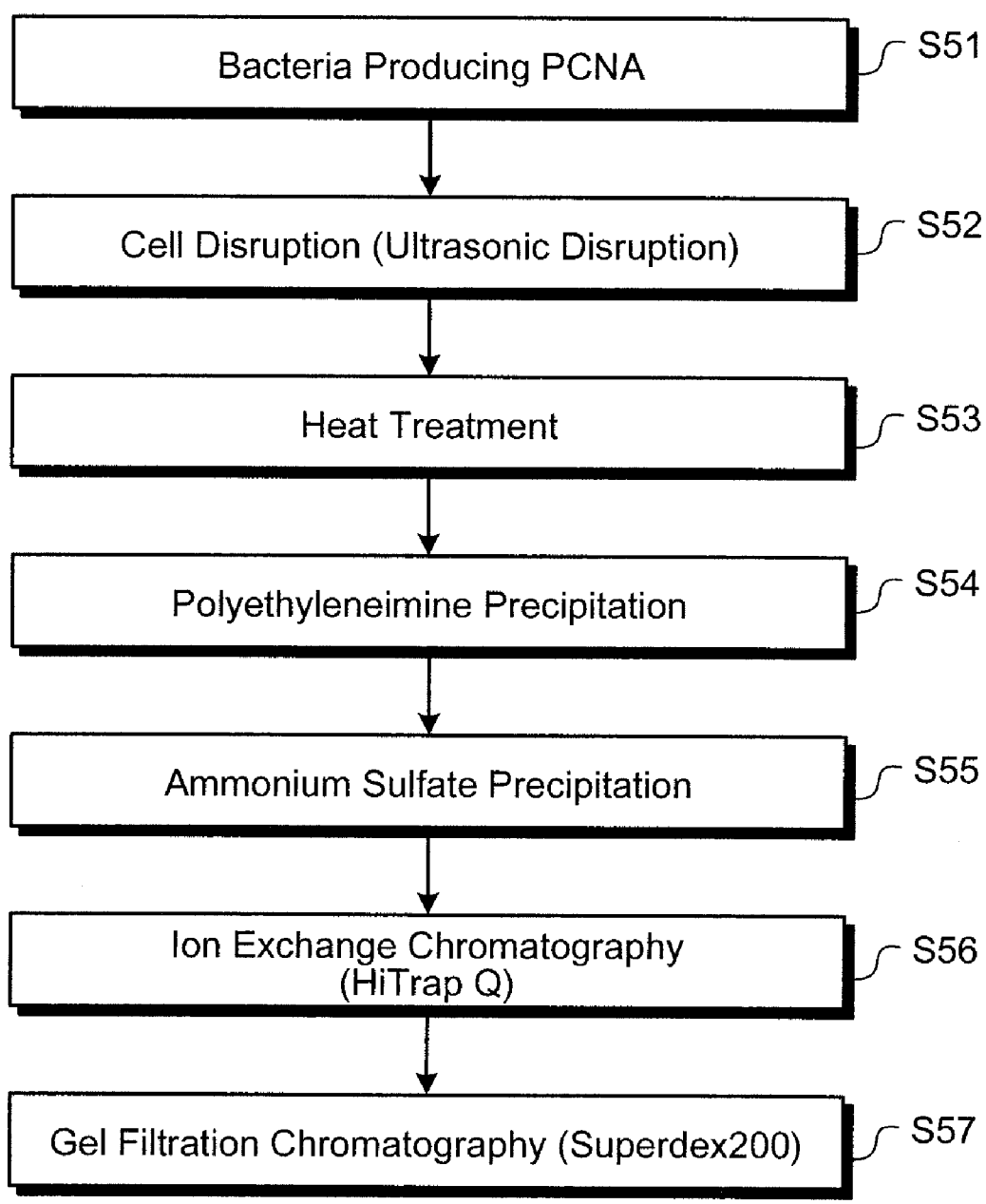
FIG. 5 is a view showing a flowchart for preparing PCNA (protein).

As shown in FIG. 5, a preparation was obtained by collecting the microbial cells by centrifugation (S51), disrupting the microbial cells (ultrasonic disruption, S52), boiling for 5 minutes (S53), performing polyethyleneimine precipitation (S54), performing ammonium sulfate precipitation (S55), performing ion exchange chromatography (S56, using HiTrap Q as a column) and performing gel filtration chromatography (S57, using Superdex 200). It was confirmed by SDS-PAGE that the protein was purified well.

1.4.1.1: Disruption of Microbial Cells

The microbial cells precipitated by centrifugation were suspended in 25 mL of buffer A (50 mM Tris-HCl pH8.5, 0.1 M NaCl, 2 mM 2-mercaptoethanol, 10% glycerol) or buffer B (50 mM Tris-HCl pH8.0, 0.1 M NaCl, 0.1 mM EDTA, 10% glycerol, 0.5 mM DTT). The microbial cells were disrupted by ultrasonic treatment.

1.4.4.2: Treatment with Heat

A disrupted microbial cell suspension was boiled for 5 minutes and then centrifuged (18,500×g, 4° C., 25 minutes), to collect a supernatant.

1.4.4.3: Polyethyleneimine Precipitation

Polyethyleneimine (Sigma P-3143) and NaCl at final concentrations of 0.2% (w/v) and 0.58 M, respectively, were added to the supernatant, which was then stirred on ice for 30 minutes. This solution was centrifuged (18,500×g, 4° C., 25 minutes) to yield the supernatant.

1.4.4.4: Ammonium Sulfate Precipitation 5.61 g of ammonium sulfate (final concentration of 80%) was added to 10 mL of the supernatant and stirred on ice for 30 minutes to precipitate a protein. 80 mL of 50 mM Tris-HCl (pH 8.5) buffer in which ammonium sulfate had been 80% saturated was added to this solution and a precipitation was collected by centrifugation (30,000×g, 4° C., 25 minutes). Subsequently, this precipitation was dissolved in buffer C (50 mM Tris-HCl pH 8.0, 0.1 M NaCl) and the resulting solution was dialyzed against the same buffer C.

1.4.4.5: Ion Exchange Chromatography

A dialyzed sample was applied on an ion exchange chromatography (HiTrap Q: Amersham Bioscience) using FPLC protein purification system (Amersham Bioscience) for Pfu-PCNA01, 10, 12, 13 and 16, and AKTA explorer 10S (Amersham Bioscience) for other Pfu-PCNA70, 71, 72, 77, 78 and 79. Elution was performed with a linear gradient of 0.1 to 0.8 M NaCl/17.5 mL, and a flow rate was 1 mL/minute.

1.4.4.6: Gel Filtration Chromatography

The peak fraction in the HiTrap Q ion exchange chromatography was further purified by gel filtration chromatography using Superdex 200 (Amersham Bioscience) to obtain a preparation for subsequent assays.

Figure 6:
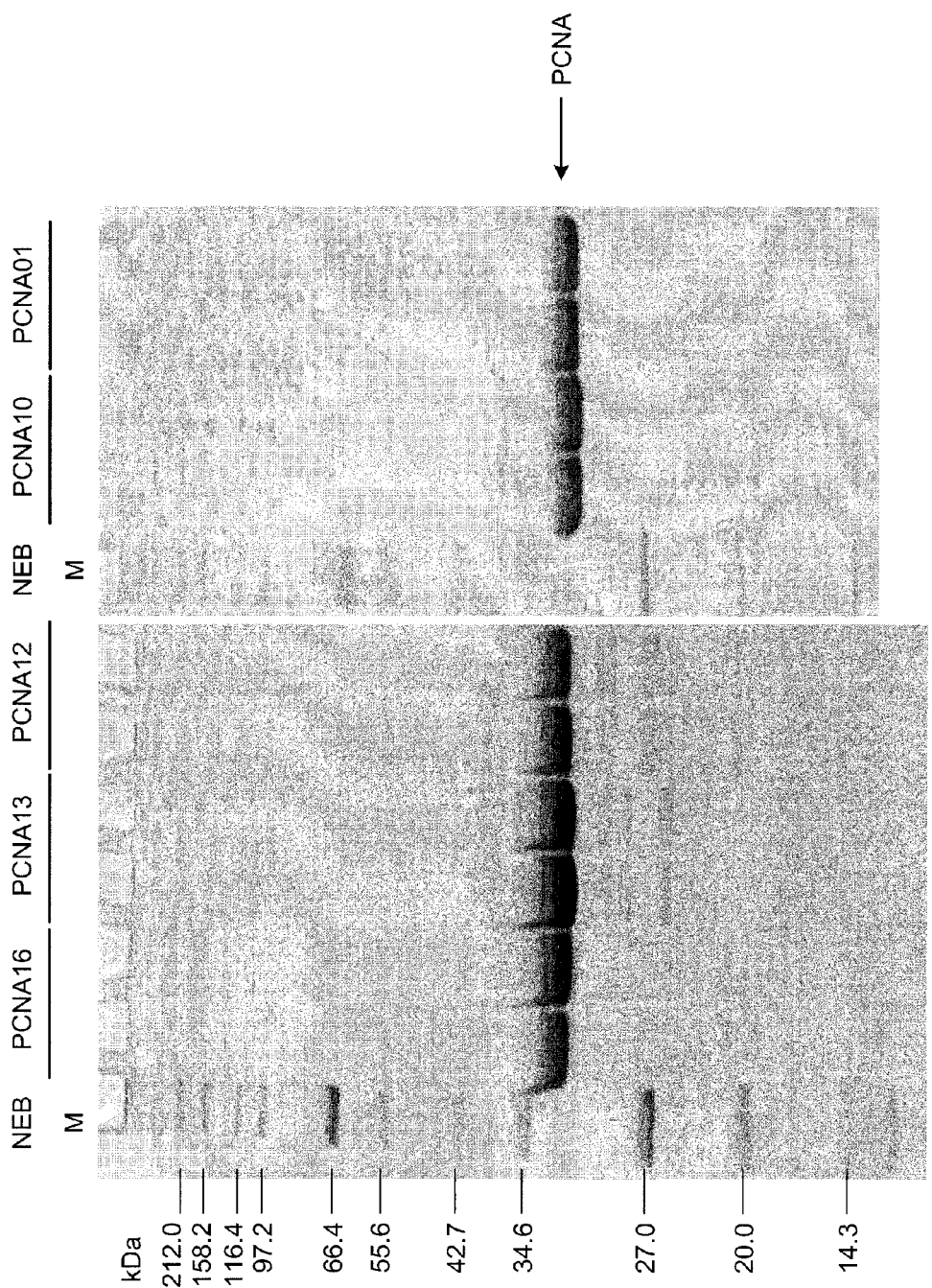
FIG. 6 is a view showing a result of polyacrylamide gel electrophoresis of a PCNA protein preparation.
Figure 40:
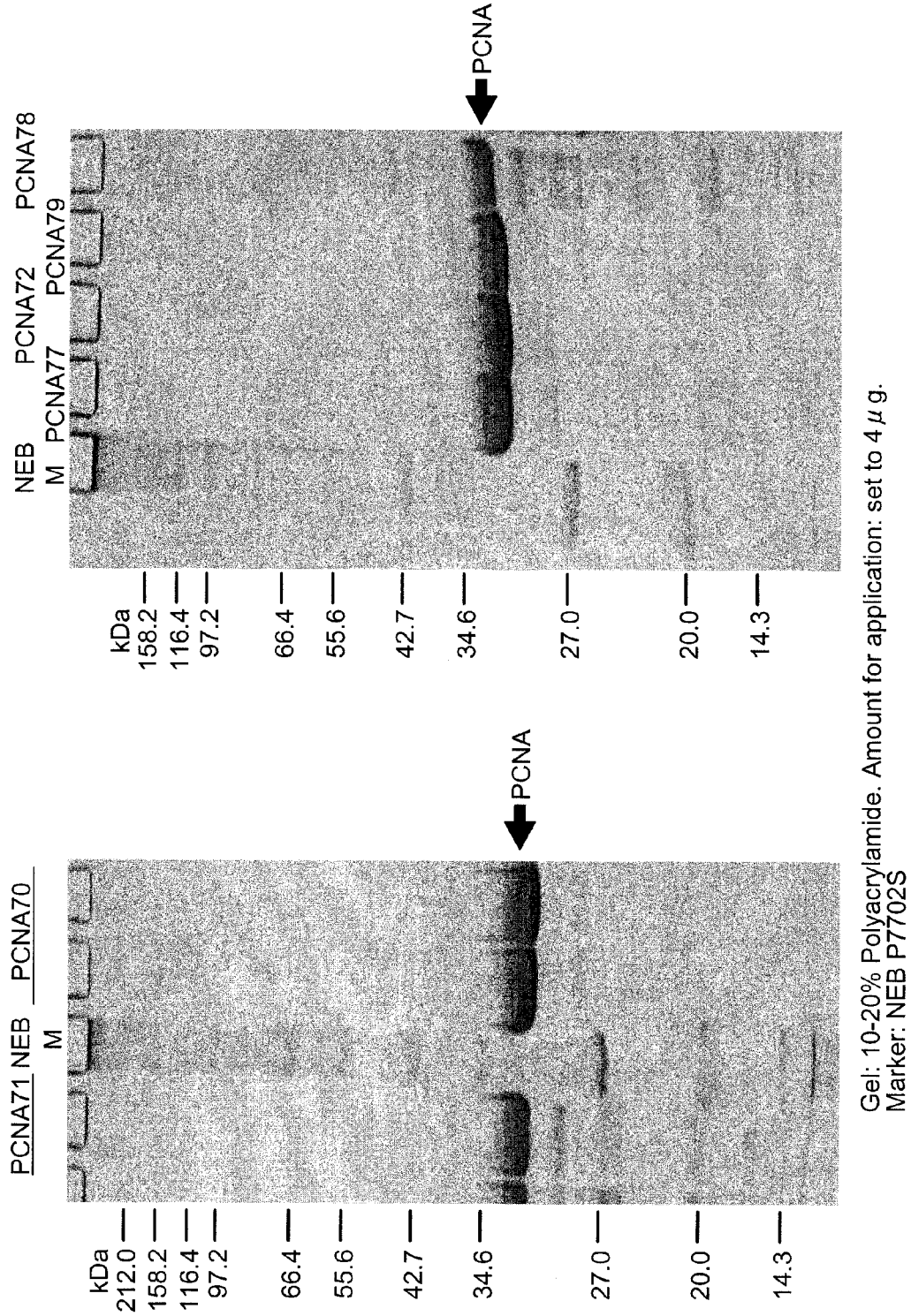
FIG. 40 is a view showing a result of polyacrylamide gel electrophoresis of a PCNA protein preparation.

The obtained preparation was applied on polyacrylamide gel electrophoresis to confirm its molecular size and good purification (FIGS. 6 and 40). 1.5: Cloning of Pfu-RFC gene RFC is composed of two subunits RFCL and RFCS, which are located in tandem on the genome of *Pyrococcus furiosus*. Upon producing an RFC protein preparation, an RFCL gene and an RFCS gene were individually introduced in distinct expression vectors, the respective expression vectors were introduced into the same host and the genes were expressed simultaneously. The expression plasmids were produced with reference to Non-patent Document 7. The detail thereof will be described below.

1.5.1: Cloning of RFCL Gene and Preparation of Expression Plasmid

A Pfu-RFCL gene (NCBI Gene ID 1467921) was obtained by PCR using the Pfu genome as the template (base sequence: SEQ ID NO:13, amino acid sequence: SEQ ID NO:14). RFCL-F and RFCL-R primers were used as the primers for PCR (SEQ ID NOS 15 and 16 in Table 4). For convenience of cloning, a restriction enzyme NdeI recognition site was added to the RFCL-F primer and a XhoI recognition site was added to the RFCL-R primer.

TABLE 4

Primers for amplification of RFCL gene

| Primer name | Primer sequence 5'==>3' | SEQ ID NO |
|---|---|---|
| RFCL-F Primer | AGC CAT ATG CCA GAG CTT CCC TGG GTA GAA | 15 |
| RFCL-R Primer | AGC TCG AGT CAC TTT TTA AGA AAG TCA AAG AGA G | 16 |

The Pfu genomic DNA prepared in the aforementioned 1.1 was used as the template for PCR.

The PCR reaction solution has the following composition (amounts to be added to 50 μL of the reaction system).

Template DNA: 100 ng,
Primers: each 10 pmol,
dNTP: each 10 nmol,
Ex Taq*: 1.25 U and
10× Ex Taq buffer: 5 μL were mixed, and sterilized water was added thereto up to the total volume of 50 μL.

(*supplied from TAKARA BIO INC.)

1.5.1.1: Reaction Conditions for PCR

The PCR reaction was performed by using the reaction solution prepared in the aforementioned procedure, using the PCR apparatus and using the program repeating 30 cycles of the reaction at 95° C. for 30 seconds-->55° C. for 30 seconds-->72° C. for one minute.

1.5.1.2: Purification of PCR Product

The PCR product obtained in the aforementioned procedure was subjected to 1% agarose gel electrophoresis, and stained with ethidium bromide. Subsequently a gel fragment containing a band around 1.4 kb was cut out under the ultraviolet light irradiation, and the PCR product in the gel fragment was purified using GFX PCR DNA and Gel Band Purification kit (Amersham Bioscience) according to its manipulation manual.

1.5.1.3: Subcloning of PCR Product

The purified PCR product was ligated to pUC118-HincII/BAP (TAKARA BIO INC.) using TaKaRa BKL kit (TAKARA BIO INC.) according to the manipulation manual. *Escherichia coli* DH5α (TAKARA BIO INC.) was transformed with this ligated PCR product, which was then seeded on the LB agar plate (containing 100 μg/mL of ampicillin, 40 μg/mL of IPTG, and 40 μg/mL of X-GAL), and cultured by leaving stand at 37° C. overnight to yield an *Escherichia coli* clone having the PCR product.

An *Escherichia coli* colony exhibiting the white color on the agar plate was cultured in 3 mL of the LB liquid medium (containing 100 μg/mL of ampicillin) at 37° C. overnight with shaking, and then a plasmid DNA was prepared according to the standard method.

1.5.1.4: Confirmation of Sequence by Sequencing

Concerning the aforementioned plasmid DNA, the DNA sequence inserted into the recognition site of the restriction enzyme HincII in the plasmid vector pUC118 was examined using the DNA sequencer. As a result, it was confirmed that the open reading frame of the Pfu-RFCL gene is retained, the restriction enzyme NdeI recognition sequence was added to the 5' end and the restriction enzyme XhoI recognition sequence was added to the 3' end in the inserted portion. This plasmid was designated as pUC118/RFCL.

1.5.1.5: Preparation of RFCL Expression Plasmid

The plasmid pUC118/RFCL was doubly cleaved with the restriction enzymes NdeI and XhoI to prepare an RFCL gene fragment. The gene fragment was inserted into the expression vector to produce the expression vector for Pfu-RFCL.

1.5.1.6: Preparation of RFCL DNA Fragment

The plasmid pUC118/RFCL was doubly cleaved with the restriction enzymes NdeI and XhoI in the following reaction system.

Plasmid DNA: 5 μg
10× Restriction enzyme buffer: 5 μL
Restriction enzyme NdeI: 5 units
Restriction enzyme XhoI: 5 units Sterile water was added to the aforementioned mixture up to the total volume of 50 μL, and the plasmid DNA was cleaved with the restriction enzymes at 37° C. for 2 hours. After completing the reaction, the reaction product was run on 1% agarose gel electrophoresis. A band (around about 1.4 kb) corresponding to the Pfu-RFCL gene was cut out and the RFCL DNA fragment was purified from the gel using GFX PCR DNA and Gel Band Purification kit (Amersham Bioscience) according to its manipulation manual.

1.5.1.7: pET-29a Expression Vector

The vector DNA pET-29a (Novagen, US) was doubly cleaved with the restriction enzymes NdeI and XhoI by the following reaction.

Plasmid DNA: 2 µg
10× Restriction enzyme buffer: 5 µL
Restriction enzyme NdeI: 5 units
Restriction enzyme XhoI: 5 units Sterile water was added to the aforementioned mixture up to the total volume of 50 µL, which was then left stand at 37° C. for 2 hours. After completing the reaction, the reaction product was run on 1% agarose gel electrophoresis. A band (around about 5.4 kb) corresponding to the straight form of pET-29a vector was cut out and the pET-29a DNA fragment was purified from the gel using GFX PCR DNA and Gel Band Purification kit (Amersham Bioscience) according to its manipulation manual.

1.5.1.8: Ligation Reaction and Transformation

The Pfu-RFCL DNA fragment (100 ng) and the pET-29a DNA fragment (50 ng) obtained in the aforementioned procedure were reacted using DNA Ligation Kit V2 (TAKARA BIO INC.) as follows.

RFCL DNA fragment: 100 ng
pET-29a DNA fragment: 50 ng
DNA Ligation Kit V2 enzyme solution: 5 µL Sterile water was added to the aforementioned mixture up to the total volume of 10 µL, which was then reacted at 16° C. for 30 minutes.

100 µL of *Escherichia coli* (*E. coli*) BL21 (DE3) (Novagen) was transformed with this ligation product (3 µL). The solution of transformed *E. coli* was seeded on the LB agar plate (containing 30 µg/mL of kanamycin) and left stand to culture at 37° C. overnight. Three colonies in *E. coli* colonies formed on the agar plate were cultured with shaking in 3 mL of the LB liquid medium (containing 30 µg/mL of kanamycin) at 37° C. overnight, and a plasmid DNA was prepared according to standard methods.

1.5.1.9: Confirmation of Sequence by Sequencing

Concerning the aforementioned plasmid DNA, the DNA sequence inserted in the plasmid vector pET-29a and the sequence in the vicinity of the inserted site were examined using DNA sequencer. As a result, the ORF (open reading frame) of the Pfu-RFCL gene was completely inserted between NdeI and XhoI sites which were in the multicloning site. The plasmid retaining this Pfu-RFCL gene was designated as pRFCL (FIG. 7).

Figure 7:
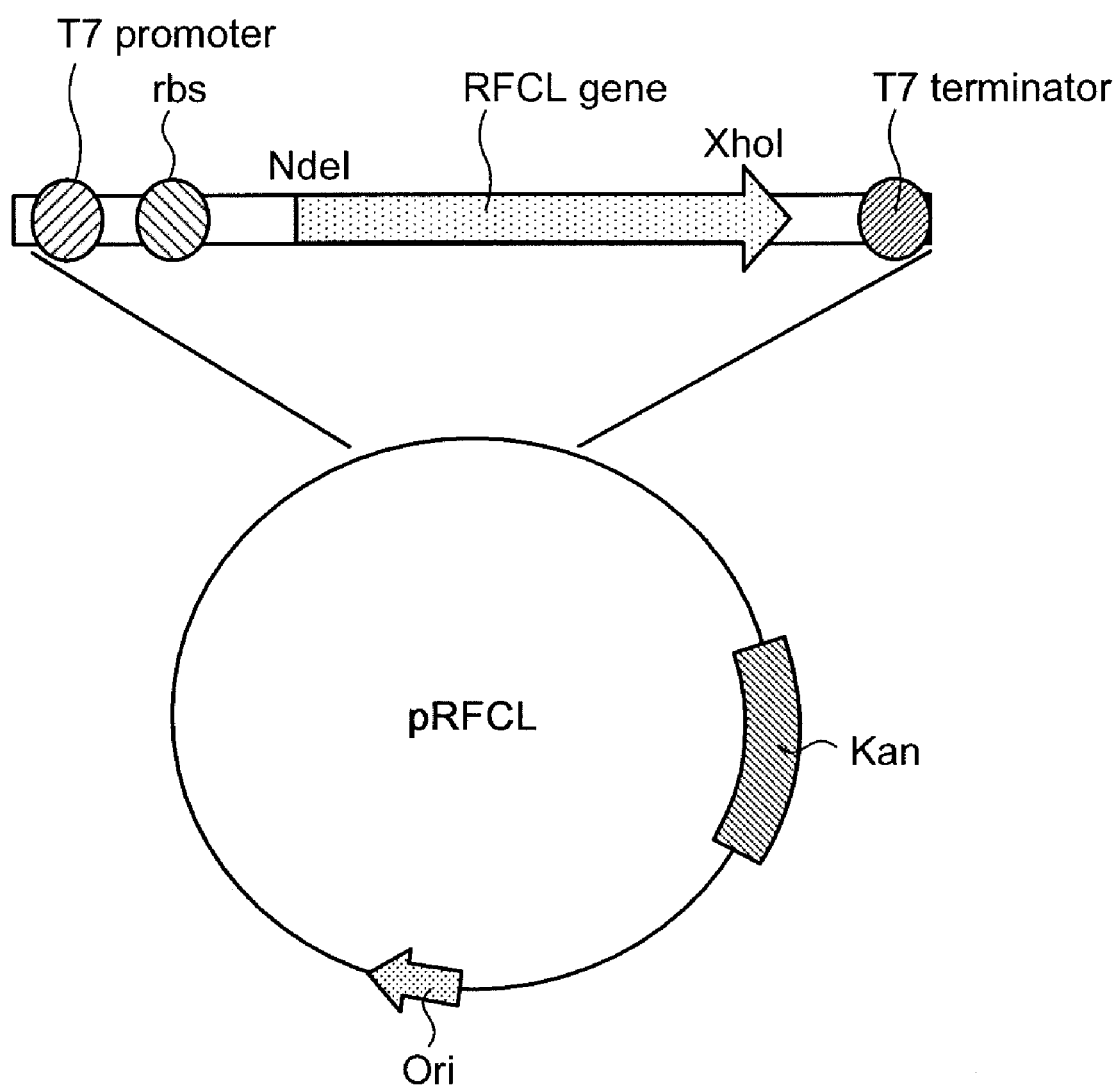
FIG. 7 is a view showing an expression plasmid for RFCL.

As shown in FIG. 7, it was confirmed that the T7 promoter and rbs (ribosome binding site) which pET-29a had, the RFCL gene ORF (open reading frame) and the T7 terminator were aligned in this order in pRFCL. It was expected that this plasmid would express the RFCL gene in the large amount.

1.5.2: Cloning of RFCS Gene and Preparation of Expression Plasmid

According to Non-patent Document 7, it has been reported that a pfu-RFCS gene (Gene ID: 1467922) has one intein (encoded by 1,575 bases) and an N terminal extein is encoded by 177 bases and a C terminal extein is encoded by 804 bases (initiation and termination codons are not included). The base sequence and the amino acid sequence of the Pfu-RFCS are shown in SEQ ID NOS:17 and 18, respectively (both include the intein portion).

When the RFCS expression vector was produced, first, full length of the Pfu-RFCS gene including the intein was amplified by PCR, and subsequently a mature RFCS (also referred to as RFCSm) was prepared by removing the intein. The intein was removed by amplifying the N terminal extein and the C terminal extein individually by PCR and fusing two extein fragments by PCR reaction.

1.5.2.1: PCR Reaction of RFCS Gene Including Intein

The PCR reaction was performed with the combination of the Pfu genomic DNA (prepared in the aforementioned 1.1), RFCS-F and RFCS-R primers (SEQ ID NOS:19 and 20 in Table 5).

TABLE 5

Primers for RFCS gene

| Primer name | Primer sequence 5'==>3' | SEQ ID NO |
|---|---|---|
| RFCS-F primer | ATG AGC GAA GAG ATT AGA GAA GTT | 19 |
| RFCS-R primer | ATC ACT TCT TCC CAA TTA GGG TGA AC | 20 |
| RFCSF1 primer | TCA TAT GAG CGA AGA GAT TAG AGA AGT TAA G | 21 |
| RFCSF2 primer | GCA GGC CCC CCT GGT GTC GGA AAG ACT ACA GCG GCT TTG GCC CTT G | 22 |
| RFCSR2 primer | CAA GGG CCA AAG CCG CTG TAG TCT TTC CGA CAC CAG GGG GGC CTG | 23 |
| RFCSR1 primer | AGG TCG ACC ATC ACT TCT TCC CAA TTA GGG TGA AC | 24 |

The PCR reaction solution has the following composition (amounts to be added to 50 µL of the reaction solution).

Template DNA: 100 ng,
Primers: each 10 pmol,
dNTP: each 10 nmol,
Ex Taq*: 1.25 U and
10× Ex Taq buffer: 5 µL were mixed, and sterilized water was added thereto up to the total volume of 50 µL.
(*supplied from TAKARA BIO INC.)

1.5.2.2: Reaction Conditions for PCR

The PCR reaction was performed by using the reaction solution prepared in the aforementioned procedure, using the PCR apparatus and using the program repeating 30 cycles of the reaction at 95° C. for 30 seconds-->55° C. for 30 seconds-->72° C. for one minute.

1.5.2.3: Purification of PCR Product

The PCR product obtained in the aforementioned procedure was subjected to 1% agarose gel electrophoresis, and stained with ethidium bromide. Subsequently a gel fragment containing a band around 2.6 kb was cut out under the ultraviolet light irradiation, and the PCR product in the gel fragment was purified using GFX PCR DNA and Gel Band Purification kit (Amersham Bioscience) according to its manipulation manual.

1.5.2.4: Subcloning of PCR Product

The purified PCR product was ligated to pUC118-HincII/BAP using TaKaRa BKL kit (TAKARA BIO INC.) according to the manipulation manual. *Escherichia coli* DH5α (TAKARA BIO INC.) was transformed with this ligated PCR product, which was then seeded on the LB agar plate (containing 100 µg/mL of ampicillin, 40 µg/mL of IPTG, and 40 µg/mL of X-GAL), and cultured by leaving stand at 37° C. overnight to yield an *Escherichia coli* clone having the PCR product.

An *Escherichia coli* colony exhibiting the white color on the agar plate was cultured in 3 mL of the LB liquid medium (containing 100 µg/mL of ampicillin) with shaking at 37° C. overnight, and then a plasmid DNA was prepared according to the standard method.

1.5.2.5: Confirmation of Sequence by Sequencing

Concerning the aforementioned plasmid DNA, the DNA sequence inserted into the recognition site of the restriction enzyme HincII in the plasmid vector pUC118 was examined using the DNA sequencer. As a result, the inserted fragment conformed to the Pfu-RFCS gene including the intein. This plasmid was designated as pUC/RFCS.

1.5.2.6: Primers for Amplifying Exteins

RFCSF1 primer and RFCSR2 primer (SEQ ID NOS:21 and 23 in Table 5) were prepared as the PCR primers for the N terminal extein. RFCSF2 primer and RFCSR1 primer (SEQ ID NOS:22 and 24 in Table 5) were prepared as the PCR primers for the C terminal extein. For the purpose of performing the cloning easily, the restriction enzyme NdeI sequence was added to the 5' end of the RFCSF1 primer and the restriction enzyme SalI sequence was added to the 5' end of the RFCSR1 primer. Complementary sequences utilized when two extein fragments were fused by the PCR reaction were provided in the RFCSF2 primer and the RFCSR2 primer.

The PCR reaction for amplifying two exteins was performed using the following composition (amounts to be added to 50 µL of the reaction solution).
  puC/RFCS DNA: 100 ng,
  Primers: each 10 pmol,
  dNTP: each 10 nmol,
  Ex Taq*: 1.25 U and
  10× Ex Taq buffer: 5 µL
were mixed, and sterilized water was added thereto up to the total volume of 50 µL.
(*supplied from TAKARA BIO INC.)

1.5.2.7: Reaction Conditions for PCR

The PCR reaction was performed by using the reaction solution prepared in the aforementioned procedure, using the PCR apparatus and using the program repeating 30 cycles of the reaction at 95° C. for 30 seconds-->55° C. for 30 seconds-->72° C. for one minute.

1.5.2.8: Purification of PCR Product

The PCR product obtained in the aforementioned procedure was subjected to 2% agarose gel electrophoresis and stained with ethidium bromide. A band of about 180 bases and a band of about 800 bases were observed in the PCR products from the primer set of RFCSF1 and RFCSR2 and the primer set of RFCSF2 and RFCSR1, respectively. The gel fragment including each band was cut out under the ultraviolet light irradiation, and the PCR product in the gel fragment was purified using GFX PCR DNA and Gel Band Purification Kit (Amersham Bioscience) according to its manipulation manual.

1.5.2.9: PCR Fusion Reaction

Two extein PCR products were fused by subjecting the two fragments to the PCR reaction with one set of primers in one tube to yield a gene fragment encoding the mature RFCS. The detail thereof will be described below.

An annealing reaction of two extein PCR products was performed with the following composition.
  N terminal extein fragment: 2 µL (corresponding to 50 ng),
  C terminal extein fragment: 2 µL (corresponding to 50 ng) and
  10× Ex Taq buffer: 5 µL.
Sterile water was added to the aforementioned composition up to the total volume of 44.5 µL.
The aforementioned mixture was heated at 95° C. for 3 minutes, and slowly cooled down to 37° C. over 30 minutes.

The followings were added to the aforementioned reaction solution.
  dNTP: 5 µL (each 10 nmol) and
  Ex Taq*: 0.5 µL (2.5 U).
The mixture was reacted at 72° C. for 10 minutes.
(*supplied from TAKARA BIO INC.)

Each 10 pmol of the RFCSF1 primer and the RFCSR1 primer were added to the aforementioned mixture, and the PCR reaction was performed using the program repeating 30 cycles of the reaction at 95° C. for 30 seconds-->55° C. for 30 seconds-->72° C. for one minute.

1.5.2.10: Cleavage with Restriction Enzymes and Purification of PCR Product

The aforementioned PCR product was purified by ethanol precipitation according to the standard method. The purified DNA fragment was doubly cleaved with the restriction enzymes NdeI and SalI.
  PCR product: corresponding to 1 µg
  10× Restriction enzyme buffer: 5 µL
  Restriction enzyme NdeI: 5 units
  Restriction enzyme SalI: 5 units
Sterile water was added to the aforementioned composition up to the total volume of 50 µL, and the PCR product was cleaved with the restriction enzymes at 37° C. for 2 hours. After completing the reaction, the reaction product was run on 2% agarose gel electrophoresis. A band (around about 1 kb) supposed to contain the fused fragment of two inteins (encoding the mature RFCS) was cut out, and the fragment was purified using GFX PCR DNA and Gel Band Purification Kit (Amersham Bioscience).

1.5.2.11: Cleavage of Expression Vector pET-21a with Restriction Enzymes

The vector DNA pET-21a (Novagen) was doubly cleaved with the restriction enzymes NdeI and SalI.
  Plasmid DNA: 2 µg
  10× Restriction enzyme buffer: 5 µL
  Restriction enzyme NdeI: 5 units
  Restriction enzyme SalI: 5 units
Sterile water was added to the aforementioned mixture up to the total volume of 50 µL, which was then left stand at 37° C. for 2 hours. After completing the reaction, the reaction product was run on 1% agarose gel electrophoresis. A band (around about 5.4 kb) corresponding to the straight form of the vector pET-21a was cut out and the pET-21a DNA fragment was purified from the gel using GFX PCR DNA and Gel Band Purification Kit (Amersham Bioscience) according to its manipulation manual.

1.5.2.12: Ligation Reaction and Transformation

The DNA fragment of about 1 kb (100 ng) predicted to be the fused fragment of two inteins (encoding the mature RFCS) and the pET-21a DNA fragment (50 ng) obtained in the aforementioned procedure were reacted using DNA Ligation Kit V2 (TAKARA BIO INC.) as follows.
  1 kb DNA fragment: 100 ng
  pET-21a DNA fragment: 50 ng
  DNA Ligation Kit V2 enzyme solution: 5 µL
Sterile water was added to the aforementioned mixture up to the total volume of 10 µL, which was then reacted at 16° C. for 30 minutes.

100 µL of *Escherichia coli* (*E. coli*) BL21 (DE3) (Novagen) was transformed with this ligation product (3 µl) The solution of *E. coli* was seeded on the LB agar plate (containing 100 µg/mL of ampicillin) and left stand to culture at 37° C. overnight. Three colonies in *E. coli* colonies formed on the agar plate were cultured with shaking in 3 mL of the LB liquid medium (containing 100 μg/mL of ampicillin) at 37° C. overnight, and a plasmid DNA was prepared according to standard methods.

1.5.2.13: Confirmation of Sequence by Sequencing

Concerning the aforementioned plasmid DNA, the DNA sequence inserted in the plasmid vector pET-21a and the sequence in the vicinity of the inserted site were examined using the DNA sequencer. As a result, the sequence of mature RFCSm (984 bases) without intein was identified between NdeI site and SalI site in the multicloning site (designated as pRFCSm).

Figure 8:
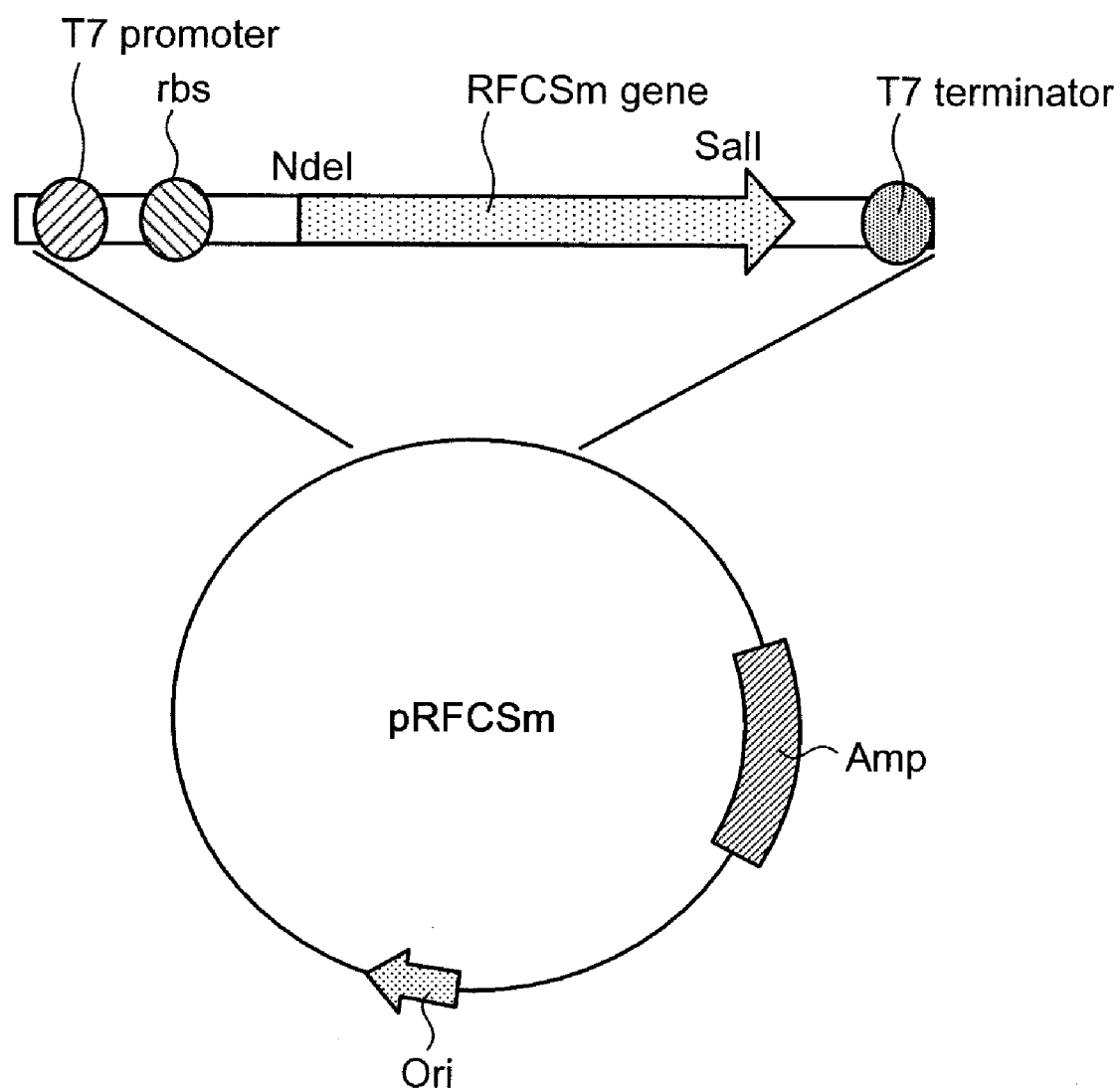
FIG. 8 is a view showing an expression plasmid for RFCSm.

As shown in FIG. 8, it was confirmed that the T7 promoter and rbs (ribosome binding site) which pET-21a had, the mature RFCS gene ORF (open reading frame) and the T7 terminator were aligned in this order in pRFCSm. It was expected that this plasmid would express the mature RFCS gene in the large amount.

1.6: Production of Pfu-RFC Gene Expression Strain

*Escherichia coli* BL21-CodonPlus (DE3)-RIL was simultaneously transformed with pRFCL and pRFCSm, and a Pfu-RFC expression strain was obtained by selecting the transformant having both plasmids doubly with ampicillin and kanamycin.

1.7: Expression of Pfu-RFC Gene

The aforementioned expression strain was cultured with shaking in 1.5 liters of the LB medium (containing 50 μg/mL of ampicillin and 30 μg/mL of kanamycin) at 37° C. The expression was induced by adding IPTG (isopropyl-β-D-thiogalactopyranoside) at a final concentration of 0.1 mM when $OD_{600}$ at the logarithmic growth phase was 0.3 to 0.5, and after inducing the expression, the culturing was continued for about 3 hours. Microbial cells after the culturing were collected by centrifugation (4° C., 6,000×g, 6 minutes).

1.8: Purification of Pfu-RFC Protein

Figure 9:
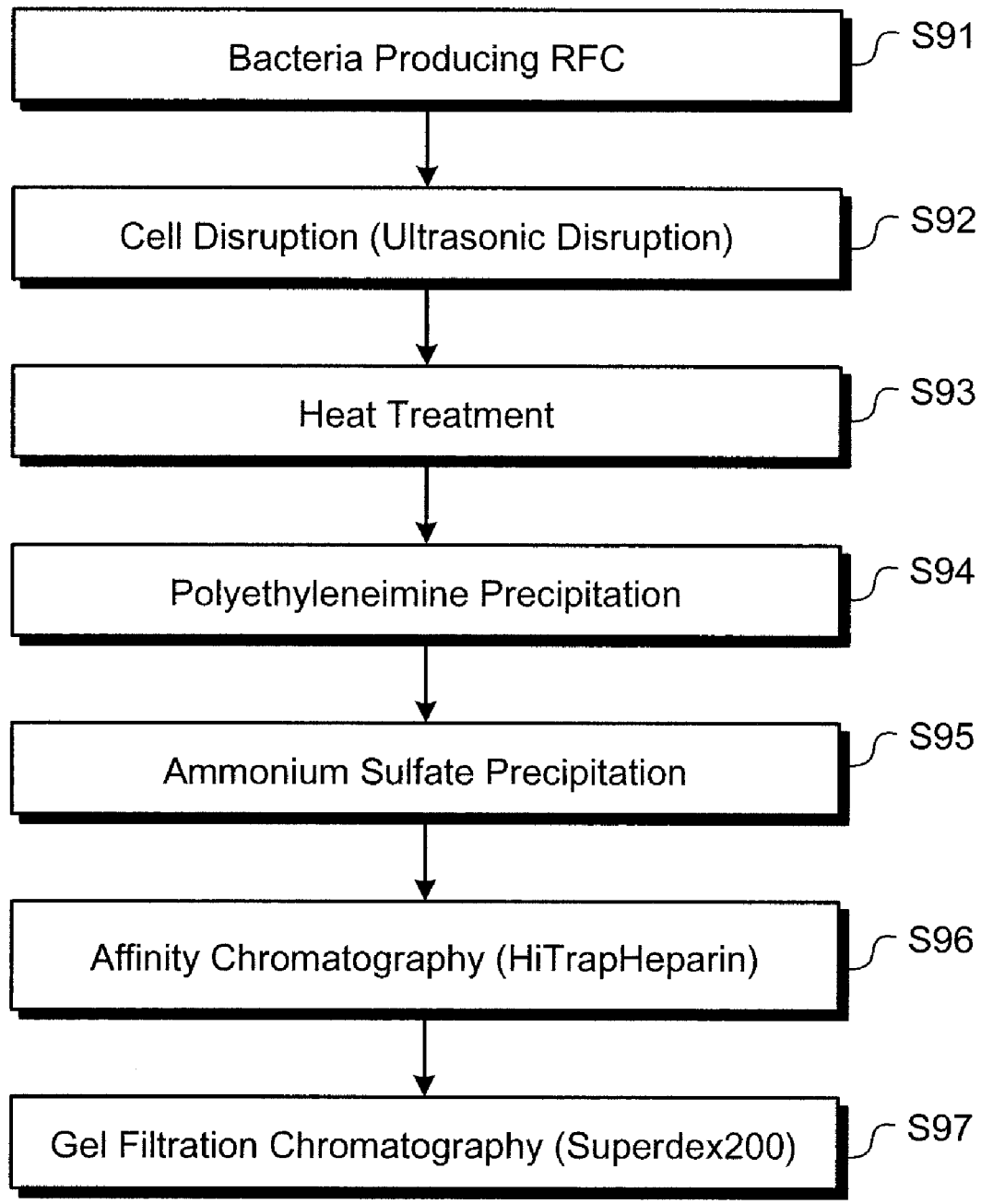
FIG. 9 is a view showing a flowchart for preparing RFC (protein).

As shown in FIG. 9, a preparation was obtained by collecting the microbial cells by centrifugation (S91), disrupting the microbial cells by ultrasonic disruption, (S92), boiling for 5 minutes (S93), performing the polyethyleneimine precipitation (S94), performing the ammonium sulfate precipitation (S95), performing the affinity chromatography (S96, using HiTrap Heparin) and performing the gel filtration chromatography (S97, using Superdex 200). It was confirmed by SDS-PAGE to assure the purity of 90% or more.

1.8.1: Disruption of Microbial Cells

The microbial cells precipitated by centrifugation were suspended in 25 mL of buffer B (aforementioned). The microbial cells were disrupted by ultrasonic treatment.

1.8.2: Treatment with Heat

A disrupted microbial cell suspension was boiled for 5 minutes and then centrifuged (18,500×g, 4° C., 25 minutes), to collect a supernatant.

1.8.3: Polyethyleneimine Precipitation

Polyethyleneimine (Sigma P-3143) was added at a final concentration of 0.18% (w/v), which was then stirred on ice for 30 minutes. This solution was centrifuged (18,500×g, 4° C., 25 minutes) to yield a supernatant.

1.8.4: Ammonium Sulfate Precipitation 5.61 g of ammonium sulfate (final concentration of 80%) was added to 10 mL of the supernatant and stirred on ice for 30 minutes to precipitate a protein. The precipitation was collected by centrifugation (18,500×g, 4° C., 25 minutes). Subsequently, this precipitation was dissolved in the buffer C (aforementioned) and the resulting solution was dialyzed against the same buffer C.

1.8.5: Affinity Chromatography

The dialyzed sample was purified using HiTrap Heparin HP column (Amersham Bioscience).

The sample was eluted with the linear gradient of 0.1 to 0.8 M of NaCl/17.5 mL, and the flow rate was 1 mL/minute.

1.8.6: Gel Filtration Chromatography

Figure 10:
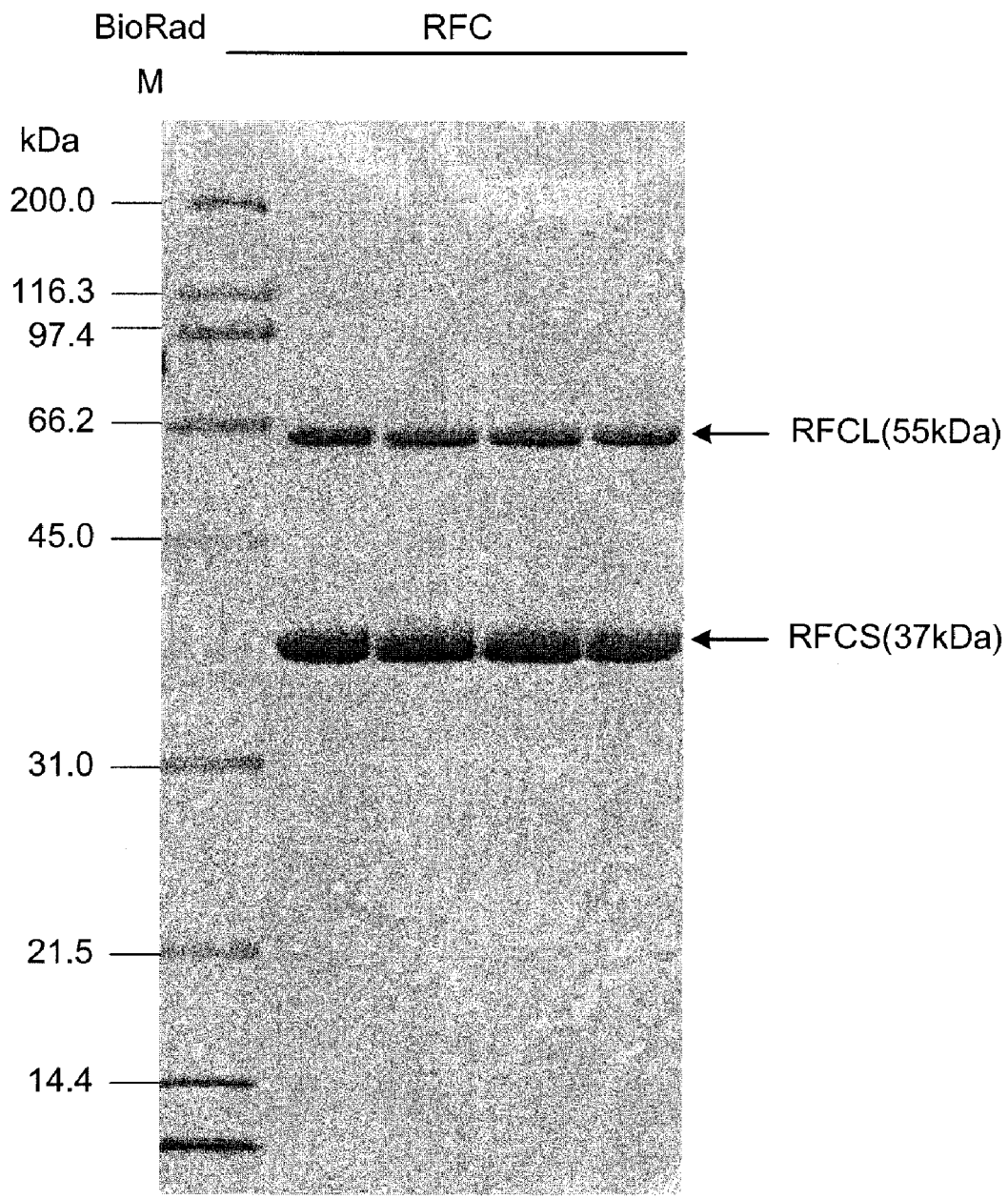
FIG. 10 is a view showing a result of polyacrylamide gel electrophoresis of a RFC protein preparation.

The peak fraction in the HiTrap Heparin affinity chromatography was further purified by gel filtration chromatography using Superdex 200 (aforementioned) to obtain a preparation for assays. The resulting preparation was applied onto the polyacrylamide gel electrophoresis to confirm the molecular size and good purification of the preparation (FIG. 10).

2. Evaluation of PCNA mutants

The effects of various PCNA mutants prepared in the aforementioned procedure on the DNA replication system, particularly on the PCR reaction system were examined. Specifically, the PCR reaction was performed with the addition of the PCNA mutant alone, RFC alone or the combination thereof, or with the addition of none of them to the PCR reaction system, and its reaction product was subjected to the electrophoresis for comparing the state of the amplified target region.

2.1: Evaluation of Various PCNA Mutants

Effect of addition of various PCNA mutants on Pyrobest DNA Polymerase (TAKAPA BIO INC.), a commercially distributed DNA synthesis enzyme derived from genus *Pyrococcus*, was examined using the PCR reaction system. Pyrobest DNA Polymerase is the heat resistant α type DNA polymerase derived from *Pyrococcus* sp. and having 3'-->5' exonuclease activity (proof reading activity). This enzyme is characterized by performing a highly correct amplification equivalent to that by Pfu DNA polymerase derived from *Pyrococcus furiosus*, and Vent DNA polymerase.

2.1.1: Composition of Reaction Solution

The reaction solution has the composition of the standard PCR reaction solution except for adding an accessory protein (sometimes abbreviated as "AP"). The attached reaction buffer (10× Pyrobest Buffer II; unpublished composition, TAKARA BIO INC.) was used as the buffer. The composition of the PCR reaction solution is shown below. As the template DNA, lambda DNA (GenBank accession 02459) was used.

TABLE 6

| Composition | Amount to be added | Final concentration |
|---|---|---|
| Lambda DNA (20 ng/μL) | 1.25 μL | 0.5 ng/μL |
| Forward Primer (20 pmol/μL) | 0.5 μL | 0.2 μM |
| Reverse Primer (20 pmol/μL) | 0.5 μL | 0.2 μM |
| 10x Pyrobest buffer II | 5 μL | 1x |
| dNTP Mix (2.5 mM each) | 4 μL | 0.2 mM |
| Pyrobest DNA Polymerase (5 U/μL) | 0.25 μL | 0.025 U/μL |
| AP solution (see Table 7) | 1.1 μL | |
| Sterile water | 37.4 μL | |
| Total | 50 μL | |

The combination of the forward primer and the reverse primer is changed depending on the length to be amplified. For the combination of the primers, see Tables 8 and 9.

TABLE 7

| AP solution (Accessory protein solution) | | | | |
|---|---|---|---|---|
| | noAP | RFC0 | RFC200 | RFC400 |
| PCNAxx | 0 μL | 0.3 μL | 0.3 μL | 0.3 μL |
| RFC | 0 μL | 0 μL | 0.4 μL | 0.8 μL |
| Buffer* | 1.1 μL | 0.8 μL | 0.4 μL | 0 μL |
| Total | 1.1 μL | 1.1 μL | 1.1 μL | 1.1 μL |

Neat concentration of PCNAxx; 100 ng/μL, neat concentration of RFC; 500 ng/μL
Buffer*: 25 mM TrisCl pH8.0, 50 mM NaCl, 50% Glycerol 2.1.2: PCR Reaction Program
In the case of 2 kb amplification
94° C. for one minute-->(98° C. for 5 seconds-->68° C. for one minute) 30 cycles-->being kept at 4° C.
In the case of 8.4 kb amplification
94° C. for one minute-->(98° C. for 5 seconds-->68° C. for 3.5 minutes) 30 cycles-->being kept at 4° C.
In the case of 15.8 kb amplification
94° C. for one minute-->(98° C. for 5 seconds-->68° C. for 7 minutes) 30 cycles-->being kept at 4° C.

Figure 11:
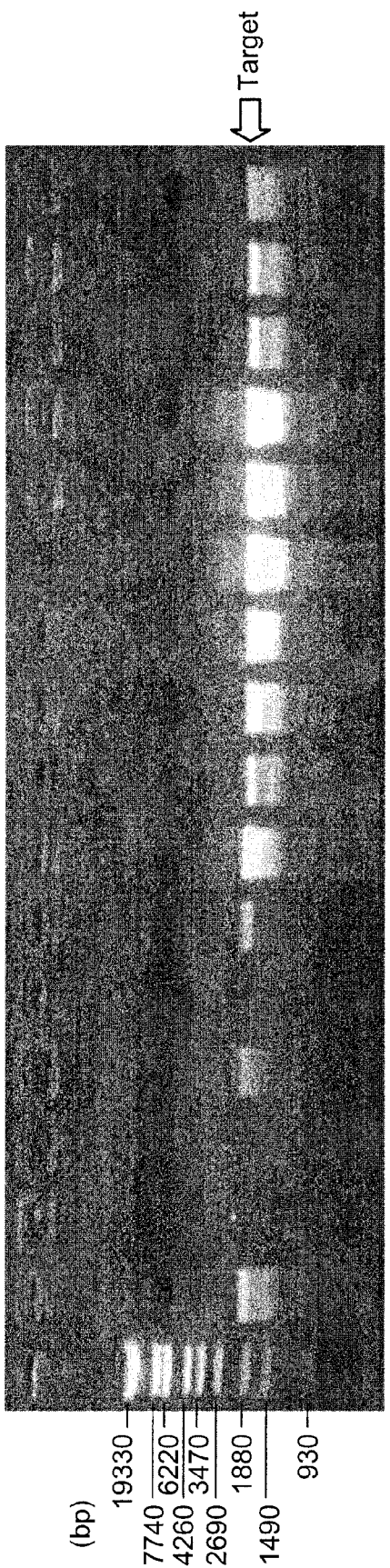
FIG. 11 is a view showing effects of adding various PCNA mutants and RFC to Pyrobest (case of 2 kb amplification).
Figure 12:
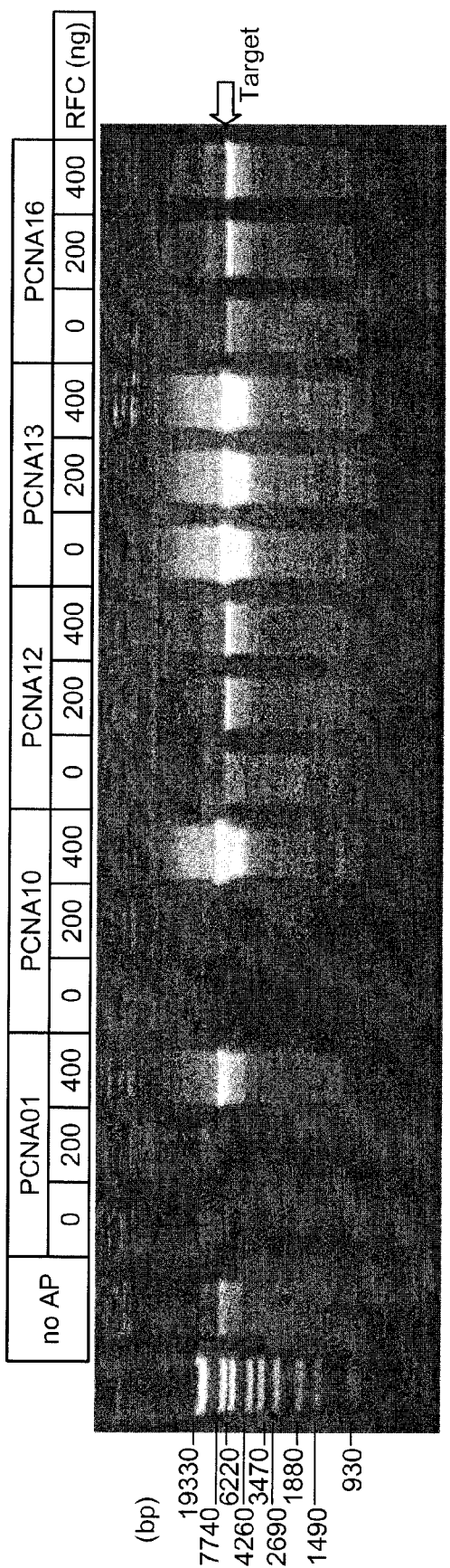
FIG. 12 is a view showing effects of adding various PCNA mutants and RFC to Pyrobest (case of 8.4 kb amplification).
Figure 13:
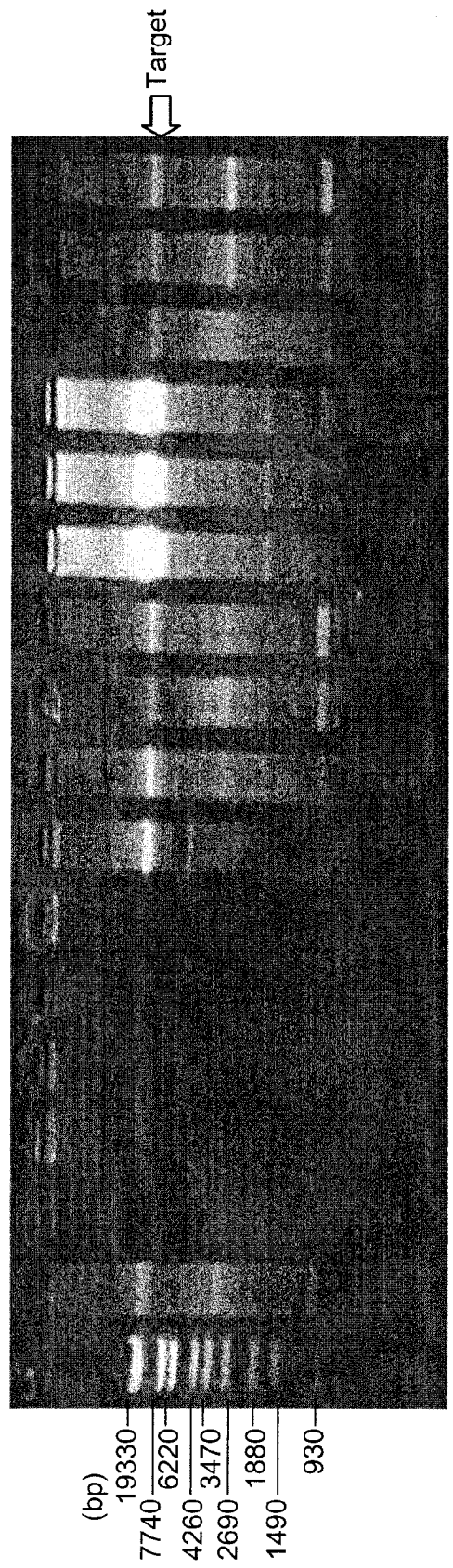
FIG. 13 is a view showing effects of adding various PCNA mutants and RFC to Pyrobest (case of 15.8 kb amplification).
Figure 41:
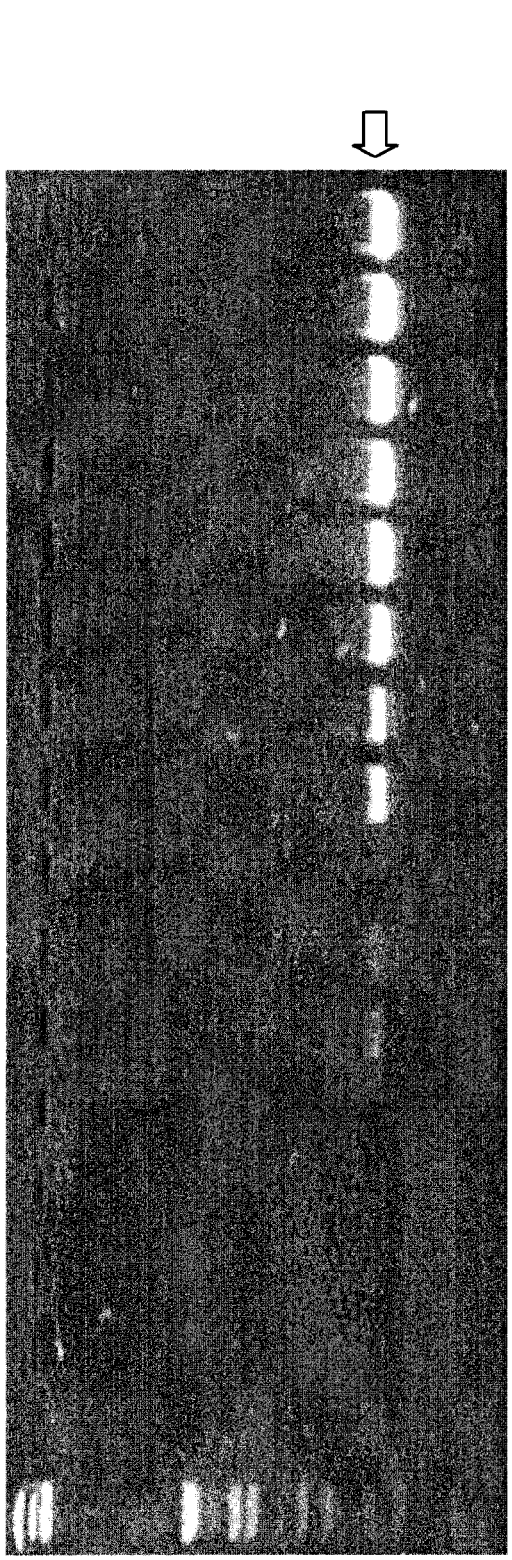
FIG. 41 is a view showing effects of adding various PCNA mutants and RFC to Pyrobest (in the case of 2 kb amplification).
Figure 42:
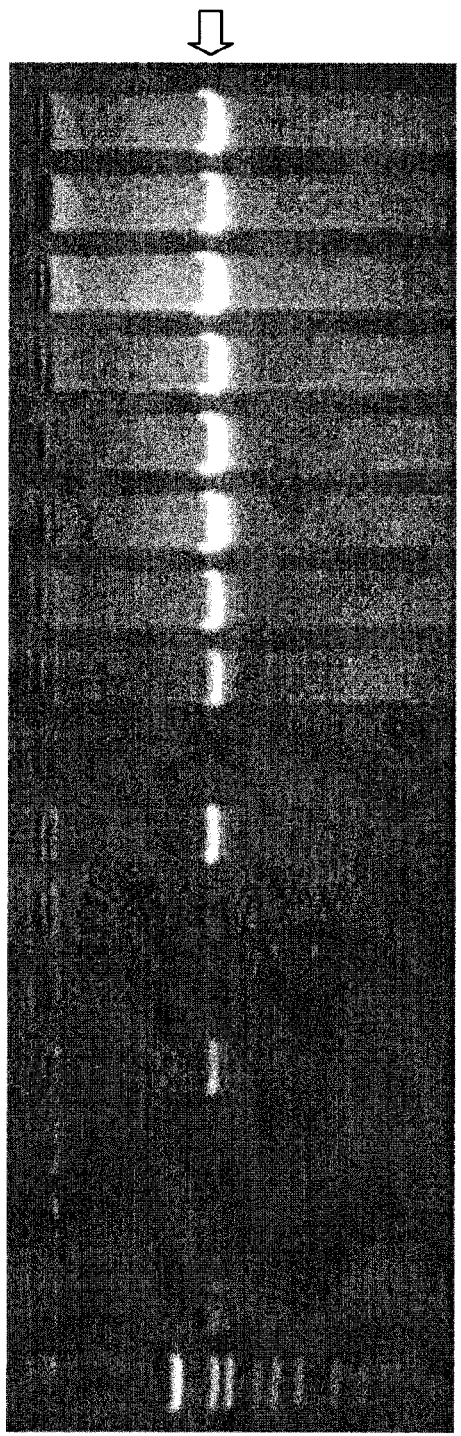
FIG. 42 is a view showing effects of adding various PCNA mutants and RFC to Pyrobest (in the case of 8.4 kb amplification).
Figure 43:
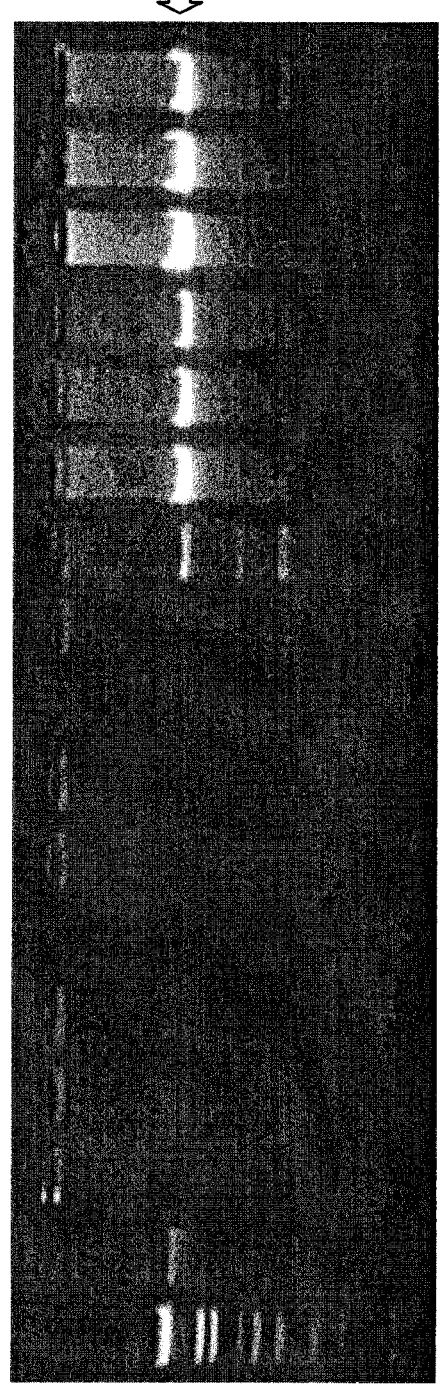
FIG. 43 is a view showing effects of adding various PCNA mutants and RFC to Pyrobest (in the case of 15.8 kb amplification).

2.1.3: Electrophoresis
After completing the PCR reaction, 5 μL of 10× loading buffer (glycerol 50%, bromophenol blue 0.4%, Xylene cyanol 0.4%) was added to and mixed with 50 μL of the PCR reaction solution, which was then subjected to 1% agarose gel electrophoresis. As an electrophoresis marker, lambda/styI marker (Toyobo Co., Ltd.) was used. The results are shown in FIGS. 11 to 13 (PCNA01, 10, 12, 13, 16), FIGS. 41 to 43 (PCNA01, 10, 13, 70, 71) and FIGS. 44 to 46 (PCNA13, 72, 77, 78, 79) which are grouped according to the size of the amplified fragments.

TABLE 8

Primer sequence for evaluating PCNA

| Primer name | Positions for primer (in lambda DNA) | Primer sequence (5' to 3') | SEQ ID NO |
|---|---|---|---|
| F02 | 23,119-23,138 | GTC GTT TCT GCA AGC TTG GC | 25 |
| F11 | 24,634-24,654 | GCT GCT GAA ACG TTG CGG TTG | 26 |
| F24 | 18,483-18,504 | CGT CCG GGA CAT TGT AAA GGC G | 27 |
| R03 | 25,142-25,122 | CCG AGA TAA AAA CAA ACC CGC | 28 |
| R14 | 26,914-26,894 | GGC ATT CCT ACG AGC AGA TGG | 29 |
| R16 | 40,479-40,460 | TCC CGT TCT TCC CTG GTA GC | 30 |

TABLE 9

Amplified region in lambda DNA

| Size | Forward Primer | Reverse Primer | lambda-DNA Position |
|---|---|---|---|
| 2 kb | F02 | R03 | 23,119-25,142 |
| 8.4 kb | F24 | R14 | 18,483-26,914 |
| 15.8 kb | F11 | R16 | 24,634-40,479 |

2.1.4: Results 1
The results in FIGS. 11 to 13 will be described.
PCNA01
When the amplified size was 2 kb or 8.4 kb, the amplification was observed only when 400 ng of RFC was added. In other cases, the addition of PCNA01 showed the inhibitory effect compared with the case of adding no accessory protein (no AP). This is the result that, when the wild type PCNA is used, the DNA can not be amplified unless the appropriate amount of RFC is used in combination. The result indicates that the addition of the wild type PCNA alone obviously inhibits the reaction in the PCR, differently from the result of the primer extension analysis (Non-patent Documents 6 and 9) in which the addition of the PCNA alone exhibits the DNA synthesis promoting activity.

PCNA10
When the amplified size was 2 kb or 8.4 kb and when 200 ng or 400 ng of RFC was added, the amplification was observed. However, when the amplified size was 15.8 kb, only the addition of 400 ng RFC resulted in the amplification. The amplified amount was larger than that in PCNA01, but the presence of RFC was required as was the case of PCNA01. It is suggested thereby that the optimal amount of RFC to be added may be different depending on the amplified size.

PCNA12
In any case of the amplified sizes 2 kb, 8.4 kb and 15.8 kb, it was observed that the addition of RFC promoted the amplified amount. Even when no RFC was added, the amplification was also observed. However, only the slight promotion of the amplification was observed compared with the case of the PCR enzyme alone.

PCNA13
In any case of the amplified sizes 2 kb, 8.4 kb and 15.8 kb, the amplification in the large amount was observed, and the amplified amount did not depend on the amount of added RFC. Addition of PCNA13 exerted effect without requiring the RFC, and it is thus conceivable that PCNA 13 remarkably promotes the amplification by PCR.

PCNA16
In any case of the amplified sizes 2 kb, 8.4 kb and 15.8 kb, the amplification was observed. The amplification was observed even when no RFC was added, although its level was equivalent to the amplification level in the case of the PCR enzyme alone. The effect of the RFC addition was scarcely observed.

For five species of PCNA, the effect of their addition to the PCR reaction system using Pyrobest DNA polymerase was examined. It was recognized that addition of PCNA13 exhibited much higher promotion effect on the amplification than in the case of no addition, and that PCNA 13 did not require the addition of RFC.

2.1.5: Results 2
The results in FIGS. 41 to 43 will be described.
PCNA01 (quasi-wild Type)
Similarly to the results in 2.1.4, in any amplified sizes other than the case of adding 400 ng of RFC, no amplification was observed, and PCNA01 worked in an inhibitory manner compared with the case of adding no PCNA (no AP).

PCNA10 (D143A)
When the amplified size was 2 kb, clear amplification was observed in the cases of adding 200 ng and 400 ng of RFC. When the amplified size was 8.4 kb, the clear amplification was observed in the cases of adding 400 ng of RFC. When the amplified size was 15.8 kb, no amplification was observed even when 400 ng of RFC was added. Similarly to the result in 2.1.4, PCNA10 was better in terms of amplified amount than PCNA01. However, the presence of RFC was indispensable for the amplification. It was suggested that the optimal amount of RFC to be added might be different depending on the amplified size.

PCNA71 (D143H)

No amplification was observed when no RFC was added, although when the amplified size was 2 kb or 8.4 kb, the amplification was observed when 200 ng or 400 ng of RFC was added, and when the amplified size was 15.4 kb, the amplification was observed when 400 ng of RFC was added. The amplified amount was larger than in the case of PCNA10, but the addition of RFC was required for the amplification.

PCNA70 (D143K)

Not depending on the presence or absence of RFC and the amount of added RFC, the amplification in the large amount was observed in any sizes examined.

PCNA13 (D143R)

Similarly to the result in 2.1.4, the amplification in the large amount was observed in any sizes examined not depending on the addition of RFC, and the amplification level was better than in the case of PCNA70.

For four species of mutants (PCNA10, 13, 70 and 71) obtained by introducing the mutation into the position 143 in the PCNA, the effect of their addition to the PCR reaction system was examined. Only PCNA70 (D143K) and PCNA13 (D143R) exhibited the promotion effect not depending on the addition of RFC. PCNA13 obtained by substitution with the arginine residue having higher basicity exhibited the strongest promotion effect. Therefore, it is conceivable that, for leading to the PCR promotion effect of PCNA alone by introducing the mutation into the D143 residue, it is necessary to substitute with the basic amino acid residue, and that it is important that the positive charge which the substituted residue has under the PCR reaction conditions (pH 8.0 or higher) causes the charge repulsion against the ion pair network in the interface between the monomers.

2.1.6: Results 3

Figure 44:
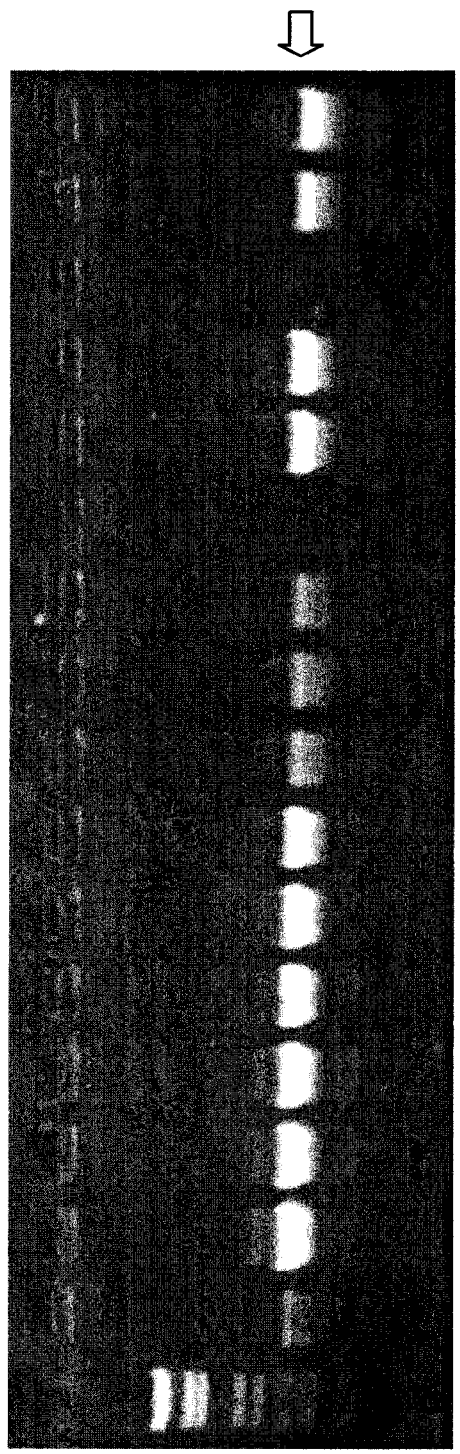
FIG. 44 is a view showing effects of adding various PCNA mutants and RFC to Pyrobest (in the case of 2 kb amplification).
Figure 45:
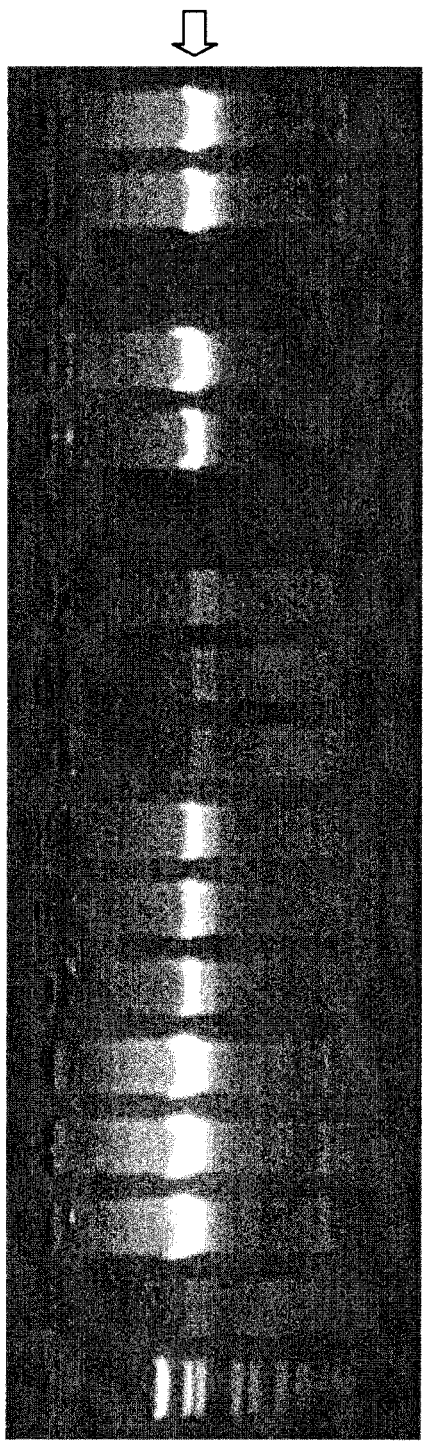
FIG. 45 is a view showing effects of adding various PCNA mutants and RFC to Pyrobest (in the case of 8.4 kb amplification).
Figure 46:
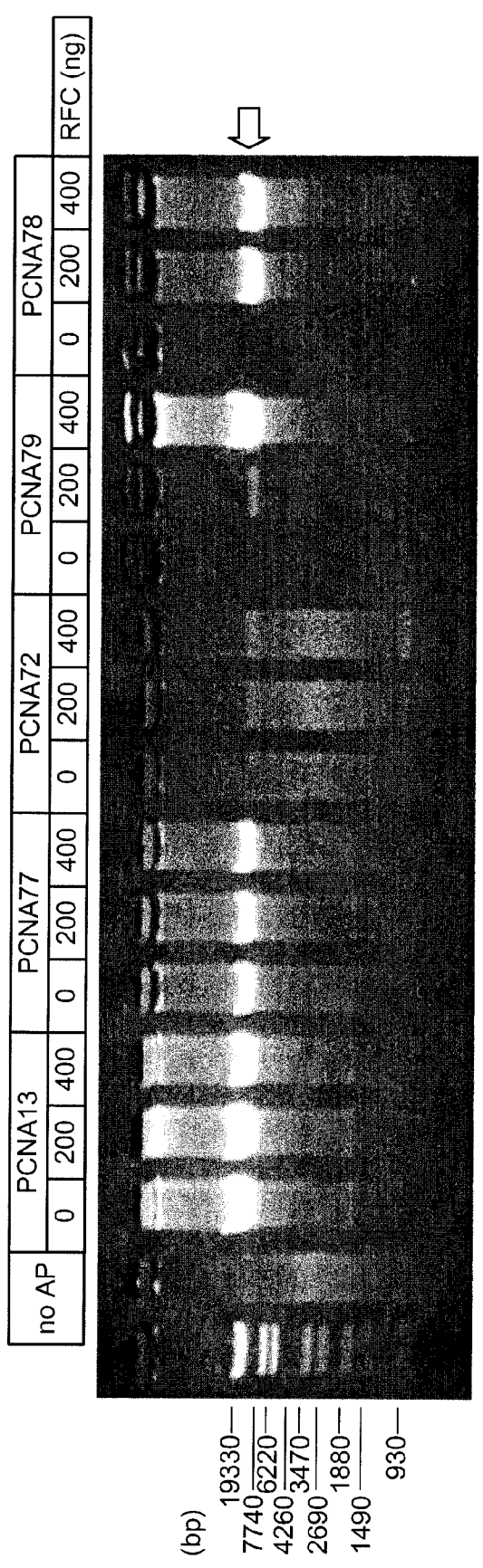
FIG. 46 is a view showing effects of adding various PCNA mutants and RFC to Pyrobest (in the case of 15.8 kb amplification).

The results in FIGS. 44 to 46 will be described.

PCNA13 (D143R)

Similarly to the results in 2.1.4 and 2.1.5, the amplification in the large amount was observed in any sizes examined not depending on the RFC.

PCNA77 (D147R)

Not depending on the presence or absence of RFC and the amount of added RFC, the amplification in the large amount was observed in any sizes examined. PCNA77 was inferior in terms of amplified amount to PCNA13.

PCNA72 (R109E)

The difference in comparison with the case of adding no PCNA (no AP) was scarcely observed in any cases regardless of amplified sizes, the presence or absence of RFC and the amount of added RFC.

PCNA79 (E139R)

In all cases with various amplified sizes, the promotion effect was observed when 200 ng to 400 ng of RFC was simultaneously added. However, the presence of RFC was essential for the amplification, as the addition of PCNA79 alone inhibited the reaction.

PCNA78 (E139A)

In all cases with various amplified sizes, the promotion effect was observed when 200 ng to 400 ng of RFC was simultaneously added. However, the presence of RFC was essential for the amplification, as the addition of PCNA78 alone inhibited the reaction. Comparing with PCNA79, PCNA78 was superior or inferior thereto depending on the amplified size when 200 ng of RFC was simultaneously added. However, when 400 ng of RFC was simultaneously added, PCNA78 was inferior to PCNA79 in terms of amplified amount. It is conceivable that the substitution with the basic amino acid residue (arginine) exerts a higher effect than the substitution with the neutral amino acid residue (alanine) when the substitution is introduced into the E139 residue as well.

The effect on the PCR reaction system of addition thereto the mutants of Pfu-PCNA obtained as a result of introduction of the mutation by substituting any of four amino acid residues among amino acid residues located on the interface when the Pfu-PCNA forms the homotrimer and involved in the formation of the trimer. The results were classified into three types. The first group inhibits reaction when added alone whereas, when added simultaneously with RFC, the reaction is offset depending on the amount of added RFC; depending on the added amount, the amplification may become larger than in the case of adding no PCNA (no AP). The second group brings about almost no difference from the no addition (no AP) group, either when added alone or when added simultaneously with RFC; this group is thus considered as not being involved in the reaction. The third group promotes the reaction regardless the presence or absence of RFC. It is conceivable that the point would be an ability to form the trimer, and that these phenomena are due to an extent to weaken the ion pair network. That is, if the trimer structure is too firm, the reaction would not progress without aid of RFC. If the ability to form the trimer is lost, PCNA would lose ability to work as the clump. It is thus speculated that the state where the trimer structure is appropriately loosened to an intermediate level would be important for promoting the enzyme activity in the PCR reaction.

It is conceivable that the ability to form the trimer in an effective manner for promoting the enzyme activity in the PCR reaction is realized by causing the charge repulsion to the ion pair network in the interface between the monomers. It is also conceivable that the trimer is easily dissociated under the high temperature by loosening the ion pair network which is supposed to contribute to the thermal stability. A reaction mechanism is speculated that the replication reaction is repeated by dissociating the trimer upon temperature elevation for the subsequent cycle in PCR or at high temperature in the initial denaturation step of the cycle.

The effect of adding them to the PCR reaction system was examined as to the eleven mutants. Those which exhibited the promotion effect not depending on the addition of RFC were three mutants, PCNA13 (D143R), PCNA70 (D143K) and PCNA77 (D147R), and among them, PCNA13 exhibited the strongest overwhelming amplification effect. It was also observed that simultaneous addition of RFC appears to have tendency to rather reduce the amplified amount.

2.2: Effect of PCNA13 on Various DNA Polymerase for PCR

Based on the aforementioned results, PCNA13 having the particularly excellent nature among various PCNA mutants were further examined as to the effect of adding the same to the PCR reaction system using commercially available seven DNA polymerases for PCR. Specifically, the PCR reactions with a variety of extension time periods were performed for two or three target sequences having the different amplified length, and the effect of adding PCNA 13 thereto was examined.

2.2.1: Effect of Adding PCNA13 to Pyrobest DNA Polymerase

Pyrobest DNA polymerase is a heat resistant α type DNA polymerase derived from *Pyrococcus* sp. and having the 3'-->5' exonuclease activity.

The PCR reaction solution having the composition recommended in the instructions by the manufacturer was used except that PCNA13 was added to the solution. The reaction buffer (10× Pyrobest Buffer II; unpublished composition, TAKARA BIO INC.) attached to the product was used as the buffer. The composition of the PCR reaction solution is shown below.

TABLE 10

| Composition | Amount to be added | Final concentration |
|---|---|---|
| Lambda DNA (20 ng/μL) | 1.25 μL | 0.5 ng/μL |
| Forward Primer (20 pmol/μL)[1] | 0.5 μL | 0.2 μM |
| Reverse Primer (20 pmol/μL)[1] | 0.5 μL | 0.2 μM |
| 10x Pyrobest buffer II | 5 μL | 1x |
| dNTP Mix (2.5 mM each) | 4 μL | 0.2 mM |
| Pyrobest DNA Polymerase (5 U/μL) | 0.25 μL | 0.025 U/μL |
| PCNA13 solution or buffer[2] | 0.3 μL | 0 or 0.6 ng/μL |
| Sterile water | 38.2 μL | |
| Total | 50 μL | |

[1] The combination of the forward primer and the reverse primer is changed depending on the length to be amplified. For the combination of the primers, see Tables 8 and 9.
[2] Neat concentration of PCNA 13; 100 ng/μL, Buffer; 25 mM TrisCl pH8.0, 50 mM NaCl, 50% Glycerol PCR reaction program
In the case of 2 kb amplification
94° C. for one minute-->(98° C. for 5 seconds-->68° C. for 0.5, 1, 2 minute) 30 cycles-->being kept at 4° C.
In the case of 8.4 kb amplification
94° C. for one minute-->(98° C. for 5 seconds-->68° C. for 2, 3.5, 5 minutes) 30 cycles-->being kept at 4° C.
In the case of 15.8 kb amplification
94° C. for one minute-->(98° C. for 5 seconds-->68° C. for 2, 5, 6, 7 minutes) 30 cycles-->being kept at 4° C.

Electrophoresis

Figure 15:
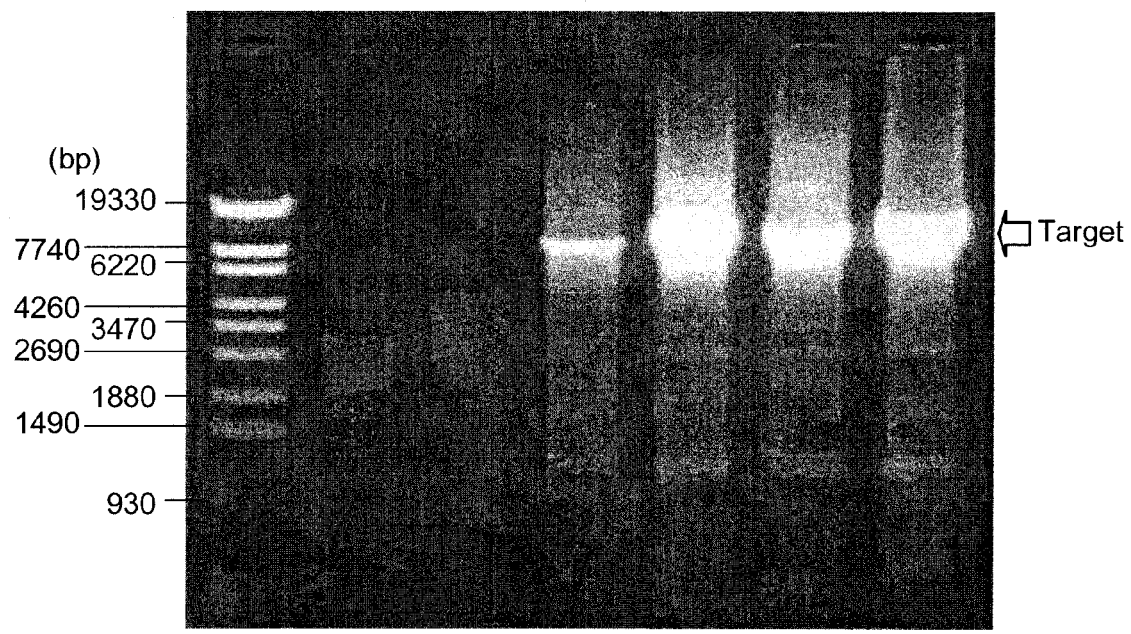
FIG. 15 is a view showing effects of adding PCNA13 to Pyrobest for each extension time when the amplified length was 8.4.
Figure 16:
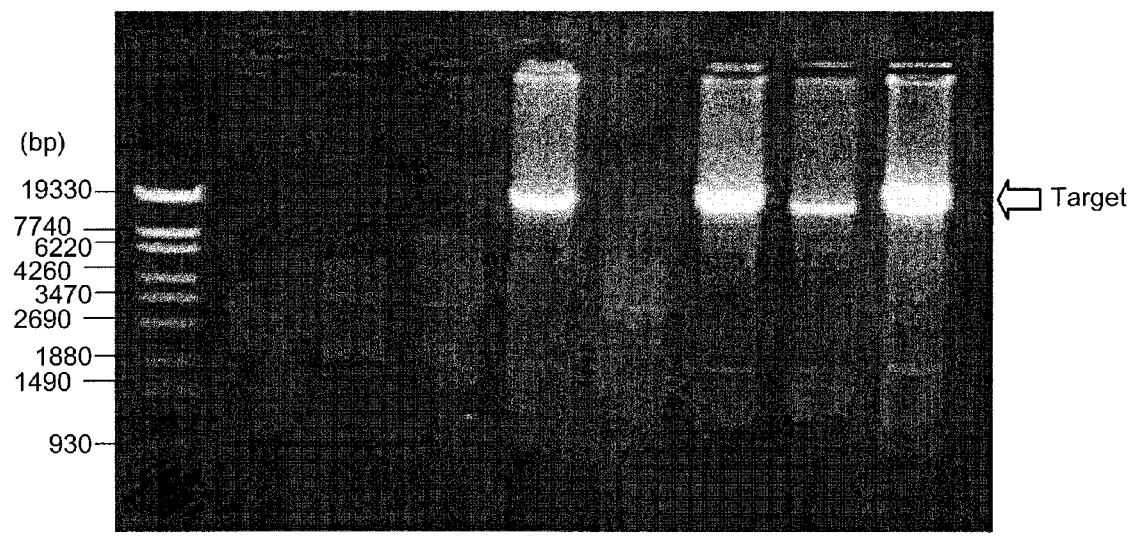
FIG. 16 is a view showing effects of adding PCNA13 to Pyrobest for each extension time when the amplified length was 15.8.

After completing the PCR, 5 μL of 10x loading buffer (glycerol 50%, bromophenol blue 0.4%, Xylene cyanol 0.4%) was added to and mixed with 50 μL of the PCR reaction solution, and a specific amount of the mixture corresponding to 10 μL of the PCR reaction solution was then subjected to 1% agarose gel electrophoresis. As the electrophoresis marker, lambda/styI marker (Toyobo Co., Ltd.) was used. The results are shown in FIGS. 14 to 16 which are grouped according to the size of the amplified fragment.

SUMMARY

Figure 14:
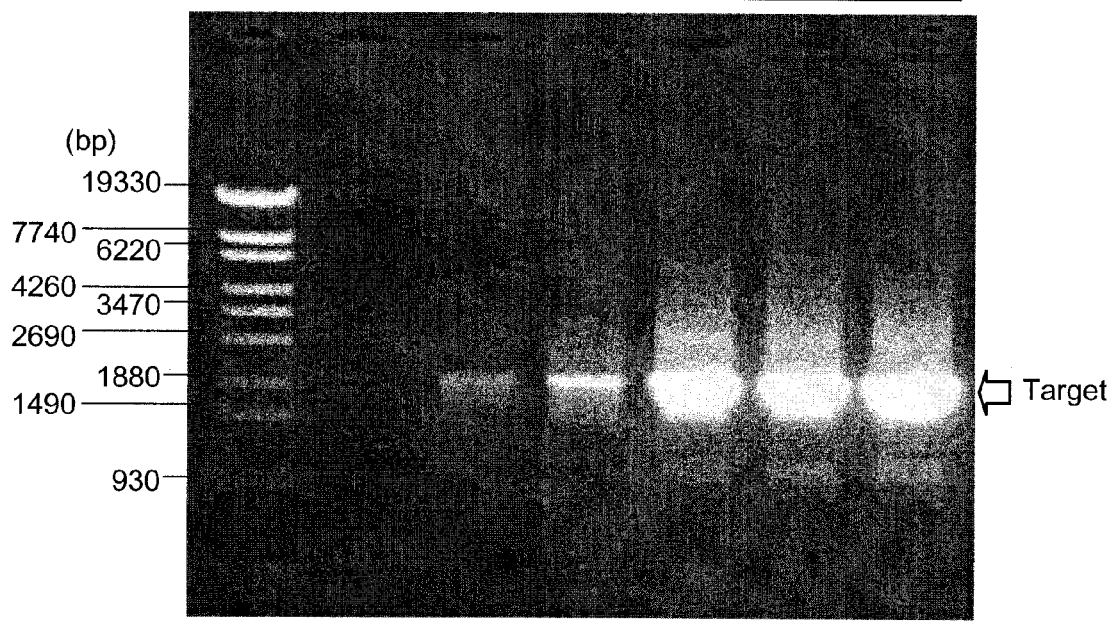
FIG. 14 is a view showing effects of adding PCNA13 to Pyrobest for each extension time when an amplified length was 2 kb.

In the case of 2 kb amplification
As shown in FIG. 14, the promotion of the reaction by the addition of PCNA13 was obviously recognized when the extension time is 0.5 or one minute. With the extension time of 2 minutes, the reaction was almost saturated, but it was observed that the amplified amount was slightly larger when PCNA13 is added.
In the case of 8.4 kb amplification
As shown in FIG. 15, no effect of adding PCNA13 was observed with the extension time of 2 minutes, but the promotion effect by the addition was observed with the extension time of 3.5 or 5 minutes.
In the case of 15.8 amplification
As shown in FIG. 16, no effect of adding PCNA13 was observed with the extension time of 2 minutes, but the promotion effect by the addition was observed with the extension time of 5, 6 or 7 minutes.

2.2.2: Effect of Adding PCNA13 to TaKaRa Ex Taq

TaKaRa Ex Taq (TAKARA BIO INC.) is a heat resistant DNA polymerase having the 3'-->5' exonuclease activity (proof reading activity). Under the ordinary PCR conditions, TaKaRa Ex Taq can realize the more highly sensitive PCR with higher amplification efficiency and lower error rate than conventional Taq DNA polymerase.

The PCR reaction solution having the composition recommended in the instructions by the manufacturer was used except that PCNA 13 was added to the solution. The reaction buffer 10x Ex Taq buffer (20 mM $Mg^{2+}$ plus, unpublished composition, TAKARA BIO INC.) attached to the product was used as the buffer. The composition of the PCR reaction solution is shown below.

TABLE 11

| Composition | Amount to be added | Final concentration |
|---|---|---|
| Lambda DNA (20 ng/μL) | 1.25 μL | 0.5 ng/μL |
| Forward Primer (20 pmol/μL)[1] | 0.5 μL | 0.2 μM |
| Reverse Primer (20 pmol/μL)[1] | 0.5 μL | 0.2 μM |
| 10x Ex Taq buffer (20 mM $Mg^{2+}$) | 5 μL | 1x |
| dNTP Mix (2.5 mM each) | 4 μL | 0.2 mM |
| TaKaRa EX Taq (5 U/μL) | 0.25 μL | 0.025 U/μL |
| PCNA13 solution or buffer[2] | 0.5 μL | 0 or 1 ng/μL |
| Sterile water | 38 μL | |
| Total | 50 μL | |

[1] The combination of the forward primer and the reverse primer is changed depending on the length to be amplified. For the combination of the primers, see Tables 8 and 9.
[2] Neat concentration of PCNA 13; 100 ng/μL, Buffer; 25 mM TrisCl pH8.0, 50 mM NaCl, 50% Glycerol PCR Reaction Program
In the case of 2 kb amplification
94° C. for one minute-->(98° C. for 5 seconds-->68° C. for 30 seconds, 40 seconds, one minute) 30 cycles-->72° C. for 10 minutes-->being kept at 4° C.
In the case of 8.4 kb amplification
94° C. for one minute-->(98° C. for 5 seconds-->68° C. for 1.5, 2, 3 minutes) 30 cycles-->72° C. for 10 minutes-->being kept at 4° C.
In the case of 15.8 kb amplification
94° C. for one minute-->(98° C. for 5 seconds-->68° C. for 3.5, 4, 5 minutes) 30 cycles-->72° C. for 10 minutes-->being kept at 4° C.

Electrophoresis

Figure 18:
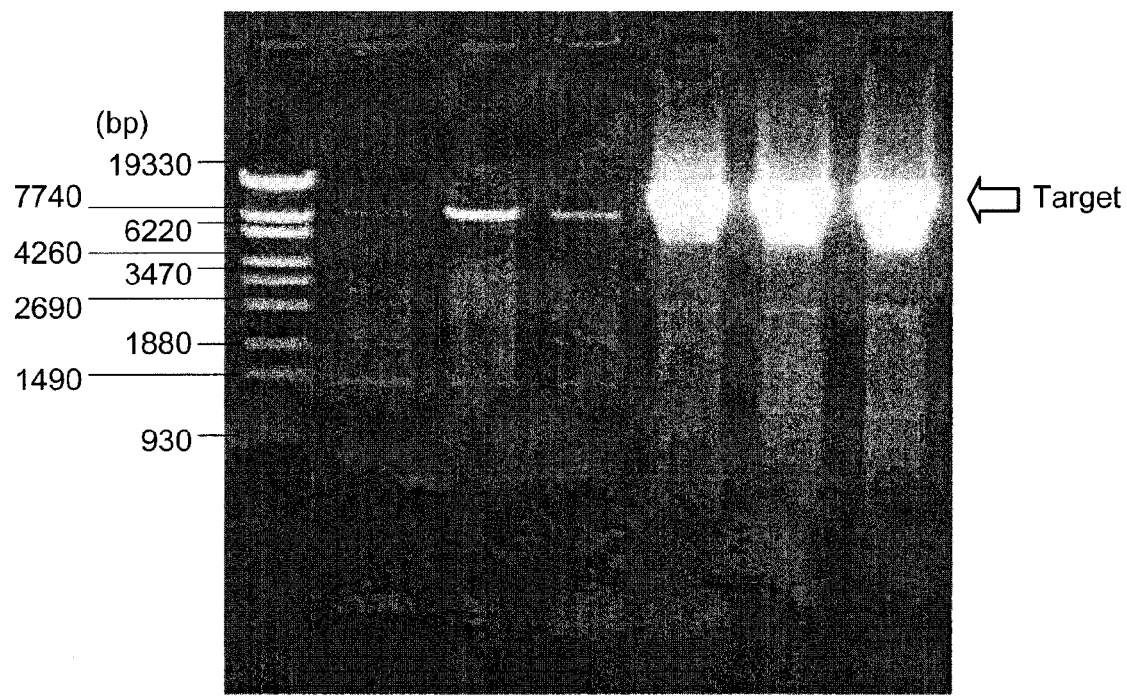
FIG. 18 is a view showing effects of adding PCNA13 to ExTaq for each extension time when the amplified length was 8.4 kb.
Figure 19:
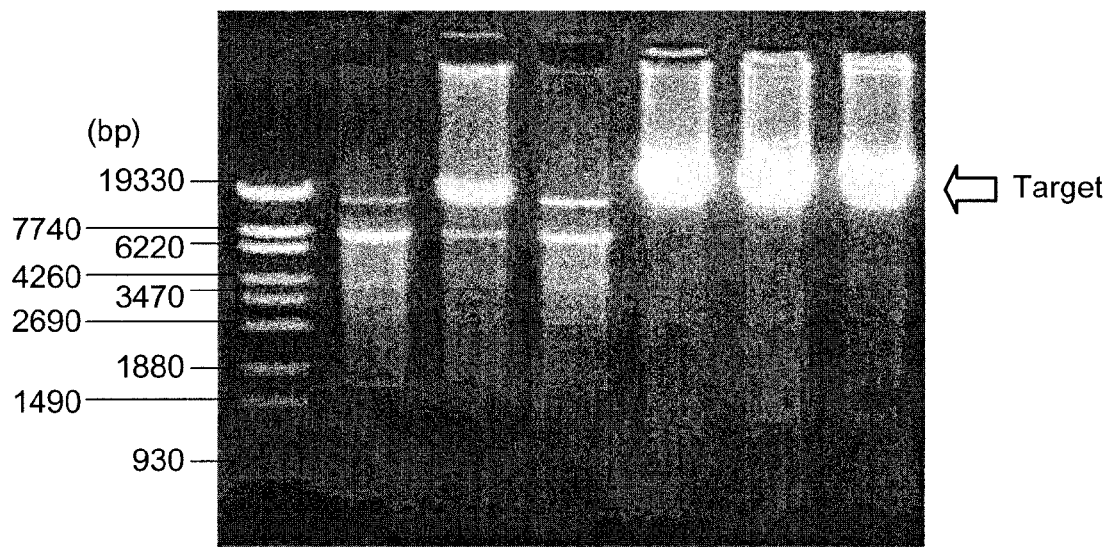
FIG. 19 is a view showing effects of adding PCNA13 to ExTaq for each extension time when the amplified length was 15.8 kb.

After completing the PCR reaction, 5 μL of 10x loading buffer (glycerol 50%, bromophenol blue 0.4%, Xylene cyanol 0.4%) was added to and mixed with 50 μL of the PCR reaction solution, and a specific amount of the mixture corresponding to 10 μL of the PCR reaction solution was then subjected to 1% agarose gel electrophoresis. As the electrophoresis marker, lambda/styI marker (Toyobo Co., Ltd.) was used. The results are shown in FIGS. 17 to 19 which are grouped according to the size of the amplified fragment.

SUMMARY

Figure 17:
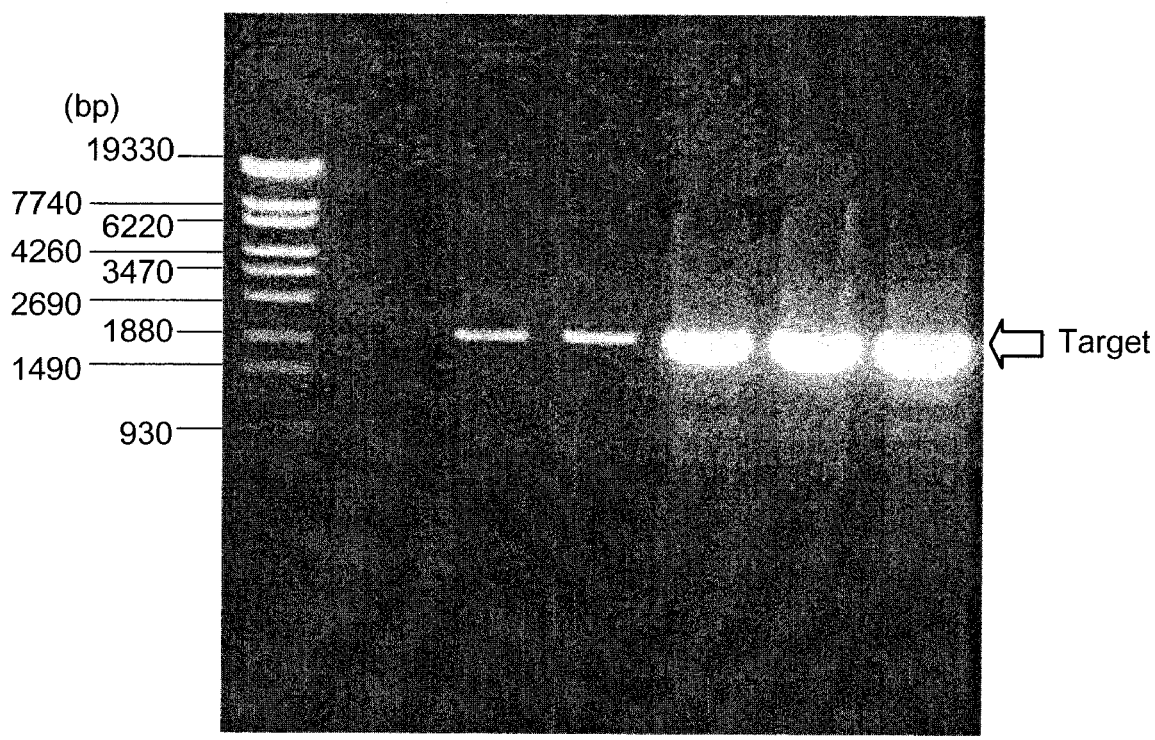
FIG. 17 is a view showing effects of adding PCNA13 to ExTaq for each extension time when the amplified length was 2 kb.

In the case of 2 kb amplification
As shown in FIG. 17, the increase in amplified amount and reaction rate by the addition of PCNA13 was obviously recognized with the extension time of 30 seconds and 40 seconds. With the extension time of one minute, the reaction attained to saturation regardless of the addition or no addition, and it is found that the amplified amount when PCNA13 was added with the extension time of 40 seconds is close to the saturation of the reaction.

In the case of 8.4 kb amplification

As shown in FIG. 18, with extension time of 1.5 and 2 minutes, the increase in amplified amount and reaction rate by the addition of PCNA13 was obviously recognized. With the extension time of 3 minutes, the reaction attained to saturation regardless of the addition or no addition, and it is found that the amplified amount when PCNA13 was added with the extension time of 2 minutes is close to the saturation of the reaction.

In the case of 15.8 kb amplification

As shown in FIG. 19, with extension time of 3.5 and 4 minutes, the increase in amplified amount and reaction rate by the addition of PCNA13 was obviously recognized. With the extension time of 5 minutes, the reaction attained to saturation regardless of the addition or no addition, and it is found that the amplified amount when PCNA13 was added with the extension time of 4 minutes is close to the saturation of the reaction.

2.2.3: Effect of Adding PCNA13 to Vent DNA Polymerase

Vent DNA polymerase is an enzyme for PCR derived from thermophile, *Thermococcus litoralis* and distributed by NEW ENGLAND Bio Labs.

Upon evaluation, the PCR reaction solution having the standard composition was used except that PCNA13 was added to the solution. The reaction buffer (10× ThermoPol Reaction Buffer; 200 mM Tris-HCl, 100 mM $(NH_4)_2SO_4$, 100 mM KCl, 20 mM $MgSO_4$, 1% Triton X-100, pH 8.8, at 25° C.) attached to the product was used as the buffer. The composition of the PCR reaction solution is shown below.

TABLE 12

| Composition | Amount to be added | Final concentration |
|---|---|---|
| Lambda DNA (20 ng/μL) | 1.25 μL | 0.5 ng/μL |
| Forward Primer (20 pmol/μL)[1] | 0.5 μL | 0.2 μM |
| Reverse Primer (20 pmol/μL)[1] | 0.5 μL | 0.2 μM |
| 10× ThermoPol Reaction Buffer | 5 μL | 1× |
| dNTP Mix (2.5 mM each) | 4 μL | 0.2 mM |
| Vent DNA Polymerase (2 U/μL) | 0.25 μL | 0.01 U/μL |
| PCNA13 solution or buffer[2] | 0.3 μL | 0 or 0.6 ng/μL |
| Sterile water | 38.2 μL | |
| Total | 50 μL | |

[1]The combination of the forward primer and the reverse primer is changed depending on the length to be amplified. For the combination of the primers, see Tables 8 and 9.
[2]Neat concentration of PCNA 13; 100 ng/μL, Buffer; 25 mM TrisCl pH8.0, 50 mM NaCl, 50% Glycerol PCR Reaction Program In the case of 2 kb amplification 95° C. for 2 minutes-->(95° C. for 30 seconds-->55° C. for 30 seconds-->72° C. for 5, 15, 30 seconds) 30 cycles-->72° C. for 10 minutes-->being kept at 4° C.

In the case of 8.4 kb amplification

95° C. for 2 minutes-->(95° C. for 30 seconds-->55° C. for 30 seconds-->72° C. for 1, 3, 5 minutes) 30 cycles-->72° C. for 10 minutes-->being kept at 4° C.

Electrophoresis

After completing the PCR reaction, 5 μL of 10× loading buffer (glycerol 50%, bromophenol blue 0.4%, Xylene cyanol 0.4%) was added to and mixed with 50 μL of the PCR reaction solution, and a specific amount of the mixture corresponding to 10 μL of the PCR reaction solution was then subjected to 1% agarose gel electrophoresis. As the electrophoresis marker, lambda/styI marker (Toyobo Co., Ltd.) was used. The results are shown in FIGS. 20 and 21 which are grouped according to the size of the amplified fragment.

SUMMARY

In the case of 2 kb amplification

Figure 20:
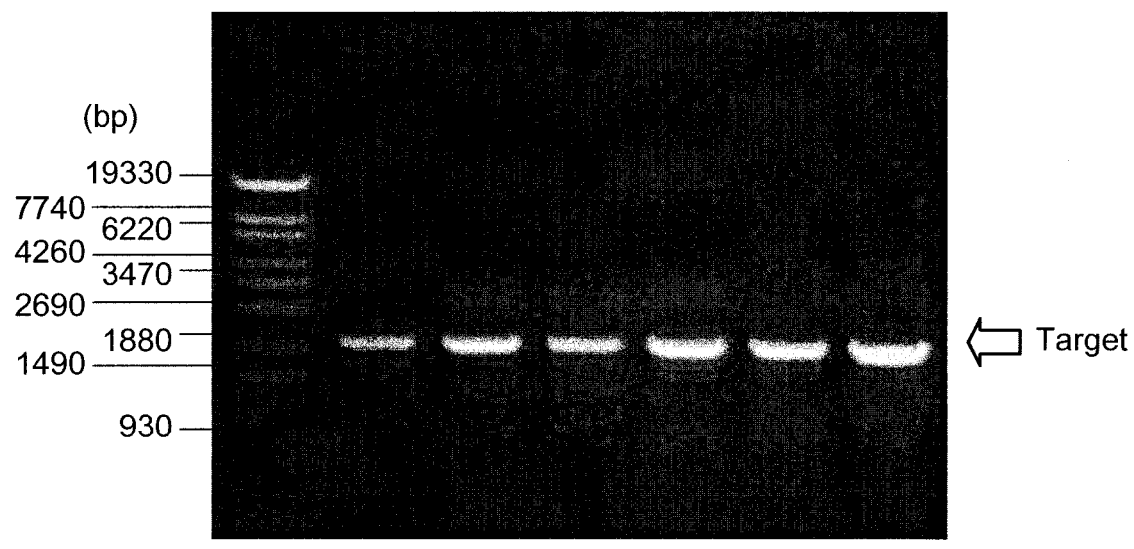
FIG. 20 is a view showing effects of adding PCNA13 to Vent DNA polymerase for each extension time when the amplified length was 2 kb.
Figure 21:
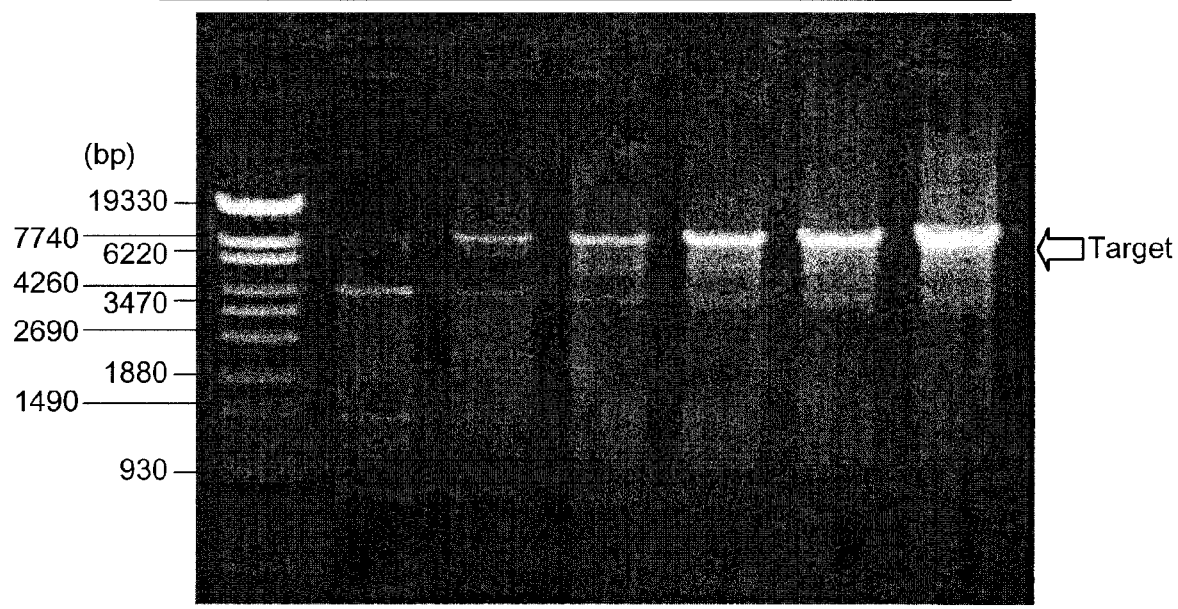
FIG. 21 is a view showing effects of adding PCNA13 to Vent DNA polymerase for each extension time when the amplified length was 8.4 kb.

As shown in FIG. 20, the promotion of the reaction by the addition of PCNA13 was obviously recognized with the extension time of 5 seconds and 15 seconds. With the extension time of 30 seconds, the reaction was almost saturated, but it was observed that the amplified amount was nevertheless slightly larger in the case of adding PCNA13.

In the case of 8.4 kb amplification

As shown in FIG. 21, the promotion effect (amplified amount, reaction rate) by the addition was observed the extension time was 1, 3 or 5 minutes.

2.2.4: Effect of Adding PCNA13 to Deep Vent DNA Polymerase

Deep vent DNA polymerase (New England Biolabs) is a heat resistant DNA polymerase derived from *Pyrococcus* species GB-D1 and has the 3'-->5' exonuclease activity.

Upon evaluation, the PCR reaction solution having the standard composition was used except that PCNA13 was added to the solution. The reaction buffer (10× ThermoPol Reaction Buffer; 200 mM Tris-HCl, 100 mM $(NH_4)_2SO_4$, 100 mM KCl, 20 mM $MgSO_4$, 1% Triton X-100, pH 8.8, at 25° C.) attached to the product was used as the buffer. The composition of the PCR reaction solution is shown below.

TABLE 13

| Composition | Amount to be added | Final concentration |
|---|---|---|
| Lambda DNA (20 ng/μL) | 1.25 μL | 0.5 ng/μL |
| Forward Primer (20 pmol/μL)[1] | 1 μL | 0.4 μM |
| Reverse Primer (20 pmol/μL)[1] | 1 μL | 0.4 μM |
| 10× ThermoPol Reaction Buffer | 5 μL | 1× |
| dNTP Mix (2.5 mM each) | 4 μL | 0.2 mM |
| Deep Vent DNA Polymerase (2 U/μL) | 0.5 μL | 0.02 U/μL |
| PCNA13 solution or buffer[2] | 0.3 μL | 0 or 0.6 ng/μL |
| Sterile water | 36.95 μL | |
| Total | 50 μL | |

[1]The combination of the forward primer and the reverse primer is changed depending on the length to be amplified. For the combination of the primers, see Tables 8 and 9.
[2]Neat concentration of PCNA 13; 100 ng/μL, Buffer; 25 mM TrisCl pH8.0, 50 mM NaCl, 50% Glycerol PCR reaction program In the case of 2 kb amplification 95° C. for 2 minutes-->(95° C. for 30 seconds-->55° C. for 30 seconds-->72° C. for 0.5, 1, 2, 3 minutes) 30 cycles-->72° C. for 10 minutes-->being kept at 4° C.

In the case of 8.4 kb amplification 95° C. for 2 minutes-->(95° C. for 30 seconds-->55° C. for 30 seconds-->72° C. for 5, 7, 9 minutes) 30 cycles-->72° C. for 10 minutes-->being kept at 4° C.

Electrophoresis

After completing the PCR reaction, 5 µL of 10× loading buffer (glycerol 50%, bromophenol blue 0.4%, Xylene cyanol 0.4%) was added to and mixed with 50 µL of the PCR reaction solution, and a specific amount of the mixture corresponding to 10 µL of the PCR reaction solution was then subjected to 1% agarose gel electrophoresis. As the electrophoresis marker, lambda/styI marker (Toyobo Co., Ltd.) was used. The results are shown in FIGS. 22 and 23 which are grouped according to the size of the amplified fragment.

SUMMARY

Figure 22:
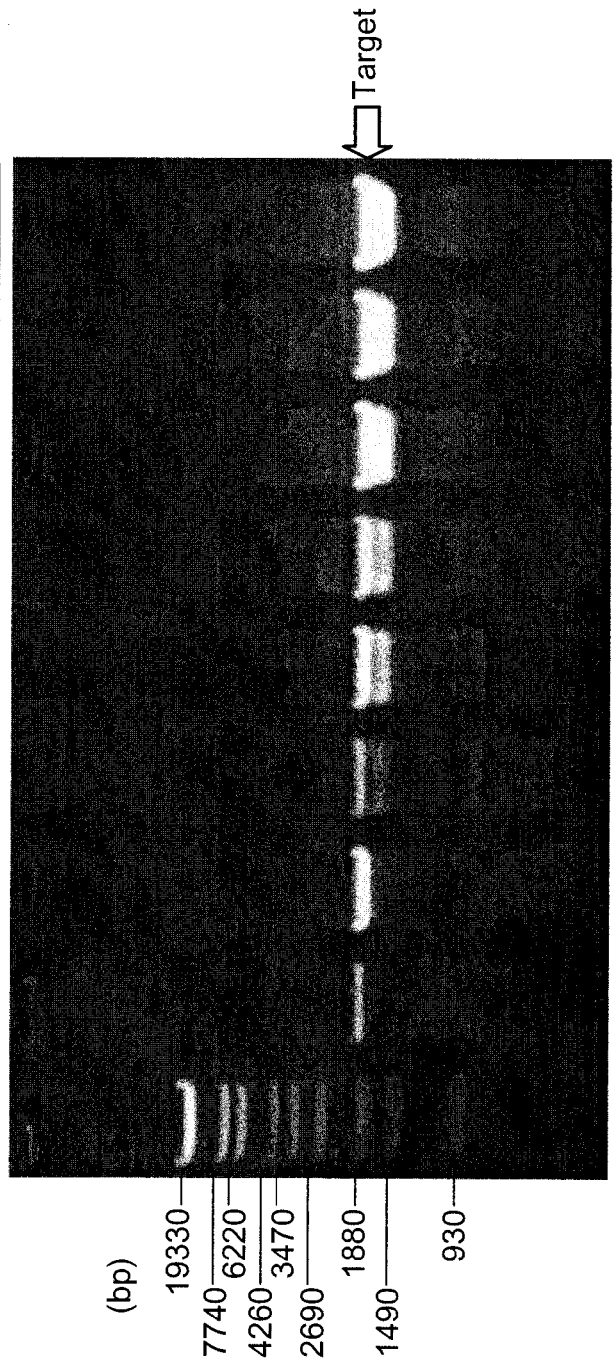
FIG. 22 is a view showing effects of adding PCNA13 to Deep Vent DNA polymerase for each extension time when the amplified length was 2 kb.
Figure 23:
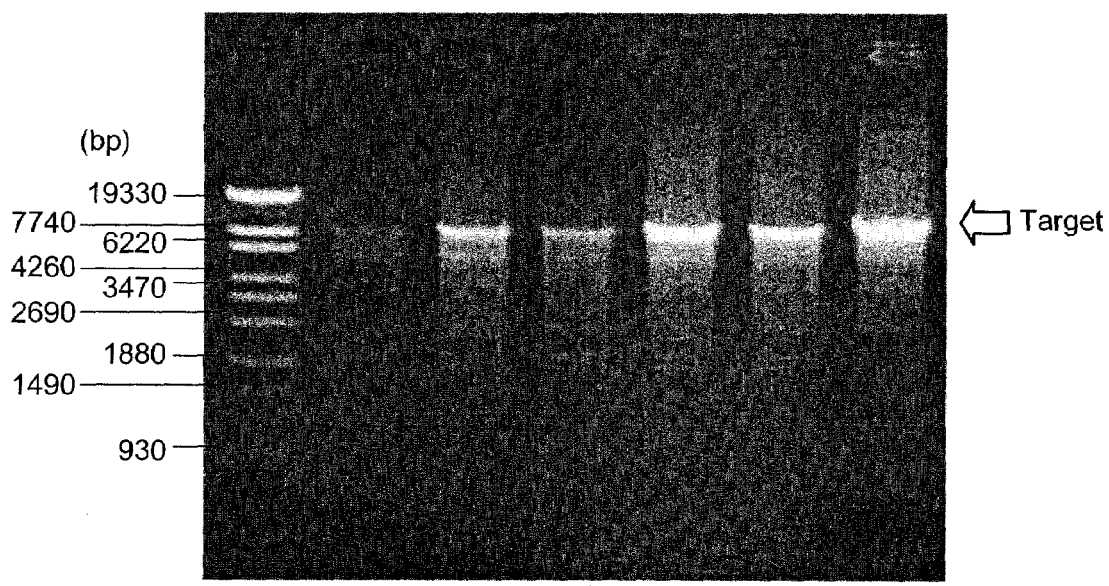
FIG. 23 is a view showing effects of adding PCNA13 to Deep Vent DNA polymerase for each extension time when the amplified length was 8.4 kb.

In the case of 2 kb amplification As shown in FIG. 22, the promotion of the reaction by the addition of PCNA13 was obviously recognized when the extension time is 0.5, 1 or 2 minutes. With the extension time of 3 minutes, the reaction was saturated regardless of the addition or no addition, but it was found that the amplified amount when PCNA13 was added with the extension time of 2 minutes indicated that the reaction was almost saturated.

In the case of 8.4 kb amplification

As shown in FIG. 23, the promotion effect (amplified amount, reaction rate) by the addition was observed with the extension time of 5, 7 and 9 minutes.

2.2.5: Effect of Adding PCNA13 to Pfu Turbo DNA Polymerase

Pfu Turbo DNA polymerase (Stratagene) is a product containing a heat resistant DNA polymerase derived from *Pyrococcus furiosus* with an additional PCR reaction accelerator referred to as ArchaeMaxx (registered trade name). It is known that dUTP accessorily produced during the PCR reaction inhibits the PCR reaction. ArchaeMaxx Factor is a factor to degrade dUTP, and the addition of this prevents the PCR reaction from being inhibited to result in enhancing the PCR reaction efficiency.

Upon evaluation, the PCR reaction solution having the standard composition was used except that PCNA13 was added to the solution. The reaction buffer (10× Cloned Pfu DNA polymerase reaction buffer; 200 mM Tris-HCl (pH 8.8), 100 mM $(NH_4)_2SO_4$, 100 mM KCl, 20 mM $MgSO_4$, 1% Triton X-100, 1 mg/mL BSA) attached to the product was used as the buffer. The composition of the PCR reaction solution is shown below.

TABLE 14

| Composition | Amount to be added | Final concentration |
| --- | --- | --- |
| Lambda DNA (20 ng/µL) | 1.25 µL | 0.5 ng/µL |
| Forward Primer (20 pmol/µL)[1] | 0.5 µL | 0.2 µM |
| Reverse Primer (20 pmol/µL)[1] | 0.5 µL | 0.2 µM |
| 10× Cloned Pfu DNA polymerase reaction Buffer | 5 µL | 1× |
| dNTP Mix (2.5 mM each) | 4 µL | 0.2 mM |
| Pfu Turbo DNA Polymerase (2.5 U/µL) | 1 µL | 0.05 U/µL |
| PCNA13 solution or buffer[2] | 0.3 µL | 0 or 0.6 ng/µL |
| Sterile water | 37.45 µL | |
| Total | 50 µL | |

[1] The combination of the forward primer and the reverse primer is changed depending on the length to be amplified. For the combination of the primers, see Tables 8 and 9.
[2] Neat concentration of PCNA 13; 100 ng/µL, Buffer; 25 mM TrisCl pH8.0, 50 mM NaCl, 50% Glycerol PCR reaction program In the case of 2 kb amplification 95° C. for 2 minutes-->(95° C. for 30 seconds-->55° C. for 30 seconds-->72° C. for one minute) 30 cycles-->72° C. for 10 minutes-->being kept at 4° C.

In the case of 8.4 kb amplification

92° C. for 2 minutes-->(92° C. for 10 seconds-->55° C. for 30 seconds-->68° C. for 8 minutes) 10 cycles-->(92° C. for 10 seconds-->55° C. for 30 seconds-->68° C. for 8 minutes+10 seconds/cycle) 20 cycles-->being kept at 4° C.

In the case of 15.8 kb amplification

92° C. for 2 minutes-->(92° C. for 10 seconds-->55° C. for 30 seconds-->68° C. for 15 minutes) 10 cycles-->(92° C. for 10 seconds-->55° C. for 30 seconds-->68° C. for 15 minutes+10 seconds/cycle) 20 cycles-->being kept at 4° C.

Electrophoresis

After completing the PCR reaction, 5 µL of 10× loading buffer (glycerol 50%, bromophenol blue 0.4%, Xylene cyanol 0.4%) was added to and mixed with 50 µL of the PCR reaction solution, and a specific amount of the mixture corresponding to 10 µL of the PCR reaction solution was then subjected to 1% agarose gel electrophoresis. As the electrophoresis marker, lambda/styI marker (Toyobo Co., Ltd.) was used.

Summary

Figure 24:
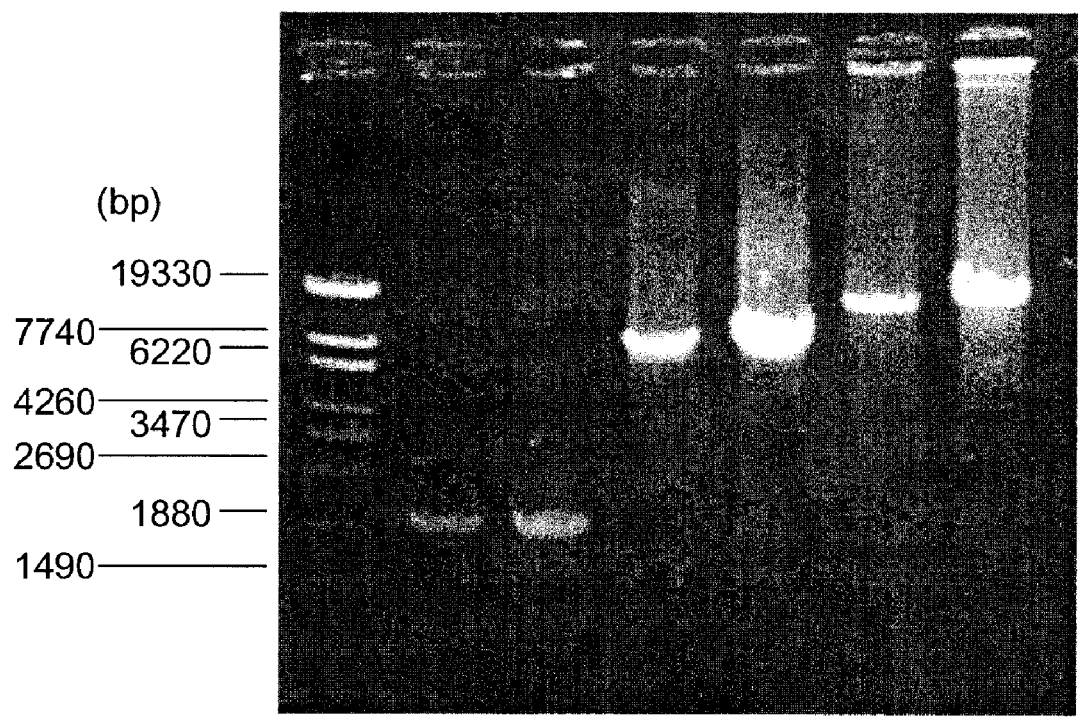
FIG. 24 is a view showing effects of adding PCNA13 to Pfu Turbo DNA polymerase.

As shown in FIG. 24, the promotion of the reaction rate and the increase of the amplified amount by the addition of PCNA13 were observed in any size examined in the PCR reaction.

2.2.6: Effect of Adding PCNA13 to KOD DNA Polymerase

KOD DNA polymerase (Toyobo Co., Ltd.) is a DNA polymerase derived from an ultrathermophilic archaebacterium, *Thermococcus.kodakaraensis* KOD1 strain, and has PCR fidelity about 50 times higher than Taq DNA polymerase because of having the strong 3'-->5' exonuclease activity (proof reading activity) in addition to the polymerase activity. Enzymes for highly accurate PCR derived from genus *Pyrococcus* distributed commercially tend to have slow extension rate, but this enzyme has the very fast extension rate which is about twice faster than that of Taq DNA polymerase. Thus, highly accurate PCR can be performed in a short period of time using this enzyme.

Upon evaluation, the PCR reaction solution having the standard composition was used except that PCNA13 was added to the solution. The reaction buffer (10×PCR buffer #1; 1.2M Tris-HCl pH 8.0, 60 mM $(NH_4)_2SO_4$, 100 mM KCl, 1% TritonX-100, 0.01% BSA or 10×PCR buffer #2; 1.2M Tris-HCl pH 8.8, 60 mM $(NH_4)_2SO_4$, 100 mM KCl, 1% TritonX-100, 0.01% BSA) attached to the product was used as the buffer. The composition of the PCR reaction solution is shown below.

TABLE 15

| Composition | Amount to be added | Final concentration |
|---|---|---|
| Lambda DNA (20 ng/μL) | 1.25 μL | 0.5 ng/μL |
| Forward Primer (20 pmol/μL)[1] | 1.25 μL | 0.5 μM |
| Reverse Primer (20 pmol/μL)[1] | 1.25 μL | 0.5 μM |
| 10x enclosed Buffer #1 or #2[2] | 5 μL | 1x |
| dNTP Mix (2.5 mM each) | 4 μL | 0.2 mM |
| 25 mM MgCl$_2$ | 2 μL | 1 mM |
| KOD DNA Polymerase (2.5 U/μL) | 0.28 μL | 0.014 U/μL |
| PCNA13 solution or buffer[3] | 0.3 μL | 0 or 0.6 ng/μL |
| Sterile water | 36.67 μL | |
| Total | 50 μL | |

[1]The combination of the forward primer and the reverse primer is changed depending on the length to be amplified. For the combination of the primers, see Tables 8 and 9.
[2]10x enclosed Buffer #1; 2 kb, #2; 8.4 kb, 15.8 kb
[3]Neat concentration of PCNA 13; 100 ng/μL, Buffer; 25 mM TrisCl pH8.0, 50 mM NaCl, 50% Glycerol PCR Reaction Program In the case of 2 kb amplification 94° C. for one minute-->(98° C. for 10 seconds-->68° C. for 12 seconds) 30 cycles-->72° C. for 3 minutes-->being kept at 4° C.

In the case of 8.4 kb and 15.8 kb amplification

94° C. for one minute-->(98° C. for 10 seconds-->68° C. for 2 minutes) 30 cycles-->72° C. for 3 minutes-->being kept at 4° C.

Electrophoresis

After completing the PCR reaction, 5 μL of 10× loading buffer (glycerol 50%, bromophenol blue 0.4%, Xylene cyanol 0.4%) was added to and mixed with 50 μL of the PCR reaction solution, and a specific amount of the mixture corresponding to 10 μL of the PCR reaction solution was then subjected to 1% agarose gel electrophoresis. As the electrophoresis marker, lambda/styI marker (Toyobo Co., Ltd.) was used.

Summary

Figure 25:
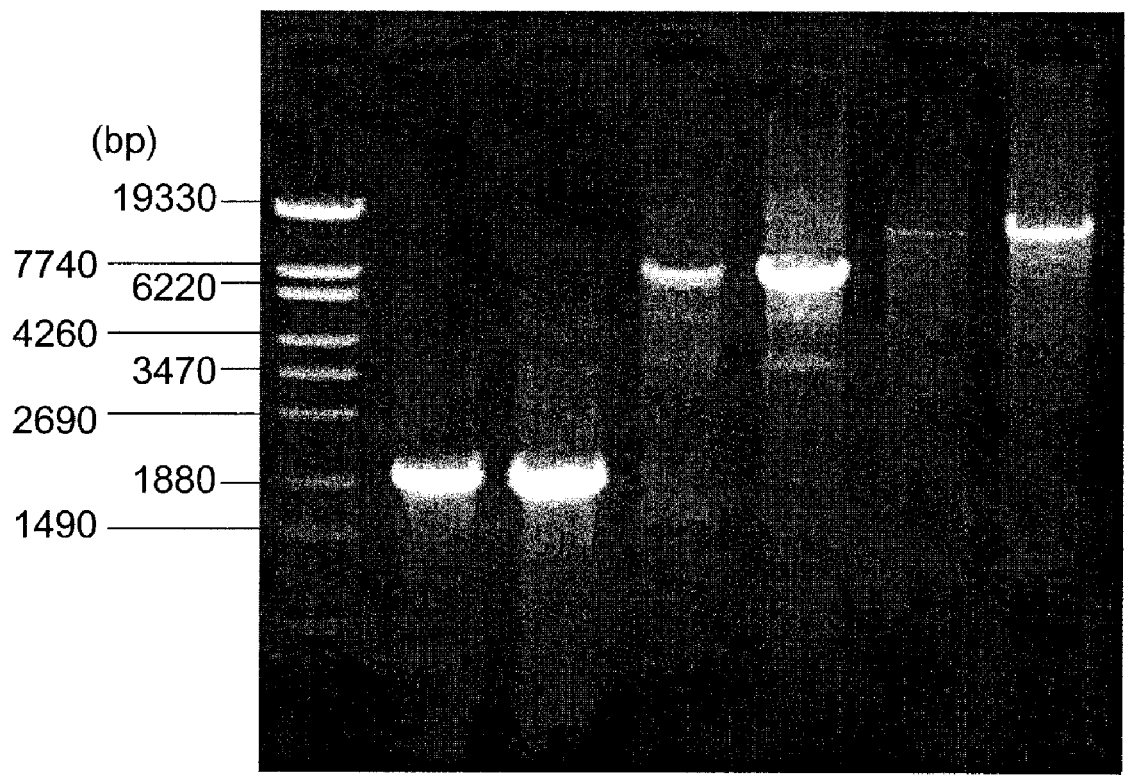
FIG. 25 is a view showing effects of adding PCNA13 to KOD DNA polymerase.

As shown in FIG. 25, the promotion of the reaction rate and the increase of the amplified amount by the addition of PCNA13 were observed in any size examined in the PCR reaction.

2.2.7: Effect of Adding PCNA13 to Pwo DNA Polymerase

Pwo DNA polymerase (Roche Diagnostics) is a DNA polymerase derived from a thermophilic archaebacterium *Pyrococcus woesei* strain, and has the PCR fidelity higher than Taq DNA polymerase because of having the strong 3'-->5' exonuclease activity (proof reading activity) in addition to the polymerase activity. Thus, PCR with high accuracy can be performed in a short time using this enzyme.

Upon evaluation, the PCR reaction solution having the composition recommended in the instructions by the manufacturer was used except that PCNA13 was added to the solution. The reaction buffer (10×PCR buffer; 100 mM Tris-HCl pH 8.85, 50 mM (NH$_4$)$_2$SO$_4$, 250 mM KCl, 20 mM MgSO$_4$) attached to the product was used as the buffer. The composition of the PCR reaction solution is shown below.

TABLE 16

| Composition | Amount to be added | Final concentration |
|---|---|---|
| Lambda DNA (20 ng/μL) | 1.25 μL | 0.5 ng/μL |
| Forward Primer (20 pmol/μL)[1] | 1.5 μL | 0.6 μM |
| Reverse Primer (20 pmol/μL)[1] | 1.5 μL | 0.6 μM |
| 10x PCR buffer with MgSO$_4$ | 5 μL | 1x |
| dNTP Mix (2.5 mM each) | 4 μL | 0.2 mM |
| Pwo DNA Polymerase (5 U/μL) | 0.14 μL | 0.014 U/μL |
| PCNA13 solution or buffer[2] | 0.3 μL | 0 or 0.6 ng/μL |
| Sterile water | 36.31 μL | |
| Total | 50 μL | |

[1]The combination of the forward primer and the reverse primer is changed depending on the length to be amplified. For the combination of the primers, see Tables 8 and 9.
[2]Neat concentration of PCNA 13; 100 ng/μL, Buffer; 25 mM TrisCl pH8.0, 50 mM NaCl, 50% Glycerol PCR reaction program In the case of 2 kb amplification 94° C. for one minute-->(98° C. for 10 seconds-->68° C. for 30 seconds or one minute) 30 cycles-->72° C. for 3 minutes-->being kept at 4° C.

In the case of 8.4 kb amplification

95° C. for 2 minutes-->(95° C. for 30 seconds-->60° C. for 30 seconds-->72° C. for 2 or 4 minutes) 30 cycles-->72° C. for 3 minutes-->being kept at 4° C.

Electrophoresis

After completing the PCR reaction, 5 μL of 10× loading buffer (glycerol 50%, bromophenol blue 0.4%, Xylene cyanol 0.4%) was added to and mixed with 50 μL of the PCR reaction solution, and a specific amount of the mixture corresponding to 10 μL of the PCR reaction solution was then subjected to 1% agarose gel electrophoresis. As the electrophoresis marker, lambda/styI marker (Toyobo Co., Ltd.) was used.

SUMMARY

Figure 26:
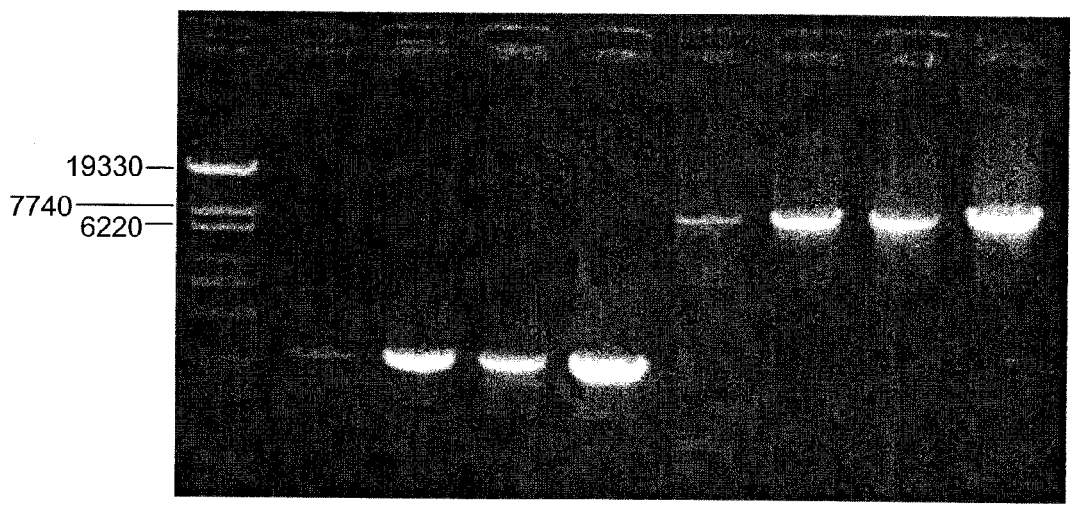
FIG. 26 is a view showing effects of adding PCNA13 to Pwo DNA polymerase.

As shown in FIG. 26, the promotion of the reaction rate and the increase of the amplified amount by the addition of PCNA13 were observed in any size examined of PCR products with any extension time examined.

As shown in the aforementioned Examples, it has been proved that PCNA13 excellently promotes extension activity of the representative commercially available seven DNA polymerases for PCR. It has been also shown that, although PCNA 13 used is the mutant of PCNA derived from *Pyrococcus furiosus*, PCNA 13 is effective for not only DNA polymerases derived from *Pyrococcus furiosus* but also DNA polymerases derived from different bacterial species.

3: Preparation of KOD-PCNA and KOD-RFC Proteins

A PCNA mutant protein preparation and an RFC protein preparation derived from *Thermococcus kodakaraensis* KOD1 strain were prepared by expressing the genes thereof in large amounts in *Escherichia coli* and purifying the proteins from expressing microbial cells.

3.1: Acquisition of Microbial Cell and Preparation of Genomic DNA

*Thermococcus kodakaraensis* KOD1 strain was obtained from JCM (JAPAN COLLECTION OF MICROORGANISMS) as 10 mL of a cultured liquid (JCM NO. 12,380). Microbial cells were collected by centrifuging this liquid at 6,000×g at 4° C. for 15 minutes. The collected microbial cells were suspended in 1 mL of TBS buffer (50 mM Tris-HCl pH 7.2, 150 mM NaCl), washed and collected by centrifugation at 15,000×g at 4° C. for 5 minutes.

The precipitate was dissolved in 100 μL of lytic buffer (50 mM Tris-HCl.pH 8.0, 50 mM EDTA.pH 8.0, 0.5% SDS), and incubated at 50° C. for 3 hours. Subsequently, 100 μL of phenol/chloroform was added thereto. This solution was centrifuged at 15,000×g at room temperature for 5 minutes to collect about 100 μL of the supernatant. The genomic DNA was collected from this supernatant using Mag Extractor Genome Kit (Toyobo Co., Ltd.) according to its manipulation manual.

3.2: Preparation of KOD-PCNA 3.2.1: Cloning of KOD-PCNA Gene

Figure 27:
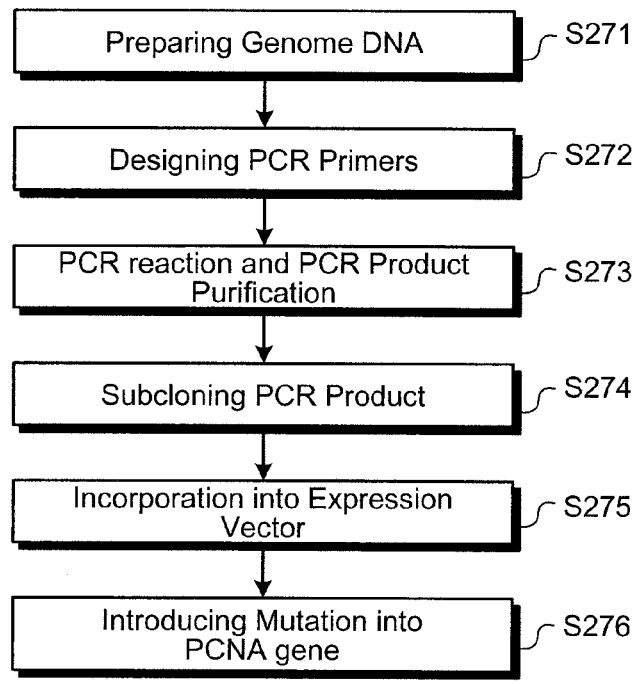
FIG. 27 is a view showing a flowchart for preparing an expression vector for a KOD-PCNA gene.

A KOD-PCNA gene was acquired by cloning using PCR (FIG. 27) with reference to GenBank ID BD182828 (SEQ ID NOS:31 and 32). The detail thereof will be described below.

3.2.1.1: PCR Primers

KOD-PCNA-F and KOD-PCNA-R were used for the amplification of the KOD-PCNA gene. This primer set was designed so as to amplify the region corresponding to the initiation codon methionine to the termination codon of the PCNA gene and further add the restriction enzymes NdeI and XhoI recognition sites to the 5' side. The sequence of each primer was shown in Table 17 (SEQ ID NOS:33 and 34).

TABLE 17

PCR primers for cloning KOD-PCNA

| Primer name | Primer sequence 5'==>3' | SEQ ID NO |
|---|---|---|
| KOD-PCNA-F | cca tat gcc gtt cga agt tgt ttt tga | 33 |
| KOD-PCNA-R | ctc gag tca ctc ctc aac gcg cgg | 34 |

3.2.1.2: Composition of PCR Reaction Solution

The PCR reaction solution has the following composition (amounts to be added to 50 μL of the reaction solution).
Template DNA*: 100 ng,
Primers: each 10 pmol,
dNTP: each 10 nmol,
Ex Taq**: 1.25 U and
10× Ex Taq buffer: 5 μL
were mixed, and sterilized water was added thereto up to the total volume of 50 μL.
(*template DNA: genomic DNA prepared in 3.1, **EX Taq: supplied from TAKARA BIO INC.)

3.2.1.3: Conditions for PCR

The PCR reaction was performed by using the reaction solution prepared in the aforementioned procedure and the PCR apparatus and using the program repeating 30 cycles of the reaction at 95° C. for 30 seconds-->55° C. for 30 seconds-->72° C. for one minute.

3.2.1.4: Purification of PCR Product

The PCR product obtained in the aforementioned procedure was subjected to 1% agarose gel electrophoresis, and stained with ethidium bromide. Subsequently a gel fragment containing a band around 750 bp was cut out under the ultraviolet light irradiation, and the PCR product in the gel fragment was purified using GFX PCR DNA and Gel Band Purification Kit (Amersham Bioscience) according to its manipulation manual.

3.2.1.5: Subcloning of PCR Product

The purified PCR product was ligated to pUC118-HincII/BAP (TAKARA BIO INC.) using TaKaRa BKL Kit (TAKARA BIO INC.) according to the manipulation manual. Escherichia.coli DH5α (TAKARA BIO INC.) was transformed with this ligated product, which was then seeded on the LB agar plate (containing 100 μg/mL of ampicillin, 40 μg/mL of IPTG, and 40 μg/mL of X-GAL), and cultured by leaving stand at 37° C. overnight to yield an E. coli clone having the PCR product.

An E. coli colony exhibiting the white color on the agar plate was cultured in 3 mL of the LB liquid medium (containing 100 μg/mL of ampicillin) with shaking at 37° C. overnight with shaking, and then a plasmid DNA was prepared according to the standard method.

3.2.1.6: Confirmation of Sequence by Sequencing

Concerning the aforementioned plasmid DNA, the DNA sequence inserted into the recognition site of the restriction enzyme HincII in the plasmid vector pUC118 was examined using the DNA sequencer. As a result, it was confirmed that the open reading frame of the KOD-PCNA gene is retained, the restriction enzyme, NdeI recognition sequence was added to the 5' end and the restriction enzyme, XhoI recognition sequence was added the 3' end in the inserted portion. This plasmid vector having the open reading frame of the KOD-PCNA gene was designated as pUC/KPC.

3.2.2: Construction of Expression Plasmid of KOD-PCNA Gene

The plasmid pUC/KPC was doubly cleaved with the restriction enzymes NdeI and XhoI to prepare a PCNA gene fragment. The gene fragment was inserted into the expression vector to produce the expression vector of KOD-PCNA.

3.2.2.1: Preparation of PCNA DNA Fragment

The plasmid pUC/KPC was doubly cleaved with restriction enzymes NdeI and XhoI in the following reaction system.
Plasmid DNA: 5 μg
10× Restriction enzyme buffer: 5 μL
Restriction enzyme NdeI: 5 units
Restriction enzyme XhoI: 5 units
Sterile water was added to the aforementioned mixture up to the total volume of 50 μL, and the plasmid DNA was cleaved with the restriction enzymes at 37° C. for 2 hours. After completing the reaction, the reaction product was run on 2% agarose gel electrophoresis. A band (around about 750 bp) corresponding to the KOD-PCNA gene was cut out and the PCNA DNA fragment was purified from the gel using GFX PCR DNA and Gel Band Purification Kit (Amersham Bioscience) according to its manipulation manual.

3.2.2.2: pET-21a Expression Vector

The vector DNA pET-21a (Novagen, US) was doubly cleaved with the restriction enzymes NdeI and XhoI by the following reaction.
Plasmid DNA: 2 μg
10× Restriction enzyme buffer: 5 μL
Restriction enzyme NdeI: 5 units
Restriction enzyme XhoI: 5 units
Sterile water was added to the aforementioned mixture up to the total volume of 50 μL, which was then left stand at 37° C. for 2 hours. After completing the reaction, the reaction product was run on 1% agarose gel electrophoresis. A band (around about 5.4 kb) corresponding to the straight form of the vector DNA pET-21a was cut out and the pET-21a DNA fragment was purified from the gel using GFX PCR DNA and Gel Band Purification Kit (Amersham Bioscience) according to its manipulation manual.

3.2.2.3: Ligation Reaction and Transformation

The KOD-PCNA DNA fragment (100 ng) and the pET-21a DNA fragment (50 ng) obtained in the aforementioned procedure were reacted using DNA Ligation Kit V2 (TAKARA BIO INC.) as follows.

PCNA DNA fragment: 100 ng
pET-21a DNA fragment: 50 ng
DNA Ligation Kit V2 enzyme solution: 5 μL Sterile water was added to the aforementioned mixture up to the total volume of 10 μL, which was then reacted at 16° C. for 30 minutes.

100 μL of *E. coli* BL21 (DE3) (Novagen) was transformed with this ligation product (3 μL). The solution of transformed *E. coli* was seeded on the LB agar plate (100 μg/mL ampicillin) and left stand to culture at 37° C. overnight. Three colonies in *E. coli* colonies formed on the agar plate were cultured with shaking in 3 mL of the LB liquid medium (containing 100 μg/mL ampicillin) at 37° C. overnight, and a plasmid DNA was prepared according to standard methods.

3.2.2.4: Confirmation of Sequence by Sequencing

Concerning the aforementioned plasmid DNA, the DNA sequence inserted in the plasmid vector pET-21a and the sequence in the vicinity of the inserted site were examined using the DNA sequencer. As a result, the open reading frame of the KOD-PCNA gene was completely inserted between NdeI and XhoI sites which were multicloning sites. This plasmid retaining the KOD-PCNA gene was designated as pKPCNA (FIG. 28).

Figure 28:
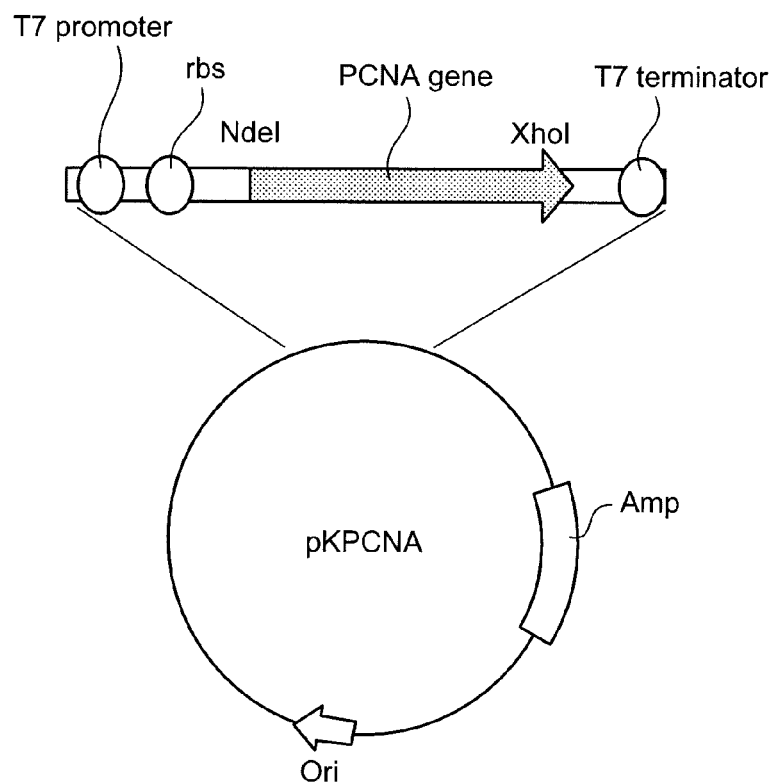
FIG. 28 is a view showing the expression plasmid for the KOD-PCNA gene.

As shown in FIG. 28, it was confirmed that the T7 promoter and rbs (ribosome binding site) which pET-21a had, the PCNA gene ORF (open reading frame) and the T7 terminator were aligned in this order in pKPCNA. It was expected that this plasmid would express the PCNA gene in the large amount.

3.2.3: Introduction of Mutation into KOD-PCNA Gene

For the purpose of producing the PCNA having a higher function, the amino acid in KOD-PCNA was substituted. The amino acid was substituted by substituting the base in the codon encoding that amino acid. An amino acid mutation was introduced into the site to be mutated shown in Table 18.

TABLE 18

| Mutated site of KOD-PCNA | |
| --- | --- |
| Mutant | Mutated site |
| KOD-PCNA01 | M73L |
| KOD-PCNA13 | M73L + E143R |

3.2.3.1: Introduction of Substitution Mutation

The mutation was introduced into the PCNA gene by utilizing the plasmid to be mutated, the oligo pair for introducing the mutation (SEQ ID NOS:35 to 38 in Table 19) and Quick Change II Site-Directed Mutagenesis Kit (Stratagene) according to its manipulation manual.

TABLE 19

| Primers for introducing mutation into KOD-PCNA | | |
| --- | --- | --- |
| Primer name | Primer sequence 5'==>3' | SEQ ID NO |
| KOD_M73L-F | C GAG ACA ATC GGC ATC AAC CTG GAC CAG TTC AAG | 35 |
| KOD_M73L-R | CTT GAA CTG GTC CAG GTT GAT GCC GAT TGT CTC G | 36 |

TABLE 19-continued

| Primers for introducing mutation into KOD-PCNA | | |
| --- | --- | --- |
| Primer name | Primer sequence 5'==>3' | SEQ ID NO |
| KOD_E143R-F | CTC GGT GAG GTT CTC AAG CGT GGC ATA AAG GAC GCT TC | 37 |
| KOD_E143R-R | GA AGC GTC CTT TAT GCC ACG CTT GAG AAC CTC ACC GAG | 38 |

After introducing the mutation, the DNA sequence was identified by sequencing to confirm that the DNA was introduced into the objective site and no mutation other than the objective one was present. The design for each PCNA mutant will be described below.

KOD-PCNA01

According to the report for the PCNA from *Pyrococcus furiosus* (Non-patent Document 6), the following has been reported: when the wild type Pfu-PCNA is prepared as the recombinant protein using *Escherichia coli* as the host, in addition to the original protein as a result of translation from Met, another protein of about 20 kDa with the N terminus beginning from the 73rd residue is produced as a byproduct, and thus a production efficiency of the objective protein is reduced. It has been also reported that when Met at position 73 is substituted with Leu using the gene engineering technique, the production of this protein of about 20 kDa is inhibited, and that the Pfu-PCNA produced in this way has the nature indistinguishable from the nature of the wild type PCNA protein. Both KOD-PCNA and Pfu-PCNA are composed of 249 amino acid residues in full length, 84.3% of the amino acid residues is completely identical. Further considering the existence of amino acids having similar nature, they have very high homology. Based on such a situation, the mutant M73L of KOD-PCNA obtained by substituting Met at position 73 in KOD-PCNA with Leu is addressed as the quasi-wild type in the present specification.

This mutant KOD_M73L was designated as KOD-PCNA01 and was prepared. KOD-PCNA01 was produced by using pKPCNA as a template and the oligo pair (KOD_M73L-F and KOD_M73L-R: SEQ ID NOS:35 and 36 in Table 19) for introducing the mutation.

KOD-PCNA13

In the case of PCNA from *Pyrococcus furiosus*, it has been known that the amino acid residue at position 143 is involved in the formation of the ion pair network when the monomers form the trimer (Non-patent Document 9). As demonstrated in the aforementioned Examples 1 and 2, our group has found that the reaction of DNA polymerase in the DNA synthesis is remarkably promoted by the mutant PCNA obtained by reversely changing the electric nature of the amino acid residue at this position. In the case of wild type PCNA from *Thermococcus* kodakaraensis, the amino acid residue corresponding to this position is glutamic acid (acidic amino acid), and the electric nature of the amino acid residue at this position can be completely changed by substituting this amino acid residue with arginine (basic amino acid residue. This mutant was produced for the purpose of examining the effect when this mutant is added to the DNA synthesis. Specifically, the mutant was produced by using the KOD-PCNA01-producing plasmid as a template and the oligonucleotides KOD_E143R-F and KOD_E143R-R for introducing the mutation (SEQ ID NOS:37 and 38 in Table 19).

3.2.3.2: Production of KOD-PCNA Expression Strains

*E. coli* BL21 CodonPlus (DE3)RIL (Stratagene) was transformed with the expression vectors of mutant PCNA obtained in the aforementioned procedure to yield an *E. coli* strain expressing mutant gene.

3.2.4: Purification of KOD-PCNA Protein

Figure 29:
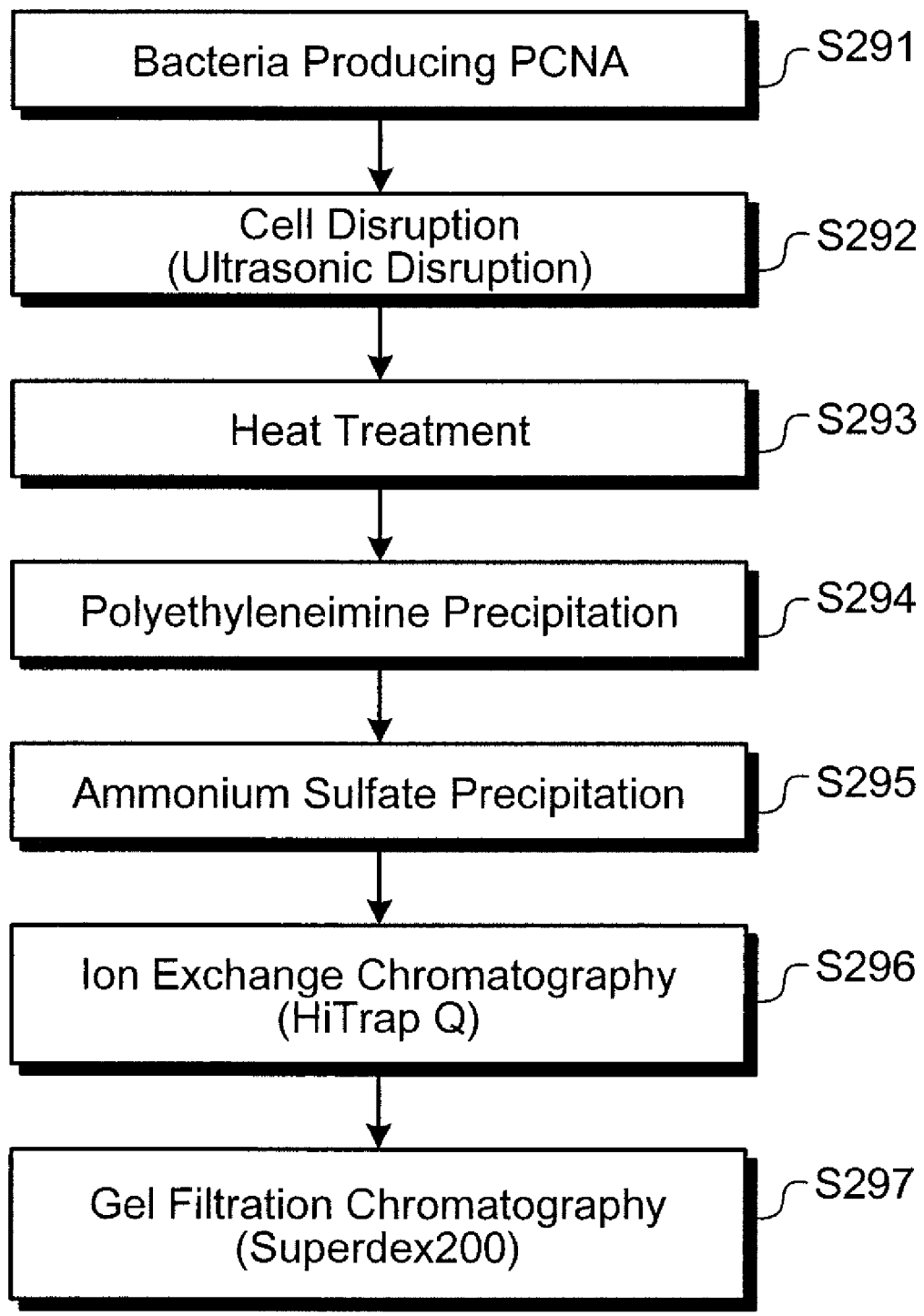
FIG. 29 is a view showing a flowchart for preparing a KOD-PCNA protein.

As shown in FIG. 29, preparations were obtained by collecting the microbial cells by centrifugation (S291), disrupting the microbial cells (ultrasonic disruption, S292), boiling for 5 minutes (S293), performing the polyethyleneimine precipitation (S529), performing the ammonium sulfate precipitation (S295), performing the ion exchange chromatography (S296, using HiTrap Q as a column) and performing the gel filtration chromatography (S297, using Superdex 200). It was confirmed by SDS-PAGE that both preparations assured the purity of 90% or more.

3.2.4.1: Culturing of Microbial Cells and Induction of KOD-PCNA Expression

Each mutant PCNA-expressing strain was cultured with shaking in 1.5 liters of the LB medium (containing 50 μg/mL of ampicillin) at 37° C. The expression was induced by adding IPTG (isopropyl-β-D-thiogalactopyranoside) at a final concentration of 0.1 mM when $OD_{600}$ at the logarithmic growth phase was 0.3 to 0.5, and after inducing the expression, the culturing was continued for about 3 hours. Microbial cells after the culturing were collected by centrifugation (4° C., 6,000×g, 6 minutes).

3.2.4.2: Disruption of Microbial Cells

The microbial cells precipitated by centrifugation were suspended in 25 mL of buffer B (50 mM Tris-HCl pH 8.0, 0.1 M NaCl, 0.1 mM EDTA, 10% glycerol, 0.5 mM DTT), and disrupted by ultrasonic treatment.

3.2.4.3: Treatment with Heat

A solution of the disrupted microbial cells was boiled for 5 minutes and then centrifuged (18,500×g, 4° C., 25 minutes), to collect a supernatant.

3.2.4.4: Polyethyleneimine Precipitation

Polyethyleneimine (Sigma P-3143) and NaCl at final concentrations of 0.2% (w/v) and 0.58 M, respectively, were added to the supernatant, which was then stirred on ice for 30 minutes. This solution was centrifuged (18,500×g, 4° C., 25 minutes) to yield a supernatant.

3.2.4.5: Ammonium Sulfate Precipitation 5.61 g of ammonium sulfate (final concentration of 80%) was added to 10 mL of the supernatant and stirred on ice for 30 minutes to precipitate a protein. 80 mL of 50 mM Tris-HCl (pH 8.5) buffer in which ammonium sulfate had been 80% saturated was added to this solution and the precipitation was collected by centrifugation (30,000×g, 4° C., 25 minutes). Subsequently, this precipitation was dissolved in buffer C (50 mM Tris-HCl pH 8.0, 0.1M NaCl) and the resulting solution was dialyzed against the same buffer C.

3.2.4.6: Ion Exchange Chromatography

The dialyzed sample was subjected to the ion exchange chromatography (HiTrap Q; Amersham Bioscience) using AKTA explorer 10S (Amersham Bioscience). The sample was eluted with the linear gradient of 0.1 to 0.8 M NaCl/17.5 mL at a flow rate of 1 mL/minute to yield peak fractions of KOD-PCNA01 and KOD-PCNA13.

3.2.4.7: Gel Filtration Chromatography

Each peak fraction in HiTrap Q ion exchange chromatography was further purified by gel filtration chromatography using Superdex 200 (Amersham Bioscience) to obtain the preparation for the subsequent assays.

Figure 30:
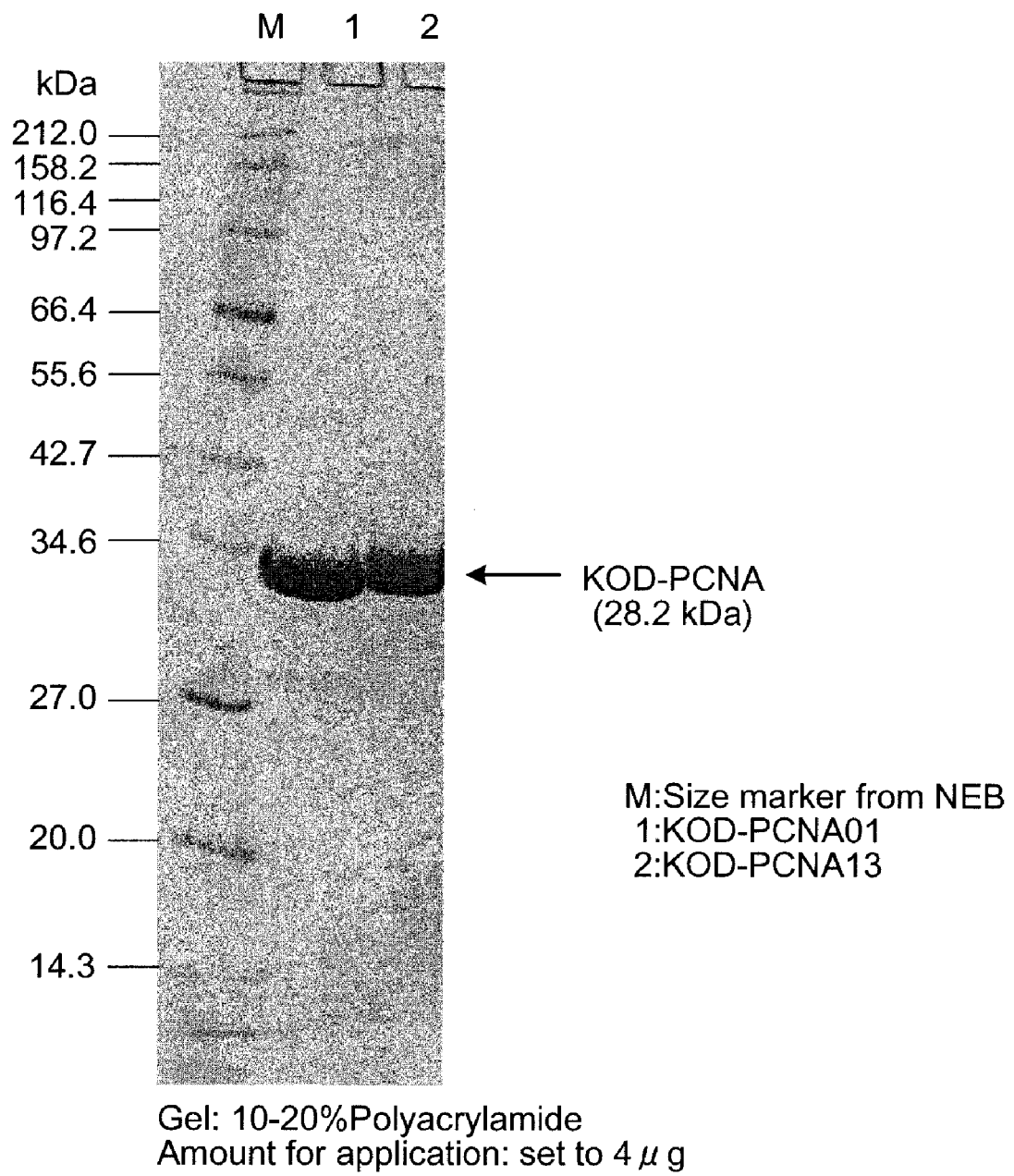
FIG. 30 is a view showing a result of polyacrylamide gel electrophoresis of a KOD-PCNA protein preparation.

The obtained preparation was applied onto the polyacrylamide gel electrophoresis to confirm the molecular size and good purification of the preparation (FIG. 30).

3.3: Purification of KOD-RFC

RFC from *Thermococcus kodakaraensis* KOD is composed of two subunits RFCL and RFCS, which are located in tandem on the genome. Upon producing the RFC protein preparation, an RFCL gene and an RFCS gene were individually inserted in distinct expression vectors, and the respective expression vectors were introduced into the same host to express simultaneously. The expression plasmid was produced with reference to Non-patent Document 10. The detail thereof will be described below.

Figure 31:
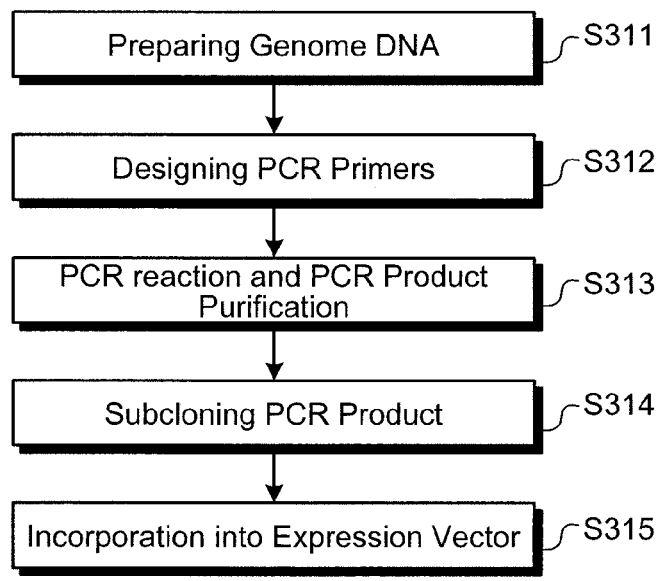
FIG. 31 is a view showing a flowchart for preparing an expression vector for a KOD-RFCL gene.

3.3.1: Cloning of KOD-RFCL Gene and Construction of expression plasmid (FIG. 31)

The KOD-RFCL (GenBank ID; 182,830) gene was obtained by PCR using the KOD genome as the template (SEQ ID NO:39).

3.3.1.1: PCR Primers

KOD-RFCL-F primer and KOD-RFCL-R primer (SEQ ID NOS:40 and 41 in Table 20) were used as the primers for PCR. For convenience of cloning, the restriction enzyme NdeI recognition site was added to the KOD-RFCL-F primer, and the restriction enzyme XhoI recognition site was added to the KOD-RFCL-R primer.

TABLE 20

Primers for cloning KOD-RFCL

| Primer name | Primer sequence 5'==>3' | SEQ ID NO |
|---|---|---|
| KOD-RFCL-F | cca tat gac gga agt ccc atg ggt tg | 40 |
| KOD-RFCL-R | ctc gag tca ctt ctt gag gaa gtc gaa cag | 41 |

3.3.1.2: Composition of PCR Reaction Solution

The KOD genomic DNA prepared in the aforementioned 3.1 was used as the template for PCR. The PCR reaction solution has the following composition (amounts to be added to 50 μL of the reaction solution).

Template DNA: 100 ng,
Primers: each 10 pmol,
dNTP: each 10 nmol,
Ex Taq*: 1.25 U and
10× Ex Taq buffer: 5 μL were mixed, and sterilized water was added thereto up to the total volume of 50 μL.
(*supplied from TAKARA BIO INC.)

3.3.1.3: Reaction Conditions for PCR

The PCR reaction was performed by using the reaction solution prepared in the aforementioned procedure and the PCR apparatus and using the program repeating 30 cycles of the reaction at 95° C. for 30 seconds-->55° C. for 30 seconds-->72° C. for one minute

3.3.1.4: Purification of PCR Product

The PCR product obtained in the aforementioned procedure was subjected to 1% agarose gel electrophoresis, and stained with ethidium bromide. Subsequently a gel fragment containing a band around 1.5 kb was cut out under the ultraviolet light irradiation, and the PCR product in the gel fragment was purified using GFX PCR DNA and Gel Band Purification Kit (Amersham) according to its manipulation manual.

3.3.1.5: Subcloning of PCR Product

The purified PCR product was ligated to pUC118-HincII/BAP using TaKaRa BKL kit (TAKARA BIO INC.) according to the manipulation manual. *Escherichia coli* DH5α

(TAKARA BIO INC.) was transformed with this ligated PCR product, which was then seeded on the LB agar plate (containing 100 µg/mL of ampicillin, 40 µg/mL of IPTG, and 40 µg/mL of X-GAL), and cultured by leaving stand at 37° C. overnight to yield an *E. coli* clone having the PCR product.

An *E. coli* colony exhibiting the white color on the agar plate was cultured in 3 mL of the LB liquid medium (containing 100 µg/mL of ampicillin) at 37° C. overnight with shaking, and then a plasmid DNA was prepared according to the standard method.

3.3.1.6: Confirmation of Sequence by Sequencing

Concerning the aforementioned plasmid DNA, the DNA sequence inserted into the recognition site of the restriction enzyme HincII in the plasmid vector pUC118 was examined using the DNA sequencer. As a result, it was confirmed that the open reading frame of the KOD-RFCL gene was retained, the restriction enzyme NdeI recognition sequence was added to the 5' end and the restriction enzyme XhoI recognition sequence was added the 3' end in the inserted portion. This plasmid vector was designated as pUC118/KRFCL.

3.3.1.7: Preparation of Expression Plasmid of KOD-RFCL

The plasmid pUC118/KRFCL was doubly cleaved with the restriction enzymes NdeI and XhoI to prepare an RFCL gene fragment. The gene fragment was inserted into the expression vector to produce the expression vector of KOD-RFCL.

3.3.1.8 Preparation of RFCL DNA Fragment

The plasmid pUC118/KRFCL was doubly cleaved with the restriction enzymes NdeI and XhoI in the following reaction system.

Plasmid DNA: 5 µg
10× Restriction enzyme buffer: 5 µL
Restriction enzyme NdeI: 5 units
Restriction enzyme XhoI: 5 units Sterile water was added to the aforementioned mixture up to the total volume of 50 µL, which was then cleaved with the restriction enzymes at 37° C. for 2 hours. After completing the reaction, the reaction product was run on 1% agarose gel electrophoresis. A band (around about 1.5 kb) corresponding to the KOD-RFCL gene was cut out and the RFCL DNA fragment was purified from the gel using GFX PCR DNA and Gel Band Purification Kit (Amersham Bioscience) according to its manipulation manual.

3.3.1.9: Expression Vector pET-29a

The vector DNA pET-29a (Novagen, US) was doubly cleaved with the restriction enzymes NdeI and XhoI by the following reaction.

Plasmid DNA: 2 µg
10× Restriction enzyme buffer: 5 mL
Restriction enzyme NdeI: 5 units
Restriction enzyme XhoI: 5 units Sterile water was added to the aforementioned mixture up to the total volume of 50 µL, which was then left stand at 37° C. for 2 hours. After completing the reaction, the reaction product was run on 1% agarose gel electrophoresis. A band (around about 5.4 kb) corresponding to the straight form of the vector pET-29a was cut out and the pET-29a DNA fragment was purified from the gel using GFX PCR DNA and Gel Band Purification Kit (Amersham Bioscience) according to its manipulation manual.

3.3.1.10: Ligation Reaction and Transformation

The KOD-RFCL DNA fragment (100 ng) and the pET-29a DNA fragment (50 ng) obtained in the aforementioned procedure were reacted using DNA Ligation Kit V2 (TAKARA BIO INC.) as follows.

RFCL DNA fragment: 100 ng
pET-29a DNA fragment: 50 ng
DNA Ligation Kit V2 enzyme solution: 5 µL Sterile water was added to the aforementioned mixture up to the total volume of 10 µL, which was then reacted at 16° C. for 30 minutes.

100 µL of *E. coli* BL21 (DE3) (Novagen) was transformed with this ligation product (3 µL). The solution of transformed *E. coli* was seeded on the LB agar plate (containing 30 µg/mL of kanamycin) and left stand to culture at 37° C. overnight. Three colonies in *E. coli* colonies formed on the agar plate were cultured with shaking in 3 mL of the LB liquid medium (containing 30 µg/mL of kanamycin) at 37° C. overnight, and a plasmid DNA was prepared according to standard methods.

3.3.1.11: Confirmation of Sequence by Sequencing

Concerning the aforementioned plasmid DNA, the DNA sequence inserted in the plasmid vector pET-29a and the sequence in the vicinity of the inserted site were examined using DNA sequencer. As a result, in all plasmid DNA, the ORF (open reading frame) of the KOD-RFCL gene was completely inserted between NdeI and XhoI sites which were multicloning sites. This plasmid retaining the KOD-RFCL gene was designated as pKRFCL (FIG. 32).

Figure 32:
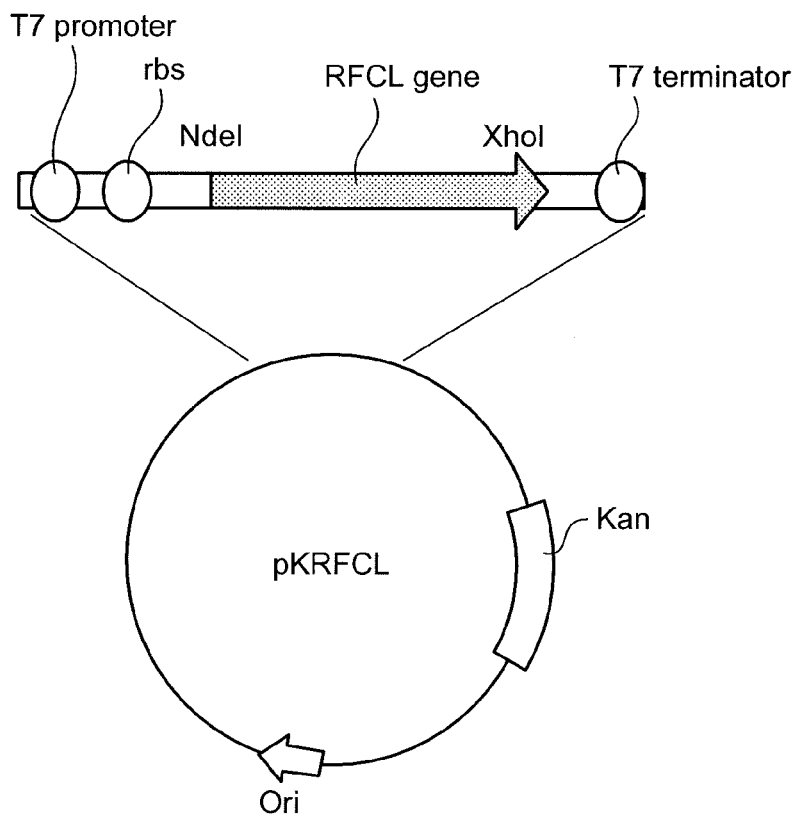
FIG. 32 is a view showing the expression plasmid for the KOD-RFCL gene.

As shown in FIG. 32, it was confirmed that the T7 promoter and rbs (ribosome binding site) which pET-29a had, the open reading frame of the RFCL gene and the T7 terminator were aligned in this order in pKRFCL. It was expected that this plasmid would express the RFCL gene in the large amount.

3.3.2: Cloning of KOD-RFCS gene and Construction of Expression Plasmid

According to Non-patent Document 10, it has been reported that the KOD-RFCS gene (GenBank ID: BD182,829) is encoded by 2,601 bases in full length and contains one intein, and that the N terminal extein is encoded by 177 bases and the C terminal extein is encoded by 804 bases (not including the termination codon). The base sequence of the KOD-RFCS gene (mature type sequence obtained by removing the intein portion) is shown in SEQ ID NO:42 in Sequence Listing.

Figure 33:
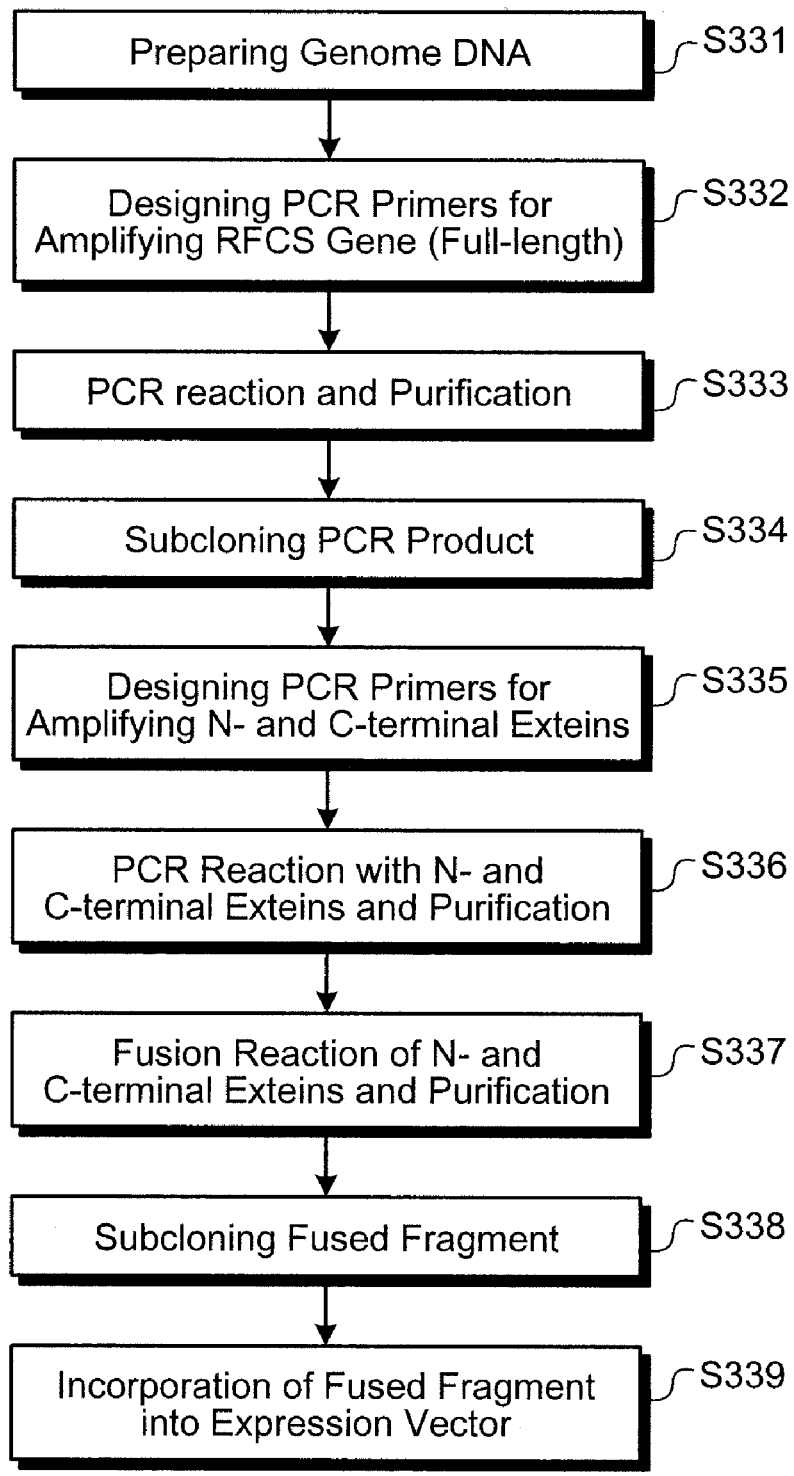
FIG. 33 is a view showing a flowchart for preparing an expression vector for a KOD-RFCSm (mature RFCS) gene.

Upon producing the RFCS expression vector as shown in FIG. 33, first the KOD-RFCS gene in full length including the intein was cloned (S331 to S334) using PCR, subsequently two extein fragments were individually amplified by PCR reaction (S335 to S336), and then the mature RFCS (also referred to as RFCSm) where the two exteins had been bound and the intein had been removed was prepared. This mature RFCS was incorporated in the expression vector (S337 to S339).

3.3.2.1: Cloning of RFCS Gene in Full Length Including Intein
3.3.2.1.1: PCR Primers KOD-RFCS-F primer and KOD-RFCS-R primer (SEQ ID NOS:43 and 44 in Table 21) were used as the PCR primers.

TABLE 21

Primers for cloning KOD-RFCS

| Primer name | Primer sequence 5'==>3' | SEQ ID NO |
|---|---|---|
| KOD-RFCS-F | atg tcc gag gaa gtg aag gaa g | 43 |
| KOD-RFCS-R | tca ctt acc cat aat cgt gaa ctg | 44 |

3.3.2.1.2: Composition for PCR Reaction

The KOD genomic DNA prepared in the aforementioned 3.1 was used as the template for PCR. The PCR reaction solution has the following composition (amounts to be added to 50 µL of the reaction solution).

Template DNA: 100 ng,
Primers: each 10 pmol,
dNTP: each 10 nmol,
Ex Taq*: 1.25 U and
10× Ex Taq buffer: 5 µL were mixed, and sterilized water was added thereto up to the total volume of 50 µL.

(*supplied from TAKARA BIO INC.)

3.3.2.1.3: Reaction Conditions for PCR

The PCR reaction was performed by using the reaction solution prepared in the aforementioned procedure and the PCR apparatus and using the program repeating 30 cycles of the reaction at 95° C. for 30 seconds-->55° C. for 30 seconds-->72° C. for one minute.

3.3.2.1.4: Purification of PCR Product

The PCR product obtained in the aforementioned procedure was subjected to 1% agarose gel electrophoresis, and stained with ethidium bromide. Subsequently a gel fragment containing a band around 2.6 kb was cut out under the ultraviolet light irradiation, and the PCR product in the gel fragment was purified using GFX PCR DNA and Gel Band Purification Kit (Amersham) according to its manipulation manual.

3.3.2.1.5: Subcloning of PCR Product

The purified PCR product was ligated to pUC118-HincII/BAP (TAKARA BIO INC.) using TaKaRa BKL Kit (TAKARA BIO INC.) according to the manipulation manual. *Escherichia coli* DH5α (TAKARA BIO INC.) was transformed with this ligated PCR product, which was then seeded on the LB agar plate (containing 100 µg/mL of ampicillin, 40 µg/mL of IPTG, and 40 µg/mL of X-GAL), and cultured by leaving stand at 37° C. overnight to yield an *E. coli* clone having the PCR product.

An *E. coli* colony exhibiting the white color on the agar plate was cultured in 3 mL of the LB liquid medium (containing 100 µg/mL of ampicillin) at 37° C. overnight with shaking, and then a plasmid DNA was prepared according to the standard method.

3.3.2.1.6: Confirmation of Sequence by Sequencing

Concerning the aforementioned plasmid DNA, the DNA sequence inserted in the restriction enzyme HincII recognition site of the plasmid vector pUC118 was examined using the DNA sequencer. As a result, the inserted portion completely comprises the base sequence of two exteins in the RFCS gene, and this plasmid was designed as pUC/KRFCS.

3.3.2.2: Binding of Exteins (Removal of Intein)

3.3.2.2.1: Primers for Binding Exteins

RFCS-Nde-F primer and RFCS-Ex1-R primer (SEQ ID NOS:45 and 48 in Table 22) were prepared as the PCR primers for the N terminal extein. RFCS-Ex2-F primer and RFCS-Sal-R primer (SEQ ID NOS:47 and 46 in Table 22) were prepared as the PCR primers for the C terminal extein. For the purpose of performing the cloning easily, the restriction enzyme NdeI sequence was added to the 5' end of the RFCS-Nde-F primer, and the restriction enzyme SalI sequence was added to 5' end of RFCS-Sal-R primer. The complementary sequences utilized when the two extein fragments were fused by PCR were provided in the RFCS-Ex1-R primer and the RFCS-Ex2-F primer.

TABLE 22

Primers for binging KOD-RFCS exteins (for removal of intein)

| Primer name | Primer sequence 5'==>3' | SEQ ID NO |
|---|---|---|
| RFCS-Nde-F | cca tat gtc cga gga agt gaa gga ag | 45 |
| RFCS-Sal-R | gtc gac tca ctt acc cat aat cgt gaa ctg | 46 |
| RFCS-Ex2-F | cgt cgg gaa gac aac cgc tgc act ggc ttt ag | 47 |
| RFCS-Ex1-R | cag cgg ttg tct tcc cga cgc cgg gtg gc | 48 |

3.3.2.2.2: Composition of PCR Reaction Solution

The PCR reaction for amplifying two exteins was performed using the following composition (amounts to be added to 50 µL of the reaction system).

pUC/KRFCS DNA: 50 ng
Primers: each 10 pmol
dNTP: each 10 nmol
Ex Taq*: 1.25 U and
10× Ex Taq buffer: 5 µL were mixed, and sterilized water was added thereto up to the total volume of 50 µL.

(*supplied from TAKARA BIO INC.)

3.3.2.2.3.: Reaction Conditions for PCR

The PCR reaction was performed by using the reaction solution prepared in the aforementioned procedure and the PCR apparatus and using the program repeating 30 cycles of the reaction at 95° C. for 30 seconds-->55° C. for 30 seconds-->72° C. for one minute.

3.3.2.2.4: Purification of PCR Product

PCR products obtained in the aforementioned procedure were subjected to 2% agarose gel electrophoresis, and stained with ethidium bromide. A band of about 180 bases was observed in the product of PCR with the set of the RFCS-Nde-F primer and the RFCS-Ex1-R primer. A band of about 800 bases was observed in the product of PCR with the set of the RFCS-Ex2-F primer and the RFCS-Sal-R primer. The gel fragment containing each band was cut out under the ultraviolet light irradiation, and the PCR product in the gel fragment was purified using GFX PCR DNA and Gel Band Purification Kit (Amersham) according to its manipulation manual.

3.3.2.2.5: PCR Fusion Reaction

The PCR products of two exteins were fused by subjecting them to PCR in one tube using one set of the primers to yield the gene fragment encoding the mature RFCS. The detail thereof will be described below.

An annealing reaction of two extein PCR products was performed with the following composition.

N terminal extein fragment: 2 µL (corresponding to 50 ng),
C terminal extein fragment: 2 µL (corresponding to 50 ng) and
10× Ex Taq buffer: 5 µL.

Sterile water was added to the aforementioned composition up to the total volume of 44.5 µL.

The aforementioned mixture was heated at 95° C. for 3 minutes, and slowly cooled down to 37° C. over 30 minutes.

The followings were added to the aforementioned reaction solution.

dNTP: 5 μL (each 10 nmol) and
Ex Taq*: 0.5 μL (2.5 U).

This mixture was reacted at 72° C. for 10 minutes. (*supplied from TAKARA BIO INC.)

10 pmol each of RFCS-Nde-F primer and RFCS-Sal-R primer was added to the aforementioned mixture, and the PCR reaction was performed using the program repeating 30 cycles of the reaction at 95° C. for 30 seconds-->55° C. for 30 seconds-->72° C. for one minute.

3.3.2.2.6: Cleavage with Restriction Enzymes and Purification of PCR Product

The PCR product obtained in the aforementioned procedure was purified by ethanol precipitation according to the standard method. The purified DNA fragment was doubly cleaved with the restriction enzymes NdeI and SalI.

PCR product: corresponding to 1 μg
10× Restriction enzyme buffer: 5 μL
Restriction enzyme NdeI: 5 units
Restriction enzyme SalI: 5 units Sterile water was added to the aforementioned composition up to the total volume of 50 μL, and the PCR product was cleaved with the restriction enzymes at 37° C. for 2 hours. After completing the reaction, the reaction product was run on 2% agarose gel electrophoresis. A band (around about 1 kb) supposed to contain the fused fragment of two inteins (encoding the mature RFCS) was cut out, and the fragment was purified using GFX PCR DNA and Gel Band Purification Kit (Amersham Bioscience).

3.3.2.2.7: Cleavage of Expression Vector pET-21a with Restriction Enzymes

The vector DNA pET-21a (Novagen) was doubly cleaved with the restriction enzymes NdeI and SalI.

Plasmid DNA: 2 μg
10× Restriction enzyme buffer: 5 μL
Restriction enzyme NdeI: 5 units
Restriction enzyme SalI: 5 units Sterile water was added to the aforementioned mixture up to the total volume of 50 μL, which was then left stand at 37° C. for 2 hours. After completing the reaction, the reaction product was run on 1% agarose gel electrophoresis. A band (around about 5.4 kb) corresponding to the straight form of the vector DNA pET-21a was cut out and the pET-21a DNA fragment was purified from the gel using GFX PCR DNA and Gel Band Purification kit (Amersham Bioscience) according to its manipulation manual.

3.3.2.2.8: Ligation Reaction and Transformation

The DNA fragment of about 1 kb (100 ng) predicted to be the fused fragment of two inteins (encoding the mature RFCS) and the pET-21a DNA fragment (50 ng) obtained in the aforementioned procedure were reacted using DNA Ligation Kit V2 (TAKARA BIO INC.) as follows.

1 kb DNA fragment: 100 ng
pET-21a DNA fragment: 50 ng
DNA Ligation Kit V2 enzyme solution: 5 μL Sterile water was added to the aforementioned mixture up to the total volume of 10 μL, which was then reacted at 16° C. for 30 minutes.

100 μL of *E. coli* BL21 (DE3) (Novagen) was transformed with this ligation product (3 μL). The solution of transformed *E. coli* was seeded on the LB agar plate (containing 100 μg/mL of ampicillin) and left stand to culture at 37° C. overnight. Three colonies in *E. coli* colonies formed on the agar plate were cultured with shaking in 3 mL of the LB liquid medium (containing 100 μg/mL of ampicillin) at 37° C. overnight, and a plasmid DNA was prepared according to standard methods.

3.3.2.2.9: Confirmation of Sequence by Sequencing

Concerning the aforementioned plasmid DNA, the DNA sequence inserted in the plasmid vector pET-21a and the sequence in the vicinity of the inserted site were examined using the DNA sequencer. As a result, the sequence of mature RFCSm (984 bases) binding two exteins (containing no intein) was identified between NdeI site and SalI site which were multicloning sites (designated as pKRFCSm).

Figure 34:
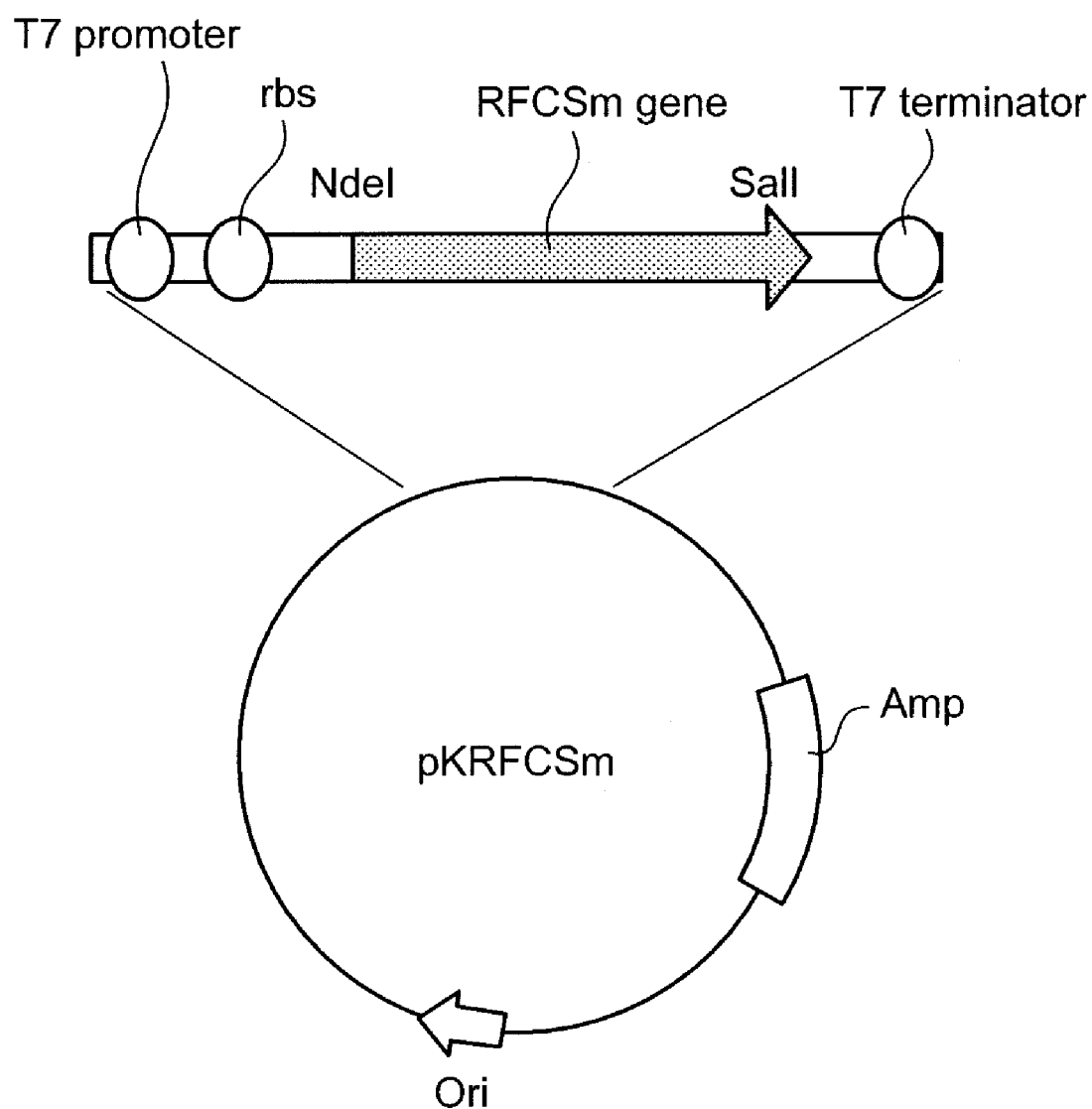
FIG. 34 is a view showing the expression plasmid for the KOD-RFCS gene.

As shown in FIG. 34, it was confirmed that the T7 promoter and rbs (ribosome binding site) which pET-21a had, the mature RFCS gene open reading frame and the T7 terminator were aligned in this order in pKRFCSm. It was expected that this plasmid would express the mature RFCS gene in the large amount.

3.3.3: Preparation of KOD-RFC Expression Strain

*Escherichia coli* BL21-CodonPlus (DE3)-RIL was simultaneously transformed with pKRFCL and pKRFCSm, and the expression strain having both plasmids was obtained by double selection of the transformant with ampicillin and kanamycin.

3.3.4: Purification of KOD-RFC Protein

Figure 35:
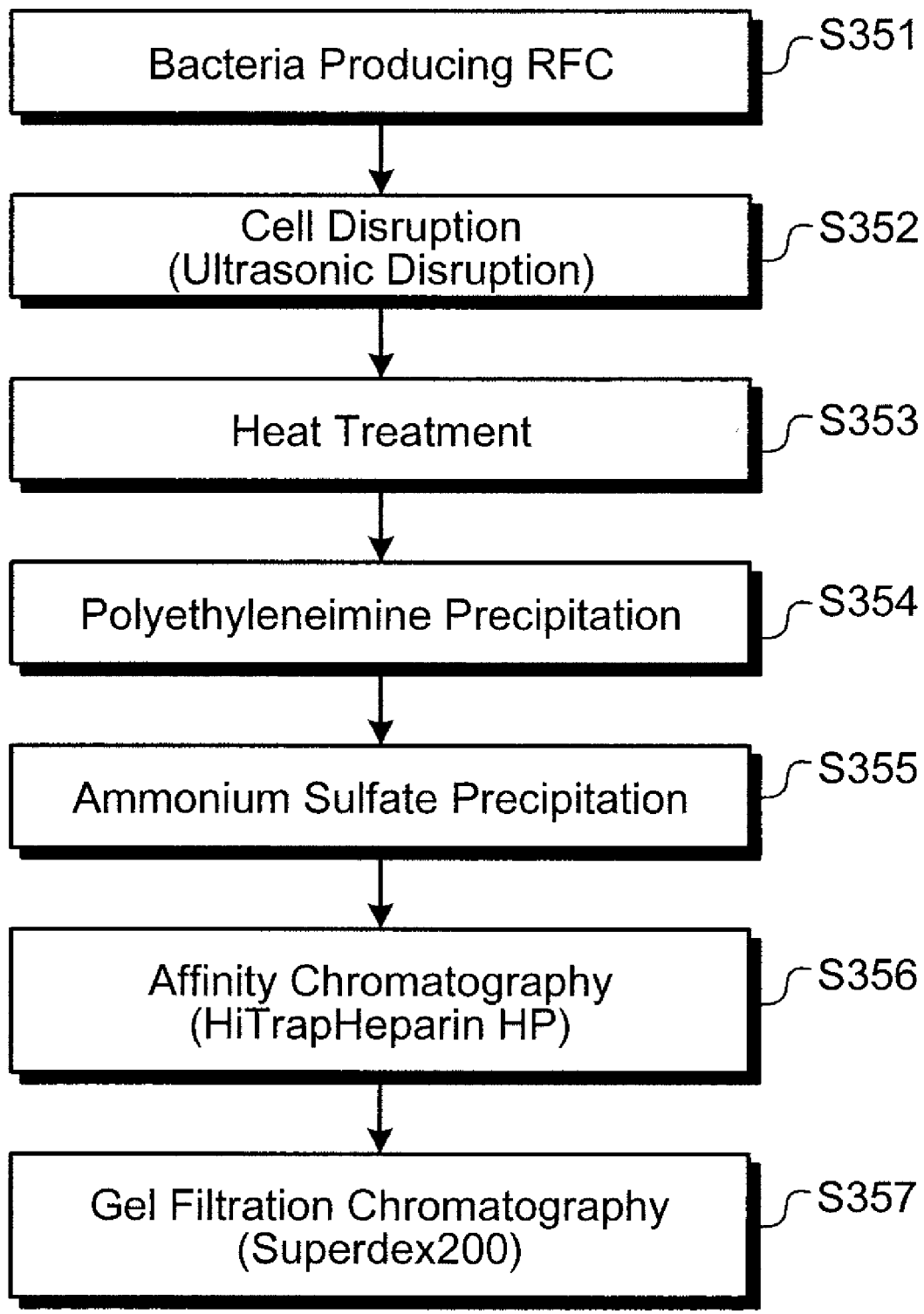
FIG. 35 is a view showing a flowchart for preparing a KOD-RFC protein.

As shown in FIG. 35, a preparation was obtained by collecting the microbial cells by centrifugation (S351), disrupting the microbial cells (ultrasonic disruption, S352), boiling for 5 minutes (S353), performing the polyethyleneimine precipitation (S354), performing the ammonium sulfate precipitation (S355), performing the affinity chromatography (S356, using HiTrap Heparin HP as a column) and performing the gel filtration chromatography (S357, using Superdex 200). It was confirmed by SDS-PAGE that the purity of 90% or more was assured in all preparations.

3.3.4.1: Culturing of Microbial Cells and Induction of Expression

The aforementioned expression strain was cultured with shaking in 1.5 liters of the LB medium (containing 50 μg/mL of ampicillin and 30 μg/mL of kanamycin) at 37° C. The expression was induced by adding IPTG (isopropyl-β-D-thiogalactopyranoside) at a final concentration of 0.1 mM when $OD_{600}$ at the logarithmic growth phase was 0.3 to 0.5, and after inducing the expression, the culturing was continued for about 3 hours. Microbial cells after the culturing were collected by centrifugation (4° C., 6,000×g, 6 minutes).

3.3.4.2: Disruption of Microbial Cells

The microbial cells precipitated by centrifugation were suspended in 25 mL of the buffer B (aforementioned), and disrupted by ultrasonic treatment.

3.3.4.3: Treatment with Heat

A disrupted microbial cell solution was boiled for 5 minutes, and subsequently centrifuged (18,500×g, 4° C., 25 minutes to collect the supernatant.

3.3.4.4: Polyethyleneimine Precipitation

Polyethyleneimine (Sigma P-3143) was added at a final concentration of 0.18% (w/v), which was then stirred on ice for 30 minutes. This solution was centrifuged (18,500×g, 4° C., 25 minutes) to yield a supernatant.

3.3.4.5: Ammonium Sulfate Precipitation 5.61 g of ammonium sulfate (final concentration of 80%) was added to 10 mL of the supernatant and stirred on ice for 30 minutes to precipitate a protein. The precipitation was collected by centrifugation (18,500×g, 4° C., 25 minutes). Subsequently, this precipitation was dissolved in the buffer C (aforementioned) and the resulting solution was dialyzed against the same buffer C.

3.3.4.6: Affinity Chromatography

The dialyzed sample was purified using HiTrap Heparin HP column (Amersham Bioscience).

The sample was eluted with the linear gradient of 0.1 to 0.8 M of NaCl/17.5 mL at the flow rate of 1 mL/minute to yield a peak fraction.

3.3.4.7: Gel Filtration Chromatography

Figure 36:
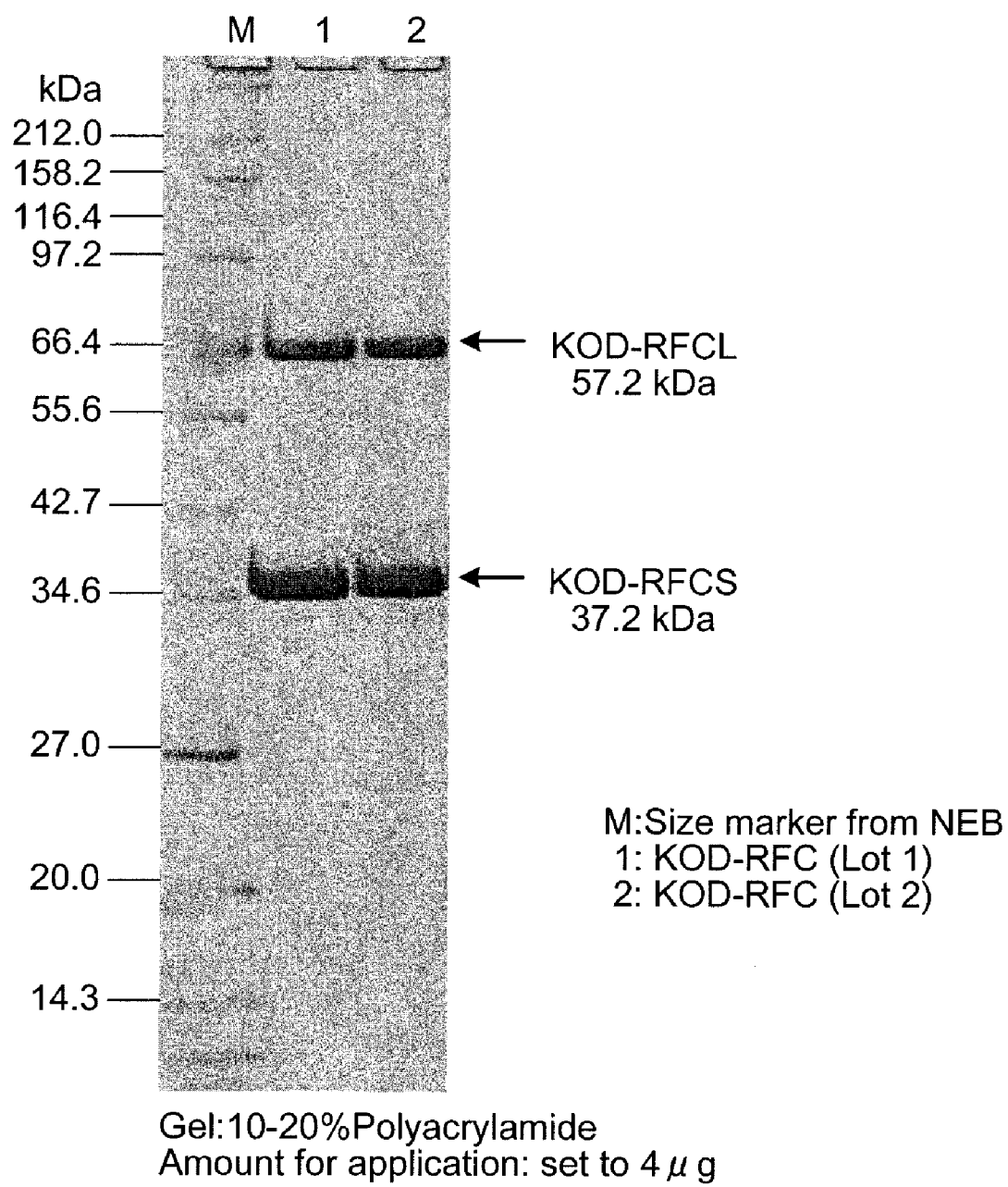
FIG. 36 is a view showing a result of polyacrylamide gel electrophoresis of a KOD-RFC protein preparation.

The peak fraction in the HiTrap Heparin affinity chromatography was further purified by gel filtration chromatography using Superdex 200 (aforementioned) to obtain a preparation for assays. The resulting preparation was applied onto the polyacrylamide gel electrophoresis to confirm the molecular size and good purification of the preparation (FIG. 36).

4: Evaluation of KOD-PCNA Mutant

The effect of the PCNA mutant prepared in the aforementioned procedure on the DNA amplification system, particularly the PCR reaction system was examined. Specifically, the PCR reaction was performed with the addition of the PCNA mutant alone, RFC alone or the combination thereof, or with the addition of none of them to the PCR reaction system. The level of the amplification of the target region were compared by subjecting the PCR product to the electrophoresis. Two commercially available DNA polymerases for PCR, KOD DNA polymerase (Toyobo Co., Ltd.) and Pyrobest DNA polymerase (TAKARA BIO INC.) were used for the PCR reaction.

4.1: Effect of Adding KOD-PCNA to KOD DNA Polymerase

KOD DNA polymerase is a DNA polymerase derived from the thermophilic archaebacterium, *Thermococcus.kodakaraensis* KOD-1 strain. The KOD DNA polymerase is a so-called α-type DNA polymerase having the strong 3'-->5' exonuclease activity (proof reading activity) in addition to the polymerase activity, and exhibits the PCR fidelity higher than Taq DNA polymerase generally used because of having the 3'-->5' exonuclease activity. Other α-type highly accurate enzymes for PCR often have the slow extension rate. However, it has been reported that the present enzyme has the very fast extension rate (Non-patent Document 11).

4.1.1: Template DNA and Reaction Primers

Lambda DNA (GenBank accession 02459) was used as the template DNA. The target sequence for PCR amplification was the sequence from 23,119 to 25,142 in the lambda DNA. The sequences of the primers used at that time were shown in Table 8, and were also shown in Table 23 additionally.

TABLE 23

| Primers for PCR assay | | |
|---|---|---|
| Primer name | Primer sequence 5'==>3' | SEQ ID NO |
| F02 | GTC GTT TCT GCA AGC TTG GC | 25 |
| R03 | CCG AGA TAA AAA CAA ACC CGC | 28 |

4.1.2: Composition of Reaction Solution

The composition of the reaction solution was shown in Tables 24 and 25.

TABLE 24

| Composition | Amount to be added | Final concentration |
|---|---|---|
| Lambda DNA (20 ng/μL) | 1.25 μL | 0.5 ng/μL |
| F02 Primer (20 pmol/μL) | 1.25 μL | 0.5 μM |
| R03 Primer (20 pmol/μL) | 1.25 μL | 0.5 μM |
| 10x enclosed Buffer #1 | 5 μL | 1x |
| dNTP Mix (2.5 mM each) | 4 μL | 0.2 mM |
| 25 mM MgCl$_2$ | 2 μL | 1 mM |
| KOD DNA Polymerase (2.5 U/μL) | 0.28 μL | 0.014 U/μL |
| Accessory protein solution (see Table 25) | 1.1 μL | — |
| Sterile water | 33.87 μL | — |
| Total | 50 μL | |

TABLE 25

| | Composition of accessory protein solution | KOD-PCNA01 (100 ng/μl) | KOD-PCNA13 (100 ng/μl) | KOD-RFC (500 ng/μl) | Buffer* |
|---|---|---|---|---|---|
| 1 | No KOD-PCNA nor KOD-RFC | 0 μL | 0 μL | 0 μL | 1.1 μL |
| 2 | KOD-PCNA01 (0.6 ng/μL) | 0.3 μL | 0 μL | 0 μL | 0.8 μL |
| 3 | KOD-PCNA01 (0.6 ng/μL) + KOD-RFC (4 ng/μL) | 0.3 μL | 0 μL | 0.4 μL | 0.4 μL |
| 4 | KOD-PCNA01 (0.6 ng/μL) + KOD-RFC (8 ng/μL) | 0.3 μL | 0 μL | 0.8 μL | 0 μL |
| 5 | KOD-PCNA13 (0.6 ng/μL) | 0 μL | 0.3 μL | 0 μL | 0.8 μL |
| 6 | KOD-PCNA13 (0.6 ng/μL) + KOD-RFC (4 ng/μL) | 0 μL | 0.3 μL | 0.4 μL | 0.4 μL |
| 7 | KOD-PCNA13 (0.6 ng/μL) + KOD-RFC (8 ng/μL) | 0 μL | 0.3 μL | 0.8 μL | 0 μL |

*Buffer: 25 mM Tris-HCl pH8.0, 50 mM NaCl, 50% Glycerol 4.1.3: PCR Program

The aforementioned reaction solution was reacted in the following program.

Reaction at 94° C. for one minute-->(98° C. for 5 seconds-->68° C. for 15 seconds) 30 cycles-->being kept at 4° C.

4.1.4: Electrophoresis

After completing the PCR reaction, 5 µL of 10× loading buffer (glycerol 50%, bromophenol blue 0.4%, Xylene cyanol 0.4%) was added to and mixed with 50 µL of the PCR reaction solution, and 10 µL in 50 µL of the reaction solution was then subjected to 1% agarose gel electrophoresis. As the electrophoresis marker, lambda/styI marker (Toyobo Co., Ltd.) was used. The results are shown in FIG. 37.

4.1.5: Results

Figure 37:
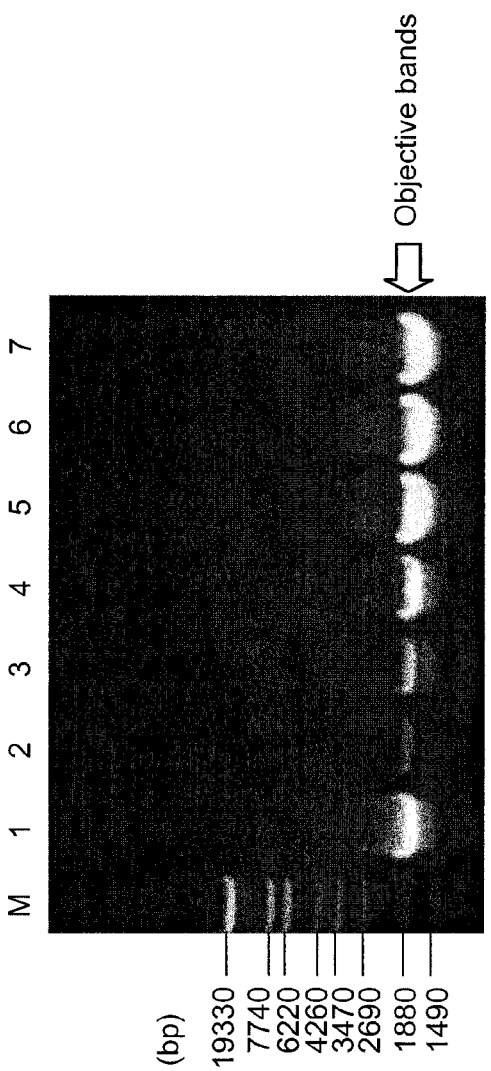
FIG. 37 is a view showing effects of adding a KOD-PCNA mutant and KOD-RFC to KOD DNA polymerase.

The results were shown in FIG. 37. Under these experimental conditions, the good extension and amplification can be observed with KOD DNA polymerase alone (lane 1).

When the quasi-wild type PCNA01 was added, the reaction inhibition was observed (lane 2), but when RFC was further added and the amount of added RFC was increased, the inhibition was offset and the extension and amplification at the same level as in the case of no addition were observed (lanes 3 and 4). Meanwhile, when KOD-PCNA13 was added, the good extension and amplification not depending on the addition of KOD-RFC were observed. This effect was better than those when no accessory protein was added and when KOD-PCNA01 was added in combination with RFC.

4.2: Effect of Adding KOD-PCNA to Pyrobest DNA Polymerase

Effect of addition of various PCNA mutants on Pyrobest DNA Polymerase (TAKARA BIO INC.), a commercially distributed DNA synthesis enzyme derived from genus *Pyrococcus*, was examined using the PCR reaction system. Pyrobest DNA Polymerase is a heat resistant a type DNA polymerase derived from *Pyrococcus* sp. and having 3'-->5' exonuclease activity (proof reading activity). This enzyme is characterized by performing a highly accurate amplification equivalent to that by Pfu DNA polymerase derived from *Pyrococcus furiosus*, and Vent DNA polymerase.

4.2.1: Template DNA and Reaction Primers

The same template DNA and primers as in the aforementioned evaluation of KOD DNA polymerase were used.

4.2.2: Composition of Reaction Solution

The compositions of the reaction solutions were shown in Tables 26 and 27

TABLE 26

| Composition | Amount to be added | Final concentration |
|---|---|---|
| Lambda DNA (20 ng/µL) | 1.25 µL | 0.5 ng/µL |
| F02 Primer (20 pmol/µL) | 0.5 µL | 0.2 µM |
| F03 Primer (20 pmol/µL) | 0.5 µL | 0.2 µM |
| 10× enclosed Buffer II | 5 µL | 1× |
| dNTP Mix (2.5 mM each) | 4 µL | 0.2 mM |
| Pyrobest DNA Polymerase (5 U/µL) | 0.25 µL | 0.025 U/µL |
| Accessory protein solution (see Table 27) | 1.3 µL | — |
| Sterile water | 37.2 µL | — |
| Total | 50 µL | |

TABLE 27

| | Composition of accessory protein solution | KOD-PCNA01 (400 ng/µl) | KOD-PCNA13 (400 ng/µl) | KOD-RFC (1400 ng/µl) | buffer* |
|---|---|---|---|---|---|
| 1 | No KOD-PCNA nor KOD-RFC | 0 µl | 0 µl | 0 µl | 1.3 µl |
| 2 | KOD-PCNA01 (2.4 ng/µl) | 0.3 µl | 0 µl | 0 µl | 1.0 µl |
| 3 | KOD-PCNA01 (2.4 ng/µl) + KOD-RFC (14 ng/µl) | 0.3 µl | 0 µl | 0.5 µl | 0.5 µl |
| 4 | KOD-PCNA01 (2.4 ng/µl) + KOD-RFC (28 ng/µl) | 0.3 µl | 0 µl | 1.0 µl | 0 µl |
| 5 | KOD-PCNA13 (2.4 ng/µl) | 0 µl | 0.3 µl | 0 µl | 1.0 µl |

*Buffer: 25 mM Tris-HCl pH8.0, 50 mM NaCl, 50% Glycerol 4.2.3: PCR Program

The aforementioned reaction solution was reacted in the following program.

94° C. for one minute-->(98° C. for 5 seconds-->68° C. for 1.5 minutes) 30 cycles-->being kept at 4° C.

4.2.4: Electrophoresis

After completing the PCR reaction, 5 µL of 10× loading buffer (glycerol 50%, bromophenol blue 0.4%, Xylene cyanol 0.4%) was added to and mixed with 50 µL of the PCR reaction solution, and 10 µL in 50 µL of the reaction solution was then subjected to 1% agarose gel electrophoresis. As the electrophoresis marker, lambda/styI marker (Toyobo Co., Ltd.) was used. The results are shown in FIG. 38.

4.2.5: Results

Figure 38:
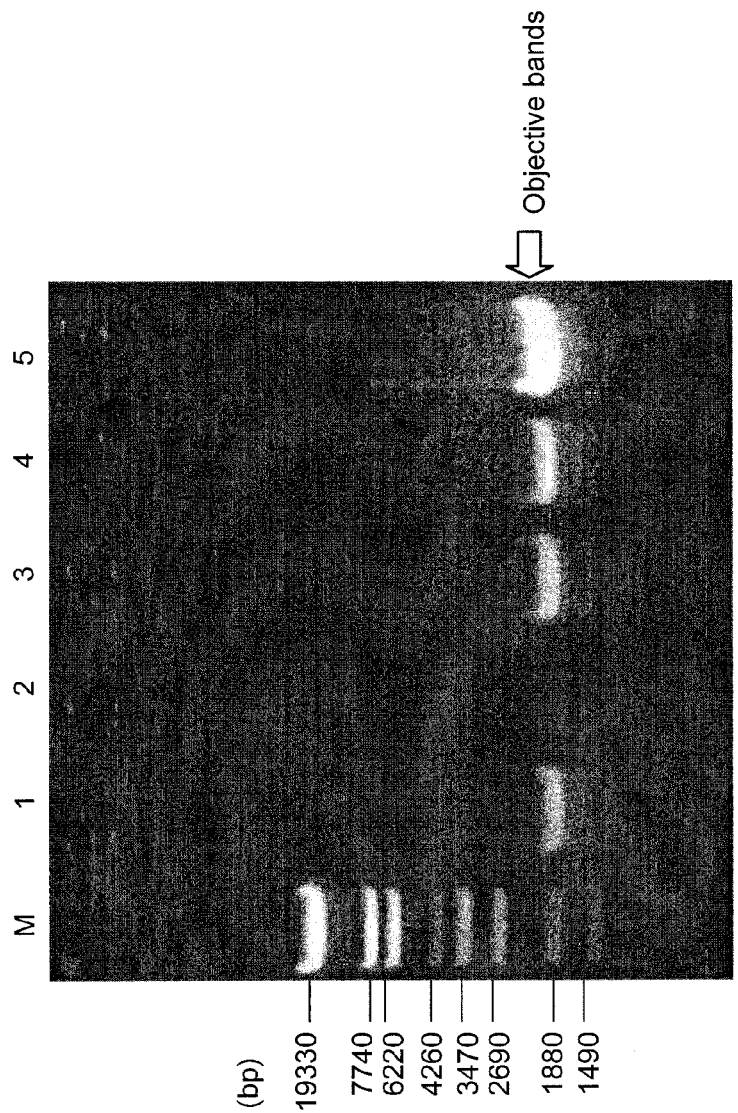
FIG. 38 is a view showing effects of adding the KOD-PCNA mutant and KOD-RFC to Pyrobest.

The results were shown in FIG. 38. Under these experiment conditions, the extension and amplification can be observed with Pyrobest DNA polymerase alone (lane 1). When the quasi-wild type PCNA01 was added, the reaction inhibition was observed and no band was detected (lane 2), but when the amount of added RFC was increased, the inhibition was offset and the extension and amplification at the same level as in the case of no addition were observed (lanes 3 and 4). Meanwhile, when KOD-PCNA13 was added, good extension and amplification were observed even when no RFC was added, and this effect exhibited better extension and amplification than in the other 4 conditions (lane 5).

4.3: Summary

It was found by the aforementioned experiments that KOD-PCNA13 promoted the PCR reaction of the representative two PCR enzymes. This reaction not only did not require the addition of RFC but also was better in promoting activity than in the case of adding the wild type in combination with RFC. It was proven by the aforementioned results that the excellent effect could be obtained by introducing the identical mutation into not only PCNA derived from *Pyrococcus furiosus* but also PCNA derived from *Thermococcus* kodakaraensis KOD1 strain. In the present invention, it was demonstrated that the identification of the amino acid residue in the interface region of the PCNA monomer of the present invention not only was effective for PCNA derived from *Pyrococcus furiosus* but also was applicable to PCNA having the same structural context.

5: Measurement of Fidelity in Addition Reaction of Pfu-PCNA

The effect of adding Pfu-PCNA to the PCR reaction on template fidelity was examined as to Pyrobest DNA polymerase (supplied from TAKARA BIO INC., hereinafter sometimes abbreviated simply as "Pyrobest") which was the commercially available PCR enzyme with high fidelity. Pyrobest is a DNA polymerase derived from the archaebacterium belonging to genus *Pyrococcus* and has the 3'-->5' exonuclease, which works as the proof reading activity.

Figure 39:
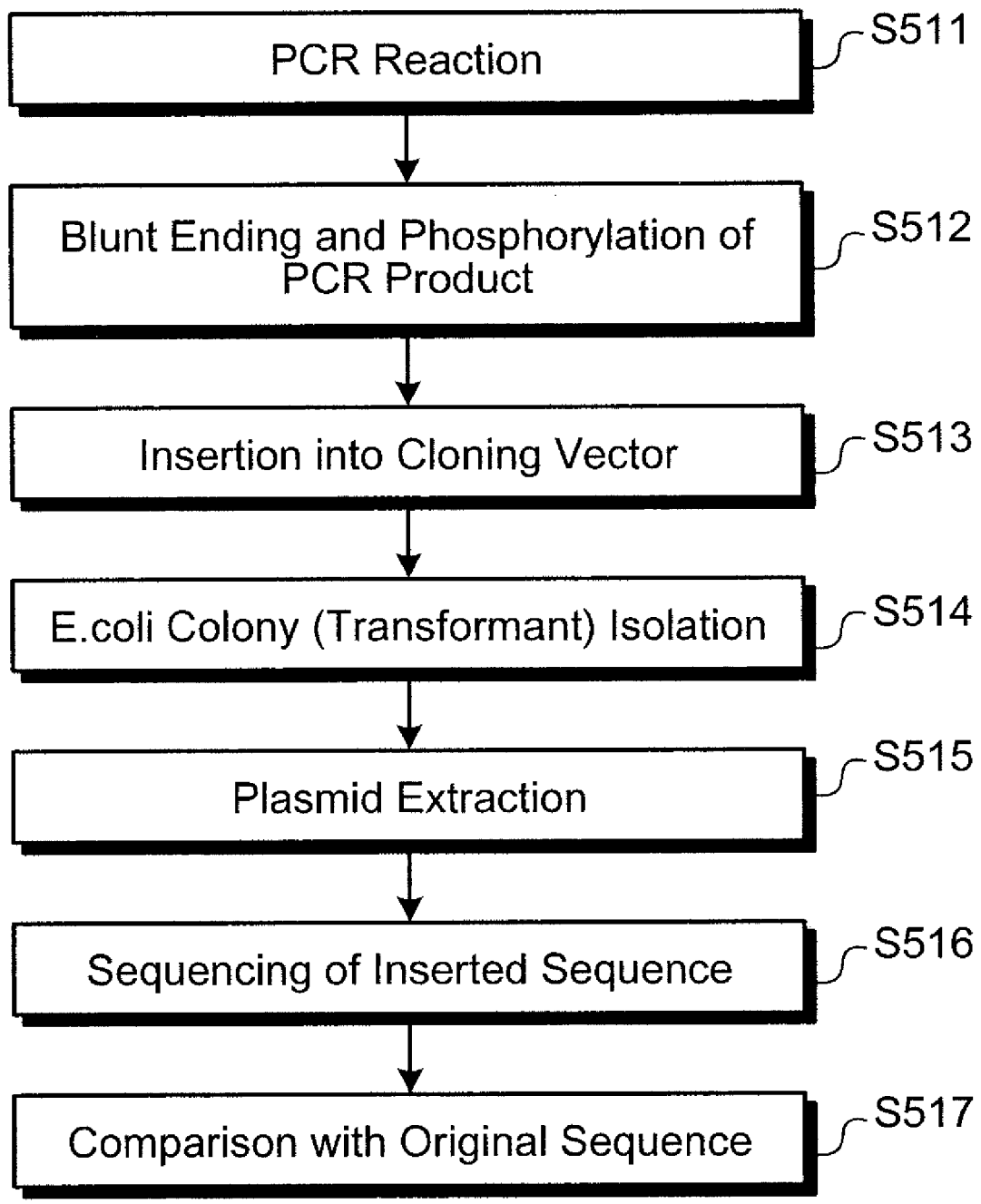
FIG. 39 is a view showing a flowchart for measuring fidelity to a PCR template.

The fidelity was obtained by examining the sequence of the PCR product and comparing it with the template sequence. An outline was shown in FIG. 39. The PCR reaction was performed using Pyrobest alone or in combination with Pfu-PCNA13 (S511), the end of the amplified DNA fragment was blunted and phosphorylated (S512), this fragment was cloned into a plasmid vector (S513), *Escherichia coli* was transformed with the plasmid vector and the colony was isolated, and the plasmid was extracted (S514, S515). A part (500 bp) of the inserted sequence in each plasmid was examined by the DNA sequencer (S516), and the result was compared with the template sequence to calculate a frequency of error occurrence (S517).

5.1: PCR Reaction 5.1.1: Combination of PCR Enzyme and Pfu-PCNA13

The case of performing the PCR reaction with Pyrobest alone and the case of performing the PCR reaction with Pyrobest in combination with Pfu-PCNA13 were examined. As the control for them, the PCR reaction with TaKaRa Taq (TAKARA BIO INC., hereinafter sometimes abbreviated simply as "Taq") alone was also examined. Taq is a PolI type PCR enzyme generally used, does not have the 3'-->5' exonuclease activity, and is described to have lower fidelity than the α-type PCR enzyme having the same activity.

5.1.2: Target Region of Template

Lambda DNA (GenBank accession 02459) was used as the template of the PCR reaction, and seven regions were targeted to the examination. The location on the lambda DNA and the size of each region, and the combination of the primers used for amplifying each region were shown in Table 28, and the primer sequences were shown in Table 29.

TABLE 28

| Fragment ID | Amplified region in lambda DNA | Amplified size (bp) | Forward primer | Reverse primer |
| --- | --- | --- | --- | --- |
| 1 | 17,973-19,022 | 1,050 | F23 | R25 |
| 2 | 19,001-20,050 | 1,050 | F25 | R27 |
| 3 | 23,619-24,654 | 1,036 | F09 | R11 |
| 4 | 24,634-25,696 | 1,063 | F11 | R15 |
| 5 | 26,894-27,492 | 599 | F14 | R04 |
| 6 | 40,460-41,185 | 1,026 | F16 | R17 |
| 7 | 42,532-43,613 | 1,082 | F19 | R21 |

TABLE 29

| Primer name | Start Position | End Position | Primer sequence 5'==>3' | SEQ ID NO |
| --- | --- | --- | --- | --- |
| F09 | 23,619 | 23,637 | AGC CTT TGC CTC GCT ATA C | 49 |
| F11 | 24,634 | 24,654 | GCT GCT GAA ACG TTG CGG TTG | 26 |

TABLE 29-continued

| Primer name | Start Position | End Position | Primer sequence 5'==>3' | SEQ ID NO |
| --- | --- | --- | --- | --- |
| F14 | 26,894 | 26,914 | CCA TCT GCT CGT AGG AAT GCC | 50 |
| F16 | 40,460 | 40,479 | GCT ACC AGG GAA GAA CGG GA | 51 |
| F19 | 42,532 | 42,553 | CCA AGA TAG CAC TCG AAC GAC G | 52 |
| F23 | 17,973 | 17,994 | CGA ATC CCA TCT CGG CAA GGA G | 53 |
| F25 | 19,001 | 19,022 | GCA CTT GCG GTG ACA GTC ACT C | 54 |
| R04 | 27,492 | 27,472 | CCA GTG CAA AGC TTT GTG TGC | 55 |
| R11 | 24,654 | 24,634 | CAA CCG CAA CGT TTC AGC AGC | 56 |
| R15 | 25,696 | 25,677 | CCC AGT AGT ACT GCA AGA GG | 57 |
| R17 | 41,485 | 41,467 | CGT GGT GTA ATT CCC TCG C | 58 |
| R21 | 43,613 | 43,590 | GCT CAC CAG TTC GAT GAT TAA CGG | 59 |
| R25 | 19,022 | 19,001 | GAG TGA CTG TCA CCG CAA GTG C | 60 |
| R27 | 20,050 | 20,029 | GCA TCG CCG GCT GAT TTC TTC G | 61 |

5.1.3: Composition of PCR Reaction Solution

As the PCR reaction solution, the PCR reaction solution having the ordinary composition was used (Table 30). When Pyrobest was used as the PCR enzyme, 10x Pyrobest buffer II (unpublished composition) which was the attached buffer was used. When TaKaRa Taq was used, 10x PCR Buffer (100 mM Tris.Cl (pH 8.3), 500 mM KCl, 15 mM $MgCl_2$) which was the attached buffer was used. Pfu-PCNA13 was added at a final concentration of 0.6 ng/μg (0.3 μL), and when not added, the same volume (0.3 μL) of sterile water was added.

TABLE 30

| Composition | Amount to be added | Final concentration |
| --- | --- | --- |
| Lambda DNA (20 ng/μL) | 1.25 μL | 0.5 ng/μL |
| Forward Primer (20 pmol/μL) | 0.5 μL | 0.2 μM |
| Reverse Primer (20 pmol/μL) | 0.5 μL | 0.2 μM |
| 10x buffer[1] | 5 μL | 1x |
| dNTP Mix (2.5 mM each) | 4 μL | 0.2 mM |
| Enzyme (5 U/μL) | 0.25 μL | 0.025 U/μL |
| PCNA13 solution or sterile water[2] | 0.3 μL | 0 or 0.6 ng/μL |
| Sterile water | 38.2 μL | |
| Total | 50 μL | |

[1] 10x Buffer; 10x Pyrobest buffer II (upon using Pyrobest DNA polymearase), or 10x PCR Buffer (upon using TaKaRa Taq)
[2] Neat concentration of PCNA13; 100 ng/μL 5.1.4: PCR Program In the case of Pyrobest alone (98° C. for 10 seconds-->68° C. for 2.5 minutes) 30 cycles-->being kept at 4° C.

In the case of Pyrobest+Pfu-PCNA13

(98° C. for 10 seconds-->68° C. for 1.5 minutes) 30 cycles-->being kept at 4° C.

In the case of Taq alone (94° C. for 30 seconds-->55° C. for 30 seconds-->72° C. for 1.5 minutes) 30 cycles-->being kept at 4° C.

5.2: End Blunting and Purification of PCR Product

Each PCR product obtained in the aforementioned PCR reaction was subjected to 1% agarose gel electrophoresis and the gel was stained with ethidium bromide. Subsequently, a gel containing a DNA fragment having the objective size was cut out, and the DNA fragment in the gel was purified using GFX PCR DNA and Gel Band Purification Kit (Amersham Bioscience) according to its manipulation manual. The end of the purified DNA fragment was blunted and phosphorylated using TaKaRa BKL Kit (Blunting Kination Ligation Kit) (supplied from TAKARA BIO INC.) according to its kit manual.

5.3: Insertion of PCR Product into Cloning Vector

The DNA fragment (50 ng) whose ends had been blunted and phosphorylated was ligated to the DNA cleaved with the restriction enzyme HincII and treated with BAP (pUC118 HincII/BAP supplied from TAKARA BIO INC.) as follows.

DNA fragment whose ends was blunted and phosphorylated: 50 ng pUC118 HincII/BAP: 50 ng DNA ligation kit V2 enzyme solution: 5 μL Sterile water was added to the aforementioned mixture up to the total volume of 10 μL, which was then reacted at 16° C. for 60 minutes.

5.4: Isolation of *Escherichia coli* Colony and Extraction of Plasmid 5 100 μL of *Escherichia coli* JM109 (TAKARA BIO INC.) was transformed with this ligation product (3 μL), which was then seeded on the LB agar plate (containing 100 μg/mL of ampicillin, 40 μg/mL of IPTG, and 40 μg/mL of X-GAL), and cultured by leaving stand at 37° C. overnight. An *Escherichia coli* colony exhibiting the white color on the agar plate was cultured in 1.5 mL of the TB liquid medium (containing 100 μg/mL of ampicillin) at 37° C. overnight with shaking, and then a plasmid DNA was prepared according to the standard.

5.5: Sequencing of Inserted Sequence

The DNA sequence of the extracted plasmid as a template was analyzed using the DNA sequencer.

In the inserted DNA fragment (fragment amplified by PCR), the sequence of 500 bp was subjected to the analysis.

5.6: Comparison with the Original Sequence

The results were shown in Table 31. Terms used in the Table denote as follows.

"Fragment ID": Identification number of the target region in the PCR reaction.

"Enzyme AP": Combination of the enzyme with Pfu-PCNA 13 in the PCR reaction.

"Lambda DNA position": Position of the base sequence subjected to the analysis in seven PCR amplified fragments.

"Sample": Number of the plasmids subjected to the sequence analysis (i.e., number of the fragments amplified by PCR).

"Base": Number of the bases subjected to the sequence analysis.

"ND": Number of the bases indecipherable due to noise of sequencing data.

"ALL": Total number of the decipherable bases other than "ND".

"Error": Number of the bases identified as the replication error in the total number of the bases.

"Error rates": Rate of the number of the bases identified as the replication error "Error" relative to the number of the all deciphered bases "All".

TABLE 31

| Fragment ID | Enzyme, AP Lambda DNA Position | Pyrobest DNA Polymerase | | | | Pyrobest DNA Polymerase + Pfu-PCNA13 | | | | TaKaRa Taq | | | |
|---|---|---|---|---|---|---|---|---|---|---|---|---|---|
| | | Sample | ND | Base Error | All | Sample | ND | Base Error | All | Sample | ND | Base Error | All |
| 1 | 18,503-19,002 | 93 | 23 | 1 | 46,477 | 89 | 15 | 1 | 44,485 | 92 | 7 | 32 | 45,993 |
| 2 | 19,531-20,030 | 63 | 11 | 0 | 31,489 | 70 | 36 | 0 | 34,964 | 83 | 21 | 22 | 41,479 |
| 3 | 24,135-24,634 | 58 | 17 | 0 | 28,983 | 57 | 9 | 0 | 28,491 | 58 | 14 | 8 | 28,986 |
| 4 | 24,654-25,153 | 80 | 10 | 3 | 39,990 | 85 | 19 | 3 | 42,481 | 77 | 17 | 16 | 38,483 |
| 5 | 26,914-27,413 | 100 | 13 | 0 | 49,987 | 58 | 40 | 0 | 28,960 | 60 | 35 | 10 | 29,965 |
| 6 | 40,966-41,465 | 73 | 8 | 0 | 36,492 | 80 | 28 | 1 | 39,972 | 82 | 41 | 12 | 40,959 |
| 7 | 430,94-43,593 | 125 | 17 | 0 | 62,483 | 50 | 2 | 0 | 24,998 | 86 | 9 | 20 | 42,991 |
| | total | 592 | 99 | 4 | 295,901 | 489 | 149 | 5 | 244,351 | 538 | 144 | 120 | 268,856 |
| | Error rates (1/base) | | | | 1/73,975 | | | | 1/48,870 | | | | 1/2,240 |

In the case of Pyrobest alone, when 592 samples were analyzed, the replication errors were 4 bases in total 295,901 bases (the error rate is one base per 74 kb). In the case of Pyrobest in combination with Pfu-PCNA13, when 489 samples were analyzed, the replication errors were 5 bases in total 244,351 bases (the error rate is one base per 49 kb). In the case of Taq alone, when 538 samples were analyzed, the replication errors were 120 bases in total 268,856 bases (the error rate is one base per 2.2 kb).

Comparing among the aforementioned three test groups, in the case of Pyrobest alone and the case of Pyrobest in combination with Pfu-PCNA13, the error rate was one order lower than in the case of Taq alone. Thus, it was observed that the replication fidelity was obviously different between two groups.

Meanwhile, comparing the former two reactions (Pyrobest alone and Pyrobest in combination with Pfu-PCNA13), the replication errors were 4 (Pyrobest alone) and 5 (Pyrobest in combination with Pfu-PCNA13), and no significant difference was detected. It is unknown whether the obvious difference occurs or not in the fidelity by adding Pfu-PCNA, but the difference is small, and it is conceivable that at least the fidelity is not extremely worsened by adding Pfu-PCNA. As shown in Examples in FIGS. 14 to 16, it is obvious that PCNA keeps the fidelity at much higher level than Taq which is the PolI type PCR enzyme while it remarkably enhances the extendibility of Pyrobest which is the PCR enzyme with high fidelity. Thus, superiority of the PCNA of the present invention was proved.

INDUSTRIAL APPLICABILITY

The present invention is useful in biotechnology related industries, particularly useful in related technology involved in DNA synthesis.
Sequence Listing Free Text
SEQ ID NO:1: Pfu-PCNA
SEQ ID NO:2: Pfu-PCNA
SEQ ID NO:3: primer Pfu-PCNA-F
SEQ ID NO:4: primer Pfu-PCNA-R
SEQ ID NO:5: primer Pfu_M73L-F
SEQ ID NO:6: primer Pfu_M73L-R
SEQ ID NO:7: primer Pfu_D143A-F
SEQ ID NO:8: primer Pfu_D143A-R
SEQ ID NO:9: primer Pfu_R82C-F
SEQ ID NO:10: primer Pfu_R82C-R
SEQ ID NO:11: primer Pfu_D143R-F
SEQ ID NO:12: primer Pfu_D143R-R
SEQ ID NO:13: Pfu-RFCL
SEQ ID NO:14: Pfu-RFCL
SEQ ID NO:15: primer RFCL-F primer
SEQ ID NO:16: primer RFCL-R primer
SEQ ID NO:17: Pfu-RFCS
SEQ ID NO:18: Pfu-RFCS
SEQ ID NO:19: primer RFCS-F primer
SEQ ID NO:20: primer RFCS-R primer
SEQ ID NO:21: primer RFCSF1 primer
SEQ ID NO:22: primer RFCSF2 primer
SEQ ID NO:23: primer RFCSR2 primer
SEQ ID NO:24: primer RFCSR1 primer
SEQ ID NO:25: primer F02
SEQ ID NO:26: primer F11
SEQ ID NO:27: primer F24
SEQ ID NO:28: primer R03
SEQ ID NO:29: primer R14
SEQ ID NO:30: primer R16
SEQ ID NO:31: KOD-PCNA
SEQ ID NO:32: KOD-PCNA
SEQ ID NO:33: primer KOD-PCNA-F
SEQ ID NO:34: primer KOD-PCNA-R
SEQ ID NO:35: primer KOD-_M73L-F
SEQ ID NO:36: primer KOD-_M73L-R
SEQ ID NO:37: primer KOD-_E143R-F
SEQ ID NO:38: primer KOD-_E143R-R
SEQ ID NO:39: KOD-RFCL
SEQ ID NO:40: primer KOD-RFCL-F
SEQ ID NO:41: primer KOD-RFCL-R
SEQ ID NO:42: KOD-RFCS
SEQ ID NO:43: primer KOD-RFCS-F
SEQ ID NO:44: primer KOD-RFCS-R
SEQ ID NO:45: primer RFCS-Nde-F
SEQ ID NO:46: primer RFCS-Sal-R
SEQ ID NO:47: primer RFCS-Ex2-F
SEQ ID NO:48: primer RFCS-Ex1-R
SEQ ID NO:49: primer F09
SEQ ID NO:50: primer F14
SEQ ID NO:51: primer F16
SEQ ID NO:52: primer F19
SEQ ID NO:53: primer F23
SEQ ID NO:54: primer F25
SEQ ID NO:55: primer R04
SEQ ID NO:56: primer R11
SEQ ID NO:57: primer R15
SEQ ID NO:58: primer R17
SEQ ID NO:59: primer R21
SEQ ID NO:60: primer R25
SEQ ID NO:61: primer R27
SEQ ID NO:62: primer Pfu_D143K-F
SEQ ID NO:63: primer Pfu_D143K-R
SEQ ID NO:64: primer Pfu_D143H-F
SEQ ID NO:65: primer Pfu_D143H-R
SEQ ID NO:66: primer Pfu_R109E-F
SEQ ID NO:67: primer Pfu_R109E-R
SEQ ID NO:68: primer Pfu_D147R-F
SEQ ID NO:69: primer Pfu_D147R-R
SEQ ID NO:70: primer Pfu_E139A-F
SEQ ID NO:71: primer Pfu_E139A-R
SEQ ID NO:72: primer Pfu_E139R-F
SEQ ID NO:73: primer Pfu_E139R-R

The invention claimed is:

1. A mutant proliferating cell nuclear antigen (PCNA) monomer comprising an amino acid sequence obtained by substituting at least: (A) a first amino acid residue at a position selected from positions 82, 84, and 109 in SEQ ID NO:2 or SEQ ID NO: 32 and (B) a second amino acid residue at a position selected from positions 139, 143, and 147 of SEQ ID NO: 2 or SEQ ID NO: 32, such that mutual charge repulsion occurs between said monomer and another monomer when said monomer forms a multimeric complex with the other monomer, and (C) leucine at position 73 of SEQ ID NO:2 or 32, wherein
said monomer itself or the multimeric complex thereof having an activity to promote DNA replication.

2. The mutant PCNA monomer according to claim 1 wherein one or more amino acids selected from said group (i) and one or more amino acids selected from said group (ii) are both acidic amino acids or both basic amino acids.

3. The mutant PCNA monomer according to claim 1 having the sequence obtained by substituting the amino acid residue at position 143 with arginine in the amino acid sequence of SEQ ID NO:2 or 32.

4. A polynucleotide encoding an amino acid sequence of the PCNA monomer according to claim 1.

5. A transformant in which the polynucleotide according to claim 4 has been introduced.

6. A method for producing a mutant PCNA wherein the transformant according to claim 5 is cultured in a medium and a PCNA monomer and/or a multimeric complex composed of said monomer is accumulated in said transformant and/or the medium.

7. A reagent for DNA replication comprising the PCNA monomer according to claim 1 and/or a multimeric complex composed of said monomer.

8. A kit for DNA replication comprising the reagent according to claim 7.

9. The kit for DNA replication according to claim 8 further comprising a reagent for PCR.

10. A method for replicating DNA wherein DNA synthesis is performed in the presence of the PCNA monomer according to claim 1 and/or a multimeric complex composed of said monomer, and DNA polymerase.

11. The method for replicating the DNA according to claim 10 wherein said DNA synthesis is PCR.

* * * * *

```
                        SEQUENCE LISTING

<160> NUMBER OF SEQ ID NOS: 73

<210> SEQ ID NO 1
<211> LENGTH: 750
<212> TYPE: DNA
<213> ORGANISM: Pyrococcus furiosus
<220> FEATURE:
<221> NAME/KEY: CDS
<222> LOCATION: (1)..(750)
<223> OTHER INFORMATION: Pfu-PCNA

<400> SEQUENCE: 1 atg cca ttt gaa atc gta ttt gaa ggt gca aaa gag ttt gcc caa ctt       48
Met Pro Phe Glu Ile Val Phe Glu Gly Ala Lys Glu Phe Ala Gln Leu
1               5                   10                  15 ata gac acc gca agt aag tta ata gat gag gcc gcg ttt aaa gtt aca       96
Ile Asp Thr Ala Ser Lys Leu Ile Asp Glu Ala Ala Phe Lys Val Thr
            20                  25                  30
```

-continued

| | |
|---|---|
| gaa gat ggg ata agc atg agg gcc atg gat cca agt aga gtt gtc ctg<br>Glu Asp Gly Ile Ser Met Arg Ala Met Asp Pro Ser Arg Val Val Leu<br>35                        40                       45 | 144 |
| att gac cta aat ctc ccg tca agc ata ttt agc aaa tat gaa gtt gtt<br>Ile Asp Leu Asn Leu Pro Ser Ser Ile Phe Ser Lys Tyr Glu Val Val<br>50                        55                       60 | 192 |
| gaa cca gaa aca att gga gtt aac atg gac cac cta aag aag atc cta<br>Glu Pro Glu Thr Ile Gly Val Asn Met Asp His Leu Lys Lys Ile Leu<br>65                        70                       75                       80 | 240 |
| aag aga ggt aaa gca aag gac acc tta ata ctc aag aaa gga gag gaa<br>Lys Arg Gly Lys Ala Lys Asp Thr Leu Ile Leu Lys Lys Gly Glu Glu<br>                       85                       90                       95 | 288 |
| aac ttc tta gag ata aca att caa gga act gca aca aga aca ttt aga<br>Asn Phe Leu Glu Ile Thr Ile Gln Gly Thr Ala Thr Arg Thr Phe Arg<br>                100                     105                     110 | 336 |
| gtt ccc cta ata gat gta gaa gag atg gaa gtt gac ctc cca gaa ctt<br>Val Pro Leu Ile Asp Val Glu Glu Met Glu Val Asp Leu Pro Glu Leu<br>               115                    120                     125 | 384 |
| cca ttc act gca aag gtt gta gtt ctt gga gaa gtc cta aaa gat gct<br>Pro Phe Thr Ala Lys Val Val Val Leu Gly Glu Val Leu Lys Asp Ala<br>130                       135                    140 | 432 |
| gtt aaa gat gcc tct cta gtg agt gac agc ata aaa ttt att gcc agg<br>Val Lys Asp Ala Ser Leu Val Ser Asp Ser Ile Lys Phe Ile Ala Arg<br>145                       150                    155                    160 | 480 |
| gaa aat gaa ttt ata atg aag gca gag gga gaa acc cag gaa gtt gag<br>Glu Asn Glu Phe Ile Met Lys Ala Glu Gly Glu Thr Gln Glu Val Glu<br>               165                    170                     175 | 528 |
| ata aag cta act ctt gaa gat gag gga tta ttg gac atc gag gtt caa<br>Ile Lys Leu Thr Leu Glu Asp Glu Gly Leu Leu Asp Ile Glu Val Gln<br>                180                     185                    190 | 576 |
| gag gag aca aag agc gca tat gga gtc agc tat ctc tcc gac atg gtt<br>Glu Glu Thr Lys Ser Ala Tyr Gly Val Ser Tyr Leu Ser Asp Met Val<br>                   195                    200                    205 | 624 |
| aaa gga ctt gga aag gcc gat gaa gtt aca ata aag ttt gga aat gaa<br>Lys Gly Leu Gly Lys Ala Asp Glu Val Thr Ile Lys Phe Gly Asn Glu<br>210                       215                    220 | 672 |
| atg ccc atg caa atg gag tat tac att aga gat gaa gga aga ctt aca<br>Met Pro Met Gln Met Glu Tyr Tyr Ile Arg Asp Glu Gly Arg Leu Thr<br>225                       230                    235                    240 | 720 |
| ttc ctg ctg gct cca aga gtt gaa gag tga<br>Phe Leu Leu Ala Pro Arg Val Glu Glu<br>               245 | 750 |

<210> SEQ ID NO 2
<211> LENGTH: 249
<212> TYPE: PRT
<213> ORGANISM: Pyrococcus furiosus

<400> SEQUENCE: 2

Met Pro Phe Glu Ile Val Phe Glu Gly Ala Lys Glu Phe Ala Gln Leu
1               5                   10                   15

Ile Asp Thr Ala Ser Lys Leu Ile Asp Glu Ala Ala Phe Lys Val Thr
              20                   25                   30

Glu Asp Gly Ile Ser Met Arg Ala Met Asp Pro Ser Arg Val Val Leu
                 35                   40                   45

Ile Asp Leu Asn Leu Pro Ser Ser Ile Phe Ser Lys Tyr Glu Val Val
     50                   55                   60

Glu Pro Glu Thr Ile Gly Val Asn Met Asp His Leu Lys Lys Ile Leu
65               70                   75                   80

```
Lys Arg Gly Lys Ala Lys Asp Thr Leu Ile Leu Lys Lys Gly Glu Glu
                85                  90                  95
Asn Phe Leu Glu Ile Thr Ile Gln Gly Thr Ala Thr Arg Thr Phe Arg
            100                 105                 110
Val Pro Leu Ile Asp Val Glu Glu Met Glu Val Asp Leu Pro Glu Leu
        115                 120                 125
Pro Phe Thr Ala Lys Val Val Val Leu Gly Glu Val Leu Lys Asp Ala
    130                 135                 140
Val Lys Asp Ala Ser Leu Val Ser Asp Ser Ile Lys Phe Ile Ala Arg
145                 150                 155                 160
Glu Asn Glu Phe Ile Met Lys Ala Glu Gly Thr Gln Glu Val
                165                 170                 175
Ile Lys Leu Thr Leu Glu Asp Glu Gly Leu Leu Asp Ile Glu Val Gln
            180                 185                 190
Glu Glu Thr Lys Ser Ala Tyr Gly Val Ser Tyr Leu Ser Asp Met Val
        195                 200                 205
Lys Gly Leu Gly Lys Ala Asp Glu Val Thr Ile Lys Phe Gly Asn Glu
    210                 215                 220
Met Pro Met Gln Met Glu Tyr Tyr Ile Arg Asp Glu Gly Arg Leu Thr
225                 230                 235                 240
Phe Leu Leu Ala Pro Arg Val Glu Glu
                245

<210> SEQ ID NO 3
<211> LENGTH: 23
<212> TYPE: DNA
<213> ORGANISM: Artificial
<220> FEATURE:
<223> OTHER INFORMATION: primer: Pfu_PCNA-F

<400> SEQUENCE: 3
catatgccat tgaaatcgt att                                         23

<210> SEQ ID NO 4
<211> LENGTH: 21
<212> TYPE: DNA
<213> ORGANISM: Artificial
<220> FEATURE:
<223> OTHER INFORMATION: Primer: Pfu_PCNA-R

<400> SEQUENCE: 4
ctcgagtcac tcttcaactc t                                          21

<210> SEQ ID NO 5
<211> LENGTH: 29
<212> TYPE: DNA
<213> ORGANISM: Artificial
<220> FEATURE:
<223> OTHER INFORMATION: primer: Pfu_M73L-F

<400> SEQUENCE: 5
caattggagt taacctggac cacctaaag                                  29

<210> SEQ ID NO 6
<211> LENGTH: 29
<212> TYPE: DNA
<213> ORGANISM: Artificial
<220> FEATURE:
<223> OTHER INFORMATION: Pfu_M73L-R

<400> SEQUENCE: 6
ctttaggtgg tccaggttaa ctccaattg                                  29
```

<210> SEQ ID NO 7
<211> LENGTH: 55
<212> TYPE: DNA
<213> ORGANISM: Artificial
<220> FEATURE:
<223> OTHER INFORMATION: Pfu_D143A-F

<400> SEQUENCE: 7
ttcttggaga agtcctaaaa gctgctgtta aagatgcctc tctagtgagt gacag        55

<210> SEQ ID NO 8
<211> LENGTH: 55
<212> TYPE: DNA
<213> ORGANISM: Artificial
<220> FEATURE:
<223> OTHER INFORMATION: primer: Pfu_D143A-R

<400> SEQUENCE: 8
ctgtcactca ctagagaggc atctttaaca gcagctttta ggacttctcc aagaa        55

<210> SEQ ID NO 9
<211> LENGTH: 35
<212> TYPE: DNA
<213> ORGANISM: Artificial
<220> FEATURE:
<223> OTHER INFORMATION: primer: Pfu_R82C-F

<400> SEQUENCE: 9
cctaaagaag atcctaaagt gcggtaaagc aaagg        35

<210> SEQ ID NO 10
<211> LENGTH: 35
<212> TYPE: DNA
<213> ORGANISM: Artificial
<220> FEATURE:
<223> OTHER INFORMATION: primer: Pfu_R82C-R

<400> SEQUENCE: 10
cctttgcttt accgcacttt aggatcttct ttagg        35

<210> SEQ ID NO 11
<211> LENGTH: 33
<212> TYPE: DNA
<213> ORGANISM: Artificial
<220> FEATURE:
<223> OTHER INFORMATION: primer: Pfu_D143R-F

<400> SEQUENCE: 11
ggagaagtcc taaaacgtgc tgttaaagat gcc        33

<210> SEQ ID NO 12
<211> LENGTH: 33
<212> TYPE: DNA
<213> ORGANISM: Artificial
<220> FEATURE:
<223> OTHER INFORMATION: primer: Pfu_D143R-R

<400> SEQUENCE: 12
ggcatcttta acagcacgtt ttaggacttc tcc        33

<210> SEQ ID NO 13
<211> LENGTH: 1440
<212> TYPE: DNA
<213> ORGANISM: Pyrococcus furiosus
<220> FEATURE:
<221> NAME/KEY: CDS
<222> LOCATION: (1)..(1440)
<223> OTHER INFORMATION: Pfu-RFCL

<400> SEQUENCE: 13

| | | | | | | | | | | | | | | | | |
|---|---|---|---|---|---|---|---|---|---|---|---|---|---|---|---|---|
| atg | cca | gag | ctt | ccc | tgg | gta | gaa | aaa | tac | agg | cca | aaa | aag | tta | agt | 48 |
| Met | Pro | Glu | Leu | Pro | Trp | Val | Glu | Lys | Tyr | Arg | Pro | Lys | Lys | Leu | Ser | |
| 1 | | | | 5 | | | | | 10 | | | | | 15 | | |
| gaa | att | gta | aac | caa | gag | gct | ata | gag | aaa | gtt | aga | gcg | tgg | ata | | 96 |
| Glu | Ile | Val | Asn | Gln | Glu | Ala | Ile | Glu | Lys | Val | Arg | Ala | Trp | Ile | | |
| | | | 20 | | | | | 25 | | | | | 30 | | | |
| gag | agc | tgg | ttg | cat | ggc | cac | ccc | cct | aag | aaa | aaa | gcc | cta | tta | tta | 144 |
| Glu | Ser | Trp | Leu | His | Gly | His | Pro | Pro | Lys | Lys | Lys | Ala | Leu | Leu | Leu | |
| | | 35 | | | | | 40 | | | | | 45 | | | | |
| gca | ggg | ccc | cca | ggg | agc | gga | aag | aca | acc | aca | gtc | tac | gct | cta | gca | 192 |
| Ala | Gly | Pro | Pro | Gly | Ser | Gly | Lys | Thr | Thr | Thr | Val | Tyr | Ala | Leu | Ala | |
| 50 | | | | | 55 | | | | | 60 | | | | | | |
| aat | gag | tac | aac | ttt | gaa | gtc | att | gag | ctc | aac | gcg | agt | gat | gag | aga | 240 |
| Asn | Glu | Tyr | Asn | Phe | Glu | Val | Ile | Glu | Leu | Asn | Ala | Ser | Asp | Glu | Arg | |
| 65 | | | | | 70 | | | | | 75 | | | | | 80 | |
| act | tat | gaa | aaa | atc | tcc | agg | tat | gtt | caa | gca | gca | tac | act | atg | gat | 288 |
| Thr | Tyr | Glu | Lys | Ile | Ser | Arg | Tyr | Val | Gln | Ala | Ala | Tyr | Thr | Met | Asp | |
| | | | | 85 | | | | | 90 | | | | | 95 | | |
| atc | ctc | gga | aag | agg | agg | aag | ata | atc | ttc | ctc | gat | gaa | gca | gat | aat | 336 |
| Ile | Leu | Gly | Lys | Arg | Arg | Lys | Ile | Ile | Phe | Leu | Asp | Glu | Ala | Asp | Asn | |
| | | | 100 | | | | | 105 | | | | | 110 | | | |
| ata | gag | ccc | agc | gga | gct | aag | gaa | atc | gca | aaa | cta | att | gat | aag | gcc | 384 |
| Ile | Glu | Pro | Ser | Gly | Ala | Lys | Glu | Ile | Ala | Lys | Leu | Ile | Asp | Lys | Ala | |
| | | 115 | | | | | 120 | | | | | 125 | | | | |
| aaa | aat | cca | ata | ata | atg | gct | gca | aat | aag | tac | tgg | gaa | gtt | cca | aaa | 432 |
| Lys | Asn | Pro | Ile | Ile | Met | Ala | Ala | Asn | Lys | Tyr | Trp | Glu | Val | Pro | Lys | |
| 130 | | | | | 135 | | | | | 140 | | | | | | |
| gag | atc | cga | gaa | aaa | gct | gag | cta | gta | gag | tac | aag | agg | tta | acc | cag | 480 |
| Glu | Ile | Arg | Glu | Lys | Ala | Glu | Leu | Val | Glu | Tyr | Lys | Arg | Leu | Thr | Gln | |
| 145 | | | | | 150 | | | | | 155 | | | | | 160 | |
| aga | gat | gta | atg | aat | gcc | tta | ata | agg | atc | cta | aag | agg | gaa | ggt | ata | 528 |
| Arg | Asp | Val | Met | Asn | Ala | Leu | Ile | Arg | Ile | Leu | Lys | Arg | Glu | Gly | Ile | |
| | | | | 165 | | | | | 170 | | | | | 175 | | |
| aca | gtt | cca | aaa | gaa | atc | ctc | cta | gaa | ata | gca | aaa | aga | tct | agt | gga | 576 |
| Thr | Val | Pro | Lys | Glu | Ile | Leu | Leu | Glu | Ile | Ala | Lys | Arg | Ser | Ser | Gly | |
| | | | 180 | | | | | 185 | | | | | 190 | | | |
| gat | cta | aga | gca | gct | ata | aat | gat | cta | cag | acc | gtt | gta | gtg | ggt | ggt | 624 |
| Asp | Leu | Arg | Ala | Ala | Ile | Asn | Asp | Leu | Gln | Thr | Val | Val | Val | Gly | Gly | |
| | | 195 | | | | | 200 | | | | | 205 | | | | |
| tac | gaa | gat | gct | acg | caa | gtt | ttg | gca | tat | aga | gat | gta | gaa | aag | aca | 672 |
| Tyr | Glu | Asp | Ala | Thr | Gln | Val | Leu | Ala | Tyr | Arg | Asp | Val | Glu | Lys | Thr | |
| | | 210 | | | | | 215 | | | | | 220 | | | | |
| gtc | ttt | caa | gcc | cta | gga | ctc | gtc | ttt | gga | agt | gac | aac | gcc | aag | agg | 720 |
| Val | Phe | Gln | Ala | Leu | Gly | Leu | Val | Phe | Gly | Ser | Asp | Asn | Ala | Lys | Arg | |
| 225 | | | | | 230 | | | | | 235 | | | | | 240 | |
| gca | aag | atg | gca | atg | tgg | aac | ttg | gac | atg | tcc | cct | gat | gaa | ttc | ctg | 768 |
| Ala | Lys | Met | Ala | Met | Trp | Asn | Leu | Asp | Met | Ser | Pro | Asp | Glu | Phe | Leu | |
| | | | | 245 | | | | | 250 | | | | | 255 | | |
| cta | tgg | gta | gat | gag | aac | att | cct | cac | ctc | tac | cta | aat | cca | gag | gag | 816 |
| Leu | Trp | Val | Asp | Glu | Asn | Ile | Pro | His | Leu | Tyr | Leu | Asn | Pro | Glu | Glu | |
| | | | 260 | | | | | 265 | | | | | 270 | | | |
| att | gcc | cag | gcg | tat | gat | gca | att | agt | aga | gcc | gac | ata | tac | ctc | gga | 864 |
| Ile | Ala | Gln | Ala | Tyr | Asp | Ala | Ile | Ser | Arg | Ala | Asp | Ile | Tyr | Leu | Gly | |
| | | 275 | | | | | 280 | | | | | 285 | | | | |
| agg | gcc | gcc | aga | act | gga | aac | tat | tca | ctc | tgg | aag | tac | gca | ata | gat | 912 |
| Arg | Ala | Ala | Arg | Thr | Gly | Asn | Tyr | Ser | Leu | Trp | Lys | Tyr | Ala | Ile | Asp | |
| | | 290 | | | | | 295 | | | | | 300 | | | | |

| | | | | | | | | | | | | | | | | |
|---|---|---|---|---|---|---|---|---|---|---|---|---|---|---|---|---|
| atg | atg | act | gca | gga | gtt | gcc | gtg | gca | ggg | aga | aag | aga | agg | gga | ttt | 960 |
| Met | Met | Thr | Ala | Gly | Val | Ala | Val | Ala | Gly | Arg | Lys | Arg | Arg | Gly | Phe | |
| 305 | | | | 310 | | | | | 315 | | | | | 320 | | |
| gtc | aag | ttt | tat | cct | ccc | aac | acc | cta | aag | att | tta | gcg | gaa | agc | aaa | 1008 |
| Val | Lys | Phe | Tyr | Pro | Pro | Asn | Thr | Leu | Lys | Ile | Leu | Ala | Glu | Ser | Lys | |
| | | | | 325 | | | | | 330 | | | | | 335 | | |
| gaa | gaa | aga | gag | atc | aga | gag | tca | ata | att | aaa | aag | ata | ata | cga | gag | 1056 |
| Glu | Glu | Arg | Glu | Ile | Arg | Glu | Ser | Ile | Ile | Lys | Lys | Ile | Ile | Arg | Glu | |
| | | | 340 | | | | | 345 | | | | | 350 | | | |
| atg | cac | atg | agt | agg | cta | cag | gca | ata | gaa | acg | atg | aaa | ata | att | aga | 1104 |
| Met | His | Met | Ser | Arg | Leu | Gln | Ala | Ile | Glu | Thr | Met | Lys | Ile | Ile | Arg | |
| | | 355 | | | | | 360 | | | | | 365 | | | | |
| gag | att | ttc | gag | aac | aat | cta | gac | ctt | gct | gcg | cac | ttt | aca | gtg | ttc | 1152 |
| Glu | Ile | Phe | Glu | Asn | Asn | Leu | Asp | Leu | Ala | Ala | His | Phe | Thr | Val | Phe | |
| 370 | | | | | 375 | | | | | 380 | | | | | | |
| ctt | ggt | ctg | tct | gaa | aaa | gaa | gtt | gag | ttt | cta | gct | gga | aag | gaa | aaa | 1200 |
| Leu | Gly | Leu | Ser | Glu | Lys | Glu | Val | Glu | Phe | Leu | Ala | Gly | Lys | Glu | Lys | |
| 385 | | | | | 390 | | | | | 395 | | | | | 400 | |
| gct | ggt | acc | att | tgg | ggc | aaa | gcc | tta | gca | tta | aga | agg | aaa | ctt | aag | 1248 |
| Ala | Gly | Thr | Ile | Trp | Gly | Lys | Ala | Leu | Ala | Leu | Arg | Arg | Lys | Leu | Lys | |
| | | | | 405 | | | | | 410 | | | | | 415 | | |
| gag | ctt | gga | ata | aga | gag | gag | gag | aag | cct | aaa | gtt | gaa | att | gaa | gaa | 1296 |
| Glu | Leu | Gly | Ile | Arg | Glu | Glu | Glu | Lys | Pro | Lys | Val | Glu | Ile | Glu | Glu | |
| | | | 420 | | | | | 425 | | | | | 430 | | | |
| gag | gaa | gaa | gag | gaa | gaa | aag | acc | gaa | gaa | gaa | aaa | gag | gaa | ata | gaa | 1344 |
| Glu | Glu | Glu | Glu | Glu | Glu | Lys | Thr | Glu | Glu | Glu | Lys | Glu | Glu | Ile | Glu | |
| | | 435 | | | | | 440 | | | | | 445 | | | | |
| gaa | aaa | ccc | gaa | gaa | gag | aaa | gaa | gag | gag | aag | aaa | gaa | aag | gaa | aag | 1392 |
| Glu | Lys | Pro | Glu | Glu | Glu | Lys | Glu | Glu | Glu | Lys | Lys | Glu | Lys | Glu | Lys | |
| | 450 | | | | | 455 | | | | | 460 | | | | | |
| cca | aag | aaa | ggc | aaa | caa | gca | act | ctc | ttt | gac | ttt | ctt | aaa | aag | tga | 1440 |
| Pro | Lys | Lys | Gly | Lys | Gln | Ala | Thr | Leu | Phe | Asp | Phe | Leu | Lys | Lys | | |
| 465 | | | | 470 | | | | | 475 | | | | | | | |

<210> SEQ ID NO 14
<211> LENGTH: 479
<212> TYPE: PRT
<213> ORGANISM: Pyrococcus furiosus

<400> SEQUENCE: 14

Met Pro Glu Leu Pro Trp Val Glu Lys Tyr Arg Pro Lys Lys Leu Ser
1               5                   10                  15

Glu Ile Val Asn Gln Glu Glu Ala Ile Glu Lys Val Arg Ala Trp Ile
            20                  25                  30

Glu Ser Trp Leu His Gly His Pro Pro Lys Lys Ala Leu Leu Leu
        35                  40                  45

Ala Gly Pro Pro Gly Ser Gly Lys Thr Thr Thr Val Tyr Ala Leu Ala
    50                  55                  60

Asn Glu Tyr Asn Phe Glu Val Ile Glu Leu Asn Ala Ser Asp Glu Arg
65                  70                  75                  80

Thr Tyr Glu Lys Ile Ser Arg Tyr Val Gln Ala Ala Tyr Thr Met Asp
                85                  90                  95

Ile Leu Gly Lys Arg Arg Lys Ile Ile Phe Leu Asp Glu Ala Asp Asn
            100                 105                 110

Ile Glu Pro Ser Gly Ala Lys Glu Ile Ala Lys Leu Ile Asp Lys Ala
        115                 120                 125

Lys Asn Pro Ile Ile Met Ala Ala Asn Lys Tyr Trp Glu Val Pro Lys
    130                 135                 140

```
Glu Ile Arg Glu Lys Ala Glu Leu Val Glu Tyr Lys Arg Leu Thr Gln
145                 150                 155                 160

Arg Asp Val Met Asn Ala Leu Ile Arg Ile Leu Lys Arg Glu Gly Ile
                165                 170                 175

Thr Val Pro Lys Glu Ile Leu Leu Glu Ile Ala Lys Arg Ser Ser Gly
            180                 185                 190

Asp Leu Arg Ala Ala Ile Asn Asp Leu Gln Thr Val Val Gly Gly
        195                 200                 205

Tyr Glu Asp Ala Thr Gln Val Leu Ala Tyr Arg Asp Val Glu Lys Thr
    210                 215                 220

Val Phe Gln Ala Leu Gly Leu Val Phe Gly Ser Asp Asn Ala Lys Arg
225                 230                 235                 240

Ala Lys Met Ala Met Trp Asn Leu Asp Met Ser Pro Asp Glu Phe Leu
                245                 250                 255

Leu Trp Val Asp Glu Asn Ile Pro His Leu Tyr Leu Asn Pro Glu Glu
                260                 265                 270

Ile Ala Gln Ala Tyr Asp Ala Ile Ser Arg Ala Asp Ile Tyr Leu Gly
            275                 280                 285

Arg Ala Ala Arg Thr Gly Asn Tyr Ser Leu Trp Lys Tyr Ala Ile Asp
290                 295                 300

Met Met Thr Ala Gly Val Ala Val Ala Gly Arg Lys Arg Gly Phe
305                 310                 315                 320

Val Lys Phe Tyr Pro Pro Asn Thr Leu Lys Ile Leu Ala Glu Ser Lys
                325                 330                 335

Glu Glu Arg Glu Ile Arg Glu Ser Ile Ile Lys Lys Ile Ile Arg Glu
            340                 345                 350

Met His Met Ser Arg Leu Gln Ala Ile Glu Thr Met Lys Ile Ile Arg
        355                 360                 365

Glu Ile Phe Glu Asn Asn Leu Asp Leu Ala Ala His Phe Thr Val Phe
    370                 375                 380

Leu Gly Leu Ser Glu Lys Gly Val Glu Phe Leu Ala Gly Lys Glu Lys
385                 390                 395                 400

Ala Gly Thr Ile Trp Gly Lys Ala Leu Ala Leu Arg Arg Lys Leu Lys
                405                 410                 415

Glu Leu Gly Ile Arg Glu Glu Glu Lys Pro Lys Val Glu Ile Glu Glu
            420                 425                 430

Glu Glu Glu Glu Glu Glu Lys Thr Glu Glu Glu Lys Glu Glu Ile Glu
        435                 440                 445

Glu Lys Pro Glu Glu Glu Glu Glu Lys Glu Lys Glu Lys
450                 455                 460

Pro Lys Lys Gly Lys Gln Ala Thr Leu Phe Asp Phe Leu Lys Lys
465                 470                 475

<210> SEQ ID NO 15
<211> LENGTH: 30
<212> TYPE: DNA
<213> ORGANISM: Artificial
<220> FEATURE:
<223> OTHER INFORMATION: primer: RFCL-F primer

<400> SEQUENCE: 15
agccatatgc cagagcttcc ctgggtagaa                                      30

<210> SEQ ID NO 16
<211> LENGTH: 34
<212> TYPE: DNA
<213> ORGANISM: Artificial
```

```
<220> FEATURE:
<223> OTHER INFORMATION: primer: RFCL-R primer

<400> SEQUENCE: 16
agctcgagtc acttttttaag aaagtcaaag agag                              34

<210> SEQ ID NO 17
<211> LENGTH: 2559
<212> TYPE: DNA
<213> ORGANISM: Pyrococcus furiosus
<220> FEATURE:
<221> NAME/KEY: CDS
<222> LOCATION: (1)..(2559)
<223> OTHER INFORMATION: Pfu-RFCS

<400> SEQUENCE: 17
```

| | | | | | | | | | | | | | | | | |
|---|---|---|---|---|---|---|---|---|---|---|---|---|---|---|---|---|
| atg | agc | gaa | gag | att | aga | gaa | gtt | aag | gtt | cta | gaa | aaa | ccc | tgg | gtt | 48 |
| Met | Ser | Glu | Glu | Ile | Arg | Glu | Val | Lys | Val | Leu | Glu | Lys | Pro | Trp | Val | |
| 1 | | | | 5 | | | | | 10 | | | | | 15 | | |
| gag | aag | tat | aga | cct | caa | aga | ctt | gac | gac | att | gta | gga | caa | gag | cac | 96 |
| Glu | Lys | Tyr | Arg | Pro | Gln | Arg | Leu | Asp | Asp | Ile | Val | Gly | Gln | Glu | His | |
| | | | 20 | | | | | 25 | | | | | 30 | | | |
| ata | gtg | aaa | agg | ctc | aag | cac | tac | gtc | aaa | act | gga | tca | atg | ccc | cac | 144 |
| Ile | Val | Lys | Arg | Leu | Lys | His | Tyr | Val | Lys | Thr | Gly | Ser | Met | Pro | His | |
| | 35 | | | | | 40 | | | | | 45 | | | | | |
| cta | ctc | ttc | gca | ggc | cct | cct | ggt | gtc | gga | aag | tgt | ctt | act | gga | gat | 192 |
| Leu | Leu | Phe | Ala | Gly | Pro | Pro | Gly | Val | Gly | Lys | Cys | Leu | Thr | Gly | Asp | |
| 50 | | | | | 55 | | | | | 60 | | | | | | |
| acc | aaa | gtt | ata | gct | aat | ggc | caa | ctc | ttt | gaa | ctt | gga | gaa | ctt | gtt | 240 |
| Thr | Lys | Val | Ile | Ala | Asn | Gly | Gln | Leu | Phe | Glu | Leu | Gly | Glu | Leu | Val | |
| 65 | | | | | 70 | | | | | 75 | | | | | 80 | |
| gaa | aag | ctt | tct | ggg | ggg | aga | ttt | gga | cca | act | cca | gtt | aaa | ggg | ctc | 288 |
| Glu | Lys | Leu | Ser | Gly | Gly | Arg | Phe | Gly | Pro | Thr | Pro | Val | Lys | Gly | Leu | |
| | | | | 85 | | | | | 90 | | | | | 95 | | |
| aaa | gtt | ctt | gga | ata | gat | gag | gat | gga | aag | ctt | aga | gag | ttt | gaa | gtc | 336 |
| Lys | Val | Leu | Gly | Ile | Asp | Glu | Asp | Gly | Lys | Leu | Arg | Glu | Phe | Glu | Val | |
| | | | 100 | | | | | 105 | | | | | 110 | | | |
| caa | tac | gtc | tac | aaa | gat | aga | act | gat | agg | ttg | ata | aag | ata | aaa | act | 384 |
| Gln | Tyr | Val | Tyr | Lys | Asp | Arg | Thr | Asp | Arg | Leu | Ile | Lys | Ile | Lys | Thr | |
| | 115 | | | | | 120 | | | | | 125 | | | | | |
| cag | ctt | ggc | agg | gag | ctt | aaa | gta | act | ccg | tat | cac | cca | ctt | cta | gtg | 432 |
| Gln | Leu | Gly | Arg | Glu | Leu | Lys | Val | Thr | Pro | Tyr | His | Pro | Leu | Leu | Val | |
| 130 | | | | | 135 | | | | | 140 | | | | | | |
| aat | aga | gag | aat | ggc | gaa | ata | aag | tgg | att | aag | gct | gaa | gaa | ctc | aaa | 480 |
| Asn | Arg | Glu | Asn | Gly | Glu | Ile | Lys | Trp | Ile | Lys | Ala | Glu | Glu | Leu | Lys | |
| 145 | | | | | 150 | | | | | 155 | | | | | 160 | |
| cct | ggc | gac | aag | ctt | gca | ata | ccg | agc | ttt | ctc | cca | ctt | ata | act | gga | 528 |
| Pro | Gly | Asp | Lys | Leu | Ala | Ile | Pro | Ser | Phe | Leu | Pro | Leu | Ile | Thr | Gly | |
| | | | | 165 | | | | | 170 | | | | | 175 | | |
| gaa | aat | ccc | ctt | gca | gag | tgg | ctt | ggt | tac | ttt | atg | gga | agt | ggc | tat | 576 |
| Glu | Asn | Pro | Leu | Ala | Glu | Trp | Leu | Gly | Tyr | Phe | Met | Gly | Ser | Gly | Tyr | |
| | | | 180 | | | | | 185 | | | | | 190 | | | |
| gct | tat | cca | agt | aat | tct | gtc | atc | acg | ttc | act | aac | gaa | gat | cca | ctc | 624 |
| Ala | Tyr | Pro | Ser | Asn | Ser | Val | Ile | Thr | Phe | Thr | Asn | Glu | Asp | Pro | Leu | |
| | 195 | | | | | 200 | | | | | 205 | | | | | |
| ata | aga | caa | cgc | ttt | atg | gaa | cta | aca | gag | aaa | ctt | ttc | cct | gat | gca | 672 |
| Ile | Arg | Gln | Arg | Phe | Met | Glu | Leu | Thr | Glu | Lys | Leu | Phe | Pro | Asp | Ala | |
| 210 | | | | | 215 | | | | | 220 | | | | | | |
| aag | ata | agg | gaa | aga | att | cac | gct | gat | gga | act | cca | gaa | gtt | tat | gtg | 720 |
| Lys | Ile | Arg | Glu | Arg | Ile | His | Ala | Asp | Gly | Thr | Pro | Glu | Val | Tyr | Val | |
| 225 | | | | | 230 | | | | | 235 | | | | | 240 | |
| gta | tct | agg | aaa | gct | tgg | agc | ctt | gta | aac | tct | att | agc | tta | aca | tta | 768 |

-continued

| | | |
|---|---|---|
| Val Ser Arg Lys Ala Trp Ser Leu Val Asn Ser Ile Ser Leu Thr Leu<br>245 250 255 | | |
| ata ccc agg gag ggg tgg aaa gga att cgt tct ttc ctt agg gca tat<br>Ile Pro Arg Glu Gly Trp Lys Gly Ile Arg Ser Phe Leu Arg Ala Tyr<br>260 265 270 | | 816 |
| tcc gac tgc aat ggt cgg att gaa agt gat gca ata gtt tta tca acc<br>Ser Asp Cys Asn Gly Arg Ile Glu Ser Asp Ala Ile Val Leu Ser Thr<br>275 280 285 | | 864 |
| gat aac aat gat atg gcc cag cag ata gcc tat gct tta gcc agc ttt<br>Asp Asn Asn Asp Met Ala Gln Gln Ile Ala Tyr Ala Leu Ala Ser Phe<br>290 295 300 | | 912 |
| gga ata ata gct aaa atg gat gga gaa gat gtt att atc tca ggc tcg<br>Gly Ile Ile Ala Lys Met Asp Gly Glu Asp Val Ile Ile Ser Gly Ser<br>305 310 315 320 | | 960 |
| gac aac ata gag agg ttc cta aat gag att ggc ttt agc acc caa agc<br>Asp Asn Ile Glu Arg Phe Leu Asn Glu Ile Gly Phe Ser Thr Gln Ser<br>325 330 335 | | 1008 |
| aaa ctt aaa gaa gcc cag aag ctc att aga aaa acc aat gta aga tcc<br>Lys Leu Lys Glu Ala Gln Lys Leu Ile Arg Lys Thr Asn Val Arg Ser<br>340 345 350 | | 1056 |
| gat gga cta aag att aac tat gag cta atc tcc tat gta aaa gac agg<br>Asp Gly Leu Lys Ile Asn Tyr Glu Leu Ile Ser Tyr Val Lys Asp Arg<br>355 360 365 | | 1104 |
| ctt agg tta aat gtc aat gat aaa aga aat ttg agc tac aga aat gca<br>Leu Arg Leu Asn Val Asn Asp Lys Arg Asn Leu Ser Tyr Arg Asn Ala<br>370 375 380 | | 1152 |
| aag gag ctt tct tgg gaa ctc atg aaa gaa att tat tat cgc ctt gag<br>Lys Glu Leu Ser Trp Glu Leu Met Lys Glu Ile Tyr Tyr Arg Leu Glu<br>385 390 395 400 | | 1200 |
| gaa ctg gag aga cta aag aag gtc tta tca gaa ccc atc ttg atc gac<br>Glu Leu Glu Arg Leu Lys Lys Val Leu Ser Glu Pro Ile Leu Ile Asp<br>405 410 415 | | 1248 |
| tgg aat gaa gta gca aag aag agt gat gaa gta ata gaa aaa gct aaa<br>Trp Asn Glu Val Ala Lys Lys Ser Asp Glu Val Ile Glu Lys Ala Lys<br>420 425 430 | | 1296 |
| att aga gca gag aag ctc cta gaa tac ata aaa gga gag aga aag cca<br>Ile Arg Ala Glu Lys Leu Leu Glu Tyr Ile Lys Gly Glu Arg Lys Pro<br>435 440 445 | | 1344 |
| agt ttc aag gag tac att gag ata gca aaa gtc ctt gga att aac gtt<br>Ser Phe Lys Glu Tyr Ile Glu Ile Ala Lys Val Leu Gly Ile Asn Val<br>450 455 460 | | 1392 |
| gaa cgt acc atc gaa gct atg aag atc ttt gca aag aga tac tca agc<br>Glu Arg Thr Ile Glu Ala Met Lys Ile Phe Ala Lys Arg Tyr Ser Ser<br>465 470 475 480 | | 1440 |
| tat gcc gag att gga aga aaa ctt gga act tgg aat ttc aat gta aaa<br>Tyr Ala Glu Ile Gly Arg Lys Leu Gly Thr Trp Asn Phe Asn Val Lys<br>485 490 495 | | 1488 |
| aca att ctt gag agc gac aca gtg gat aac gtt gaa atc ctt gaa aag<br>Thr Ile Leu Glu Ser Asp Thr Val Asp Asn Val Glu Ile Leu Glu Lys<br>500 505 510 | | 1536 |
| ata agg aaa att gag ctt gag ctc ata gag gaa att ctt tcg gat gga<br>Ile Arg Lys Ile Glu Leu Glu Leu Ile Glu Glu Ile Leu Ser Asp Gly<br>515 520 525 | | 1584 |
| aag ctc aaa gaa ggt ata gca tat ctc att ttc ctc ttc cag aat gag<br>Lys Leu Lys Glu Gly Ile Ala Tyr Leu Ile Phe Leu Phe Gln Asn Glu<br>530 535 540 | | 1632 |
| ctt tac tgg gac gag ata act gaa gta aaa gag ctt agg gga gac ttt<br>Leu Tyr Trp Asp Glu Ile Thr Glu Val Lys Glu Leu Arg Gly Asp Phe<br>545 550 555 560 | | 1680 |
| ata atc tat gat ctt cat gtt cct ggc tac cac aac ttt att gct ggg<br> | | 1728 |

```
                Ile Ile Tyr Asp Leu His Val Pro Gly Tyr His Asn Phe Ile Ala Gly
                                565                 570                 575 aac atg cca aca gta gtc cat aac act aca gcg gct ttg gcc ctt gca              1776
Asn Met Pro Thr Val Val His Asn Thr Thr Ala Ala Leu Ala Leu Ala
                580                 585                 590 aga gag ctt ttc ggc gaa aac tgg agg cat aac ttc ctc gag ttg aat              1824
Arg Glu Leu Phe Gly Glu Asn Trp Arg His Asn Phe Leu Glu Leu Asn
                595                 600                 605 gct tca gat gaa aga ggt ata aac gta att aga gag aaa gtt aag gag              1872
Ala Ser Asp Glu Arg Gly Ile Asn Val Ile Arg Glu Lys Val Lys Glu
        610                 615                 620 ttt gcg aga aca aag cct ata gga gga gca agc ttc aag ata att ttc              1920
Phe Ala Arg Thr Lys Pro Ile Gly Gly Ala Ser Phe Lys Ile Ile Phe
625                 630                 635                 640 ctt gat gag gcc gac gct tta act caa gat gcc caa caa gcc tta aga              1968
Leu Asp Glu Ala Asp Ala Leu Thr Gln Asp Ala Gln Gln Ala Leu Arg
                645                 650                 655 aga acc atg gaa atg ttc tcg agt aac gtt cgc ttt atc ttg agc tgt              2016
Arg Thr Met Glu Met Phe Ser Ser Asn Val Arg Phe Ile Leu Ser Cys
                660                 665                 670 aac tac tcc tcc aag ata att gaa ccc ata cag tct aga tgt gca ata              2064
Asn Tyr Ser Ser Lys Ile Ile Glu Pro Ile Gln Ser Arg Cys Ala Ile
                675                 680                 685 ttc cgc ttc aga cct ctc cgc gat gag gat ata gcg aag aga cta agg              2112
Phe Arg Phe Arg Pro Leu Arg Asp Glu Asp Ile Ala Lys Arg Leu Arg
        690                 695                 700 tac att gcc gaa aat gag ggc tta gag cta act gaa gaa ggt ctc caa              2160
Tyr Ile Ala Glu Asn Glu Gly Leu Glu Leu Thr Glu Glu Gly Leu Gln
705                 710                 715                 720 gca ata ctt tac ata gca gaa gga gat atg aga aga gca ata aac att              2208
Ala Ile Leu Tyr Ile Ala Glu Gly Asp Met Arg Arg Ala Ile Asn Ile
                725                 730                 735 ctg caa gct gca gca gct cta gac aag aag atc acc gac gaa aac gta              2256
Leu Gln Ala Ala Ala Ala Leu Asp Lys Lys Ile Thr Asp Glu Asn Val
                740                 745                 750 ttc atg gta gcg agt aga gct aga cct gaa gat ata aga gag atg atg              2304
Phe Met Val Ala Ser Arg Ala Arg Pro Glu Asp Ile Arg Glu Met Met
                755                 760                 765 ctt ctt gct ctc aaa ggc aac ttc ttg aag gcc aga gaa aag ctt agg              2352
Leu Leu Ala Leu Lys Gly Asn Phe Leu Lys Ala Arg Glu Lys Leu Arg
        770                 775                 780 gag ata ctt ctc aag caa gga ctt agt gga gaa gat gta cta gtt cag              2400
Glu Ile Leu Leu Lys Gln Gly Leu Ser Gly Glu Asp Val Leu Val Gln
785                 790                 795                 800 atg cac aaa gaa gtc ttc aac ctg cca ata gag gag cca aag aag gtt              2448
Met His Lys Glu Val Phe Asn Leu Pro Ile Glu Glu Pro Lys Lys Val
                805                 810                 815 ctg ctt gct gat aag ata gga gag tat aac ttc aga ctc gtt gaa ggg              2496
Leu Leu Ala Asp Lys Ile Gly Glu Tyr Asn Phe Arg Leu Val Glu Gly
                820                 825                 830 gct aat gaa ata att cag ctt gaa gca ctc tta gca cag ttc acc cta              2544
Ala Asn Glu Ile Ile Gln Leu Glu Ala Leu Leu Ala Gln Phe Thr Leu
                835                 840                 845 att ggg aag aag tga                                                          2559
Ile Gly Lys Lys
        850

<210> SEQ ID NO 18
<211> LENGTH: 852
<212> TYPE: PRT
<213> ORGANISM: Pyrococcus furiosus
```

<400> SEQUENCE: 18

```
Met Ser Glu Glu Ile Arg Glu Val Lys Val Leu Glu Lys Pro Trp Val
1               5                   10                  15
Glu Lys Tyr Arg Pro Gln Arg Leu Asp Asp Ile Val Gly Gln Glu His
            20                  25                  30
Ile Val Lys Arg Leu Lys His Tyr Val Lys Thr Gly Ser Met Pro His
        35                  40                  45
Leu Leu Phe Ala Gly Pro Pro Gly Val Gly Lys Cys Leu Thr Gly Asp
    50                  55                  60
Thr Lys Val Ile Ala Asn Gly Gln Leu Phe Glu Leu Gly Glu Leu Val
65                  70                  75                  80
Glu Lys Leu Ser Gly Gly Arg Phe Gly Pro Thr Pro Val Lys Gly Leu
                85                  90                  95
Lys Val Leu Gly Ile Asp Glu Asp Gly Lys Leu Arg Glu Phe Glu Val
            100                 105                 110
Gln Tyr Val Tyr Lys Asp Arg Thr Asp Arg Leu Ile Lys Ile Lys Thr
        115                 120                 125
Gln Leu Gly Arg Glu Leu Lys Val Thr Pro Tyr His Pro Leu Leu Val
    130                 135                 140
Asn Arg Glu Asn Gly Glu Ile Lys Trp Ile Lys Ala Glu Glu Leu Lys
145                 150                 155                 160
Pro Gly Asp Lys Leu Ala Ile Pro Ser Phe Leu Pro Leu Ile Thr Gly
                165                 170                 175
Glu Asn Pro Leu Ala Glu Trp Leu Gly Tyr Phe Met Gly Ser Gly Tyr
            180                 185                 190
Ala Tyr Pro Ser Asn Ser Val Ile Thr Phe Thr Asn Glu Asp Pro Leu
        195                 200                 205
Ile Arg Gln Arg Phe Met Glu Leu Thr Glu Lys Leu Phe Pro Asp Ala
    210                 215                 220
Lys Ile Arg Glu Arg Ile His Ala Asp Gly Thr Pro Glu Val Tyr Val
225                 230                 235                 240
Val Ser Arg Lys Ala Trp Ser Leu Val Asn Ser Ile Ser Leu Thr Leu
                245                 250                 255
Ile Pro Arg Glu Gly Trp Lys Gly Ile Arg Ser Phe Leu Arg Ala Tyr
            260                 265                 270
Ser Asp Cys Asn Gly Arg Ile Glu Ser Asp Ala Ile Val Leu Ser Thr
        275                 280                 285
Asp Asn Asn Asp Met Ala Gln Gln Ile Ala Tyr Ala Leu Ala Ser Phe
    290                 295                 300
Gly Ile Ile Ala Lys Met Asp Gly Glu Asp Val Ile Ile Ser Gly Ser
305                 310                 315                 320
Asp Asn Ile Glu Arg Phe Leu Asn Glu Ile Gly Phe Ser Thr Gln Ser
                325                 330                 335
Lys Leu Lys Glu Ala Gln Lys Leu Ile Arg Lys Thr Asn Val Arg Ser
            340                 345                 350
Asp Gly Leu Lys Ile Asn Tyr Glu Leu Ile Ser Tyr Val Lys Asp Arg
        355                 360                 365
Leu Arg Leu Asn Val Asn Asp Lys Arg Asn Leu Ser Tyr Arg Asn Ala
    370                 375                 380
Lys Glu Leu Ser Trp Glu Leu Met Lys Glu Ile Tyr Tyr Arg Leu Glu
385                 390                 395                 400
Glu Leu Glu Arg Leu Lys Lys Val Leu Ser Glu Pro Ile Leu Ile Asp
                405                 410                 415
```

-continued

Trp Asn Glu Val Ala Lys Lys Ser Asp Glu Val Ile Glu Lys Ala Lys
            420                 425                 430

Ile Arg Ala Glu Lys Leu Leu Glu Tyr Ile Lys Gly Glu Arg Lys Pro
        435                 440                 445

Ser Phe Lys Glu Tyr Ile Glu Ile Ala Lys Val Leu Gly Ile Asn Val
450                 455                 460

Glu Arg Thr Ile Glu Ala Met Lys Ile Phe Ala Lys Arg Tyr Ser Ser
465                 470                 475                 480

Tyr Ala Glu Ile Gly Arg Lys Leu Gly Thr Trp Asn Phe Asn Val Lys
                485                 490                 495

Thr Ile Leu Glu Ser Asp Thr Val Asp Asn Val Glu Ile Leu Glu Lys
            500                 505                 510

Ile Arg Lys Ile Glu Leu Glu Leu Ile Glu Glu Ile Leu Ser Asp Gly
        515                 520                 525

Lys Leu Lys Glu Gly Ile Ala Tyr Leu Ile Phe Leu Phe Gln Asn Glu
530                 535                 540

Leu Tyr Trp Asp Glu Ile Thr Glu Val Lys Glu Leu Arg Gly Asp Phe
545                 550                 555                 560

Ile Ile Tyr Asp Leu His Val Pro Gly Tyr His Asn Phe Ile Ala Gly
                565                 570                 575

Asn Met Pro Thr Val Val His Asn Thr Thr Ala Ala Leu Ala Leu Ala
            580                 585                 590

Arg Glu Leu Phe Gly Glu Asn Trp Arg His Asn Phe Leu Glu Leu Asn
        595                 600                 605

Ala Ser Asp Glu Arg Gly Ile Asn Val Ile Arg Glu Lys Val Lys Glu
610                 615                 620

Phe Ala Arg Thr Lys Pro Ile Gly Gly Ala Ser Phe Lys Ile Ile Phe
625                 630                 635                 640

Leu Asp Glu Ala Asp Ala Leu Thr Gln Asp Ala Gln Gln Ala Leu Arg
                645                 650                 655

Arg Thr Met Glu Met Phe Ser Ser Asn Val Arg Phe Ile Leu Ser Cys
            660                 665                 670

Asn Tyr Ser Ser Lys Ile Ile Glu Pro Ile Gln Ser Arg Cys Ala Ile
        675                 680                 685

Phe Arg Phe Arg Pro Leu Arg Asp Glu Asp Ile Ala Lys Arg Leu Arg
690                 695                 700

Tyr Ile Ala Glu Asn Glu Gly Leu Glu Leu Thr Glu Glu Gly Leu Gln
705                 710                 715                 720

Ala Ile Leu Tyr Ile Ala Glu Gly Asp Met Arg Arg Ala Ile Asn Ile
                725                 730                 735

Leu Gln Ala Ala Ala Leu Asp Lys Lys Ile Thr Asp Glu Asn Val
            740                 745                 750

Phe Met Val Ala Ser Arg Ala Arg Pro Glu Asp Ile Arg Glu Met Met
        755                 760                 765

Leu Leu Ala Leu Lys Gly Asn Phe Leu Lys Ala Arg Glu Lys Leu Arg
770                 775                 780

Glu Ile Leu Leu Lys Gln Gly Leu Ser Gly Glu Asp Val Leu Val Gln
785                 790                 795                 800

Met His Lys Glu Val Phe Asn Leu Pro Ile Glu Pro Lys Lys Val
                805                 810                 815

Leu Leu Ala Asp Lys Ile Gly Glu Tyr Asn Phe Arg Leu Val Glu Gly
            820                 825                 830

Ala Asn Glu Ile Ile Gln Leu Glu Ala Leu Leu Ala Gln Phe Thr Leu

Ile Gly Lys Lys
    850

<210> SEQ ID NO 19
<211> LENGTH: 24
<212> TYPE: DNA
<213> ORGANISM: Artificial
<220> FEATURE:
<223> OTHER INFORMATION: primer: RFCS-F primer

<400> SEQUENCE: 19
atgagcgaag agattagaga agtt                                           24

<210> SEQ ID NO 20
<211> LENGTH: 26
<212> TYPE: DNA
<213> ORGANISM: Artificial
<220> FEATURE:
<223> OTHER INFORMATION: primer: RFCS-R primer

<400> SEQUENCE: 20
atcacttctt cccaattagg gtgaac                                         26

<210> SEQ ID NO 21
<211> LENGTH: 31
<212> TYPE: DNA
<213> ORGANISM: Artificial
<220> FEATURE:
<223> OTHER INFORMATION: primer: RFCSF1 primer

<400> SEQUENCE: 21
tcatatgagc gaagagatta gagaagttaa g                                   31

<210> SEQ ID NO 22
<211> LENGTH: 46
<212> TYPE: DNA
<213> ORGANISM: Artificial
<220> FEATURE:
<223> OTHER INFORMATION: primer: RFCSF2 primer

<400> SEQUENCE: 22
gcaggccccc ctggtgtcgg aaagactaca gcggctttgg cccttg                   46

<210> SEQ ID NO 23
<211> LENGTH: 45
<212> TYPE: DNA
<213> ORGANISM: Artificial
<220> FEATURE:
<223> OTHER INFORMATION: primer: RFCSR2 primer

<400> SEQUENCE: 23
caagggccaa agccgctgta gtctttccga caccaggggg gcctg                    45

<210> SEQ ID NO 24
<211> LENGTH: 35
<212> TYPE: DNA
<213> ORGANISM: Artificial
<220> FEATURE:
<223> OTHER INFORMATION: primer: RFCSR1 primer

<400> SEQUENCE: 24
aggtcgacca tcacttcttc ccaattaggg tgaac                               35

<210> SEQ ID NO 25
<211> LENGTH: 20

```
<212> TYPE: DNA
<213> ORGANISM: Artificial
<220> FEATURE:
<223> OTHER INFORMATION: primer: F02

<400> SEQUENCE: 25
gtcgtttctg caagcttggc                                              20

<210> SEQ ID NO 26
<211> LENGTH: 21
<212> TYPE: DNA
<213> ORGANISM: Artificial
<220> FEATURE:
<223> OTHER INFORMATION: primer: F11

<400> SEQUENCE: 26
gctgctgaaa cgttgcggtt g                                            21

<210> SEQ ID NO 27
<211> LENGTH: 22
<212> TYPE: DNA
<213> ORGANISM: Artificial
<220> FEATURE:
<223> OTHER INFORMATION: primer: F24

<400> SEQUENCE: 27
cgtcggggac attgtaaagg cg                                           22

<210> SEQ ID NO 28
<211> LENGTH: 21
<212> TYPE: DNA
<213> ORGANISM: Artificial
<220> FEATURE:
<223> OTHER INFORMATION: primer: R03

<400> SEQUENCE: 28
ccgagataaa acaaacccg c                                             21

<210> SEQ ID NO 29
<211> LENGTH: 21
<212> TYPE: DNA
<213> ORGANISM: Artificial
<220> FEATURE:
<223> OTHER INFORMATION: primer: R14

<400> SEQUENCE: 29
ggcattccta cgagcagatg g                                            21

<210> SEQ ID NO 30
<211> LENGTH: 20
<212> TYPE: DNA
<213> ORGANISM: Artificial
<220> FEATURE:
<223> OTHER INFORMATION: primer: R16

<400> SEQUENCE: 30
tcccgttctt ccctggtagc                                              20

<210> SEQ ID NO 31
<211> LENGTH: 750
<212> TYPE: DNA
<213> ORGANISM: Thermococcus kodakaraensis

<400> SEQUENCE: 31
atgccgttcg aagttgtttt tgacggggcc aaggagtttg cagacctgat agcgaccgca      60
agcaacctca tcgacgaggc cgcctttaag ttcactgagg aaggcataag catgcgcgca     120
```

```
atggacccga gcagggtcgt tctcattgac ctcaacctgc ccgaaagcat cttctccaag      180
tacgaggtcg aagagcccga acaatcggc atcaacatgg accagttcaa gaaaatcctc      240
aagcgcggca aggcgaaaga caccctcata ctcaggaagg gcgacgagaa cttccttgag      300 ataactttg agggaaccgc caagaggaca ttcaggctcc ctctgataga gtgtggaagag      360 cttgagctgg agcttcccga gctcccgttc acggctaagg tagtcctcct cggtgaggtt      420
ctcaaggagg gcataaagga cgcttccctc gtcagcgacg ccatcaagtt catagcaaag      480
gagaacgagt tcacaatgaa ggccgagggc gagaccaacg aggtcgagat aaggcttacc      540
cttgaggacg agggccttct cgaccttgaa gtcgaggaag agaccaagag tgcctacggc      600
ataagctacc tcagcgacat ggtcaagggc atcgggaagg ccgacgaagt tatcctccgc      660
ttcggcaacg agatgccgct ccagatggag tacatgatca gagacgaggg cagactgacc      720
ttcctgctcg ctccgcgcgt tgaggagtga                                      750

<210> SEQ ID NO 32
<211> LENGTH: 249
<212> TYPE: PRT
<213> ORGANISM: Thermococcus kodakaraensis

<400> SEQUENCE: 32

Met Pro Phe Glu Val Val Phe Asp Gly Ala Lys Glu Phe Ala Asp Leu
1               5                   10                  15

Ile Ala Thr Ala Ser Asn Leu Ile Asp Glu Ala Ala Phe Lys Phe Thr
            20                  25                  30

Glu Glu Gly Ile Ser Met Arg Ala Met Asp Pro Ser Arg Val Val Leu
        35                  40                  45

Ile Asp Leu Asn Leu Pro Glu Ser Ile Phe Ser Lys Tyr Glu Val Glu
    50                  55                  60

Glu Pro Glu Thr Ile Gly Ile Asn Met Asp Gln Phe Lys Lys Ile Leu
65                  70                  75                  80

Lys Arg Gly Lys Ala Lys Asp Thr Leu Ile Leu Arg Lys Gly Asp Glu
                85                  90                  95

Asn Phe Leu Glu Ile Thr Phe Glu Gly Thr Ala Lys Arg Thr Phe Arg
            100                 105                 110

Leu Pro Leu Ile Asp Val Glu Glu Leu Glu Leu Glu Leu Pro Glu Leu
        115                 120                 125

Pro Phe Thr Ala Lys Val Val Leu Leu Gly Glu Val Leu Lys Glu Gly
    130                 135                 140

Ile Lys Asp Ala Ser Leu Val Ser Asp Ala Ile Lys Phe Ile Ala Lys
145                 150                 155                 160

Glu Asn Glu Phe Thr Met Lys Ala Glu Gly Glu Thr Asn Glu Val Glu
                165                 170                 175

Ile Arg Leu Thr Leu Glu Asp Glu Gly Leu Leu Asp Leu Glu Val Glu
            180                 185                 190

Glu Glu Thr Lys Ser Ala Tyr Gly Ile Ser Tyr Leu Ser Asp Met Val
        195                 200                 205

Lys Gly Ile Gly Lys Ala Asp Glu Val Ile Leu Arg Phe Gly Asn Glu
    210                 215                 220

Met Pro Leu Gln Met Glu Tyr Met Ile Arg Asp Glu Gly Arg Leu Thr
225                 230                 235                 240

Phe Leu Leu Ala Pro Arg Val Glu Glu
                245
```

```
<210> SEQ ID NO 33
<211> LENGTH: 27
<212> TYPE: DNA
<213> ORGANISM: artificial sequence
<220> FEATURE:
<223> OTHER INFORMATION: KOD-PCNA-F primer

<400> SEQUENCE: 33
ccatatgccg ttcgaagttg tttttga                                        27

<210> SEQ ID NO 34
<211> LENGTH: 24
<212> TYPE: DNA
<213> ORGANISM: artificial sequence
<220> FEATURE:
<223> OTHER INFORMATION: KOD-PCNA-R primer

<400> SEQUENCE: 34
ctcgagtcac tcctcaacgc gcgg                                           24

<210> SEQ ID NO 35
<211> LENGTH: 34
<212> TYPE: DNA
<213> ORGANISM: artificial sequence
<220> FEATURE:
<223> OTHER INFORMATION: KOD_M73L-F primer

<400> SEQUENCE: 35
cgagacaatc ggcatcaacc tggaccagtt caag                                34

<210> SEQ ID NO 36
<211> LENGTH: 34
<212> TYPE: DNA
<213> ORGANISM: artificial sequence
<220> FEATURE:
<223> OTHER INFORMATION: KOD_M73L-R primer

<400> SEQUENCE: 36
cttgaactgg tccaggttga tgccgattgt ctcg                                34

<210> SEQ ID NO 37
<211> LENGTH: 38
<212> TYPE: DNA
<213> ORGANISM: artificial sequence
<220> FEATURE:
<223> OTHER INFORMATION: KOD_E143R-F primer

<400> SEQUENCE: 37
ctcggtgagg ttctcaagcg tggcataaag gacgcttc                            38

<210> SEQ ID NO 38
<211> LENGTH: 38
<212> TYPE: DNA
<213> ORGANISM: artificial sequence
<220> FEATURE:
<223> OTHER INFORMATION: KOD_E143R-R primer

<400> SEQUENCE: 38
gaagcgtcct ttatgccacg cttgagaacc tcaccgag                            38

<210> SEQ ID NO 39
<211> LENGTH: 1500
<212> TYPE: DNA
<213> ORGANISM: Thermococcus kodakaraensis

<400> SEQUENCE: 39
atgacggaag tcccatgggt tgaaaaatac agacctagga agctcagcga gatagtaaac    60
```

-continued

```
caggagaaag cgttagagca ggttagggcg tgggtcgaag cctggctcca cggaaatccg    120
ccgaagaaga aggccctcct tctagcaggc cccctggag tcggcaaaac gaccaccgtc     180
tatgccctgg ccaacgagta cggcttcgag gtcatcgagc tcaacgcaag cgacgagagg    240
acgtatgaaa agatagagcg ctacgttcaa gctgcataca ctatggatat tctcggaaag    300
aggaggaagc tgatattcct tgacgaggct gacaacatcg agccctctgg ggcgagggag    360
atagcgaagc tcatcgacaa ggccagaaac ccgataataa tgagcgccaa ccactactgg    420
gaggttccca gggagatacg caacaaagcc cagatagtcg agtacaagag gttgacgcag    480
agggacatca taaaggccct cgtgagaatc ctcaagcgtg agggactcga agttcccaag    540
gaggttctct acgagatagc gaagagggct aacggcgacc tgaggcagc tgtaaacgat     600 cttcagaccg ttgttaccgg tggagtcgag gatgccgttg aagtcctggc ttaccgcgac    660
actgagaaga gcgttttcca ggcgcttgcc cagctgttcg caacggacaa cgccaagagg    720
gcaaagttag ctgttcttgg agttgacatg atgcctaacg agcttctcca gtggatagac    780
gagaacgtcc cgtatgtcta ctacaggcct gaagacatag cgagggccta cgaggcgctc    840
agcagggctg acatatacct cggtagggca cagaggactg gaaactacgg cctctggaag    900
tacgcgaccg acatgatgac ggctggggtg gcggtcgctg gcatcaagaa gaagggcttc    960
gttaagatct acccacctaa gacgataaag ctcctcaccg agagcaagga ggagcgttcg   1020
ctcagggact cagtaatcaa gaagataatg agcgagatgc acatggctaa gcttgaggcc   1080
atagagaccc tccgctacct tagagttatc ttcgagaaca accccgattt ggcggcccac   1140
tttgtcgttt tcctcgacct cagcgagaag gaagttgagt tcataactgg agacaaggag   1200
aaggcgaaga cgtatgggc aaagagcatg aacattgaga gaaactcaa aaagaaggc     1260 gagcttgagg cgagagcaaa ggaagccgaa agaagggtgg aagcggctga ggaagaggaa   1320
actatggaag ctggggaacc tgaagaagaa cttgaagaag tcgaggagga agagttaacc   1380
gaggaggagc ttgaggaagc ggaggaagag atagagaccg ttgggaagaa ggagaagccc   1440
gagaaggaga aaaccaagaa gggcaagcag gcgacgctgt tcgacttcct caagaagtga   1500
```

```
<210> SEQ ID NO 40
<211> LENGTH: 26
<212> TYPE: DNA
<213> ORGANISM: artificial sequence
<220> FEATURE:
<223> OTHER INFORMATION: KOD-RFCL-F primer

<400> SEQUENCE: 40
ccatatgacg gaagtcccat gggttg                                          26

<210> SEQ ID NO 41
<211> LENGTH: 30
<212> TYPE: DNA
<213> ORGANISM: artificial sequence
<220> FEATURE:
<223> OTHER INFORMATION: KOD-RFCL-R primer

<400> SEQUENCE: 41
ctcgagtcac ttcttgagga agtcgaacag                                      30

<210> SEQ ID NO 42
<211> LENGTH: 981
<212> TYPE: DNA
<213> ORGANISM: Thermococcus kodakaraensis

<400> SEQUENCE: 42
```

```
atgtccgagg aagtgaagga agttaaaatt ctcgaaaagc cgtgggtcga agaagtacaga      60 ccccagaggc tcgaggacat agtaggtcag gatcacatag tcaagaggct gaagcactac     120
gttaaaaccg gctcgatgcc gcaccttcta ttcgcagggc cacccggcgt cgggaagaca     180
accgctgcac tggctttagc tagagaactc ttcggtgaga actggaggca aacttccta     240 gagctgaacg cgagcgatga gagggggtata aacgtcatcc gtgaaaaggt aaaggagttc    300
gcgaggacga agccgatagg cggtgcgagc tttaagataa tcttccttga tgaggcagat    360
gccctcacac aggacgctca gcaggccctc agaaggacga tggagatgtt ctcgaacaac    420
gtccgcttta tcctgagctg taactactcc tcaaagatca tcgaacccat acagtcgagg    480
tgtgccatct tccgcttcag accgctccgc gatgaggaca tagcgaagcg catcaggtac    540
atagccgaaa atgagggtct cgagctcacc gaggaaggcc tgcaggcgat actctacgtc    600
gctgagggcg atctcaggag ggcaatcaac gtccttcagg cggcagcagc cctcgacacg    660
aagataaccg acgagaacgt cttcctcgtg gccagcaggg cgaggcctga agacgtacgt    720
gaaatgatga cccttgctct ggaaggcaac ttcctgaagg ccagagagaa gctgagggat    780
atcctgttaa ggcagggcct cagcggtgaa gatgtcctca tccagatgca caaggaggtc    840
ttcaacctcc cgattcccga ggacaagaag gtggccctgg cggacaagat aggagagtac    900
aacttccgcc tggttgaagg ggctaacgag atgatacagc tcgaggcact ccttgcccag    960
ttcacgatta tgggtaagtg a                                              981

<210> SEQ ID NO 43
<211> LENGTH: 22
<212> TYPE: DNA
<213> ORGANISM: artificial sequence
<220> FEATURE:
<223> OTHER INFORMATION: KOD-RFCS-F primer

<400> SEQUENCE: 43
atgtccgagg aagtgaagga ag                                              22

<210> SEQ ID NO 44
<211> LENGTH: 24
<212> TYPE: DNA
<213> ORGANISM: artificial sequence
<220> FEATURE:
<223> OTHER INFORMATION: KOD-RFCS-R primer

<400> SEQUENCE: 44
tcacttaccc ataatcgtga actg                                            24

<210> SEQ ID NO 45
<211> LENGTH: 26
<212> TYPE: DNA
<213> ORGANISM: artificial sequence
<220> FEATURE:
<223> OTHER INFORMATION: RFCS-Nde-F primer

<400> SEQUENCE: 45
ccatatgtcc gaggaagtga aggaag                                          26

<210> SEQ ID NO 46
<211> LENGTH: 30
<212> TYPE: DNA
<213> ORGANISM: artificial sequence
<220> FEATURE:
<223> OTHER INFORMATION: RFCS-Sal-R primer

<400> SEQUENCE: 46
```
gtcgactcac ttacccataa tcgtgaactg                                    30

<210> SEQ ID NO 47
<211> LENGTH: 32
<212> TYPE: DNA
<213> ORGANISM: artificial sequence
<220> FEATURE:
<223> OTHER INFORMATION: RFCS-Ex2-F

<400> SEQUENCE: 47
cgtcgggaag acaaccgctg cactggcttt ag                                 32

<210> SEQ ID NO 48
<211> LENGTH: 29
<212> TYPE: DNA
<213> ORGANISM: artificial sequence
<220> FEATURE:
<223> OTHER INFORMATION: RFCS-Ex1-R primer

<400> SEQUENCE: 48
cagcggttgt cttcccgacg ccgggtggc                                     29

<210> SEQ ID NO 49
<211> LENGTH: 19
<212> TYPE: DNA
<213> ORGANISM: Artificial
<220> FEATURE:
<223> OTHER INFORMATION: primer F09

<400> SEQUENCE: 49
agcctttgcc tcgctatac                                                19

<210> SEQ ID NO 50
<211> LENGTH: 21
<212> TYPE: DNA
<213> ORGANISM: Artificial
<220> FEATURE:
<223> OTHER INFORMATION: primer F14

<400> SEQUENCE: 50
ccatctgctc gtaggaatgc c                                             21

<210> SEQ ID NO 51
<211> LENGTH: 20
<212> TYPE: DNA
<213> ORGANISM: Artificial
<220> FEATURE:
<223> OTHER INFORMATION: primer F16

<400> SEQUENCE: 51
gctaccaggg aagaacggga                                               20

<210> SEQ ID NO 52
<211> LENGTH: 22
<212> TYPE: DNA
<213> ORGANISM: Artificial
<220> FEATURE:
<223> OTHER INFORMATION: primer F19

<400> SEQUENCE: 52
ccaagatagc actcgaacga cg                                            22

<210> SEQ ID NO 53
<211> LENGTH: 22
<212> TYPE: DNA
<213> ORGANISM: Artificial

```
<220> FEATURE:
<223> OTHER INFORMATION: primer F23

<400> SEQUENCE: 53
cgaatcccat ctcggcaagg ag                                              22

<210> SEQ ID NO 54
<211> LENGTH: 22
<212> TYPE: DNA
<213> ORGANISM: Artificial
<220> FEATURE:
<223> OTHER INFORMATION: primer F25

<400> SEQUENCE: 54
gcacttgcgg tgacagtcac tc                                              22

<210> SEQ ID NO 55
<211> LENGTH: 21
<212> TYPE: DNA
<213> ORGANISM: Artificial
<220> FEATURE:
<223> OTHER INFORMATION: primer R04

<400> SEQUENCE: 55
ccagtgcaaa gctttgtgtg c                                               21

<210> SEQ ID NO 56
<211> LENGTH: 21
<212> TYPE: DNA
<213> ORGANISM: Artificial
<220> FEATURE:
<223> OTHER INFORMATION: primer R11

<400> SEQUENCE: 56
caaccgcaac gtttcagcag c                                               21

<210> SEQ ID NO 57
<211> LENGTH: 20
<212> TYPE: DNA
<213> ORGANISM: Artificial
<220> FEATURE:
<223> OTHER INFORMATION: primer R15

<400> SEQUENCE: 57
cccagtagta ctgcaagagg                                                 20

<210> SEQ ID NO 58
<211> LENGTH: 19
<212> TYPE: DNA
<213> ORGANISM: Artificial
<220> FEATURE:
<223> OTHER INFORMATION: primer R17

<400> SEQUENCE: 58
cgtggtgtaa ttccctcgc                                                  19

<210> SEQ ID NO 59
<211> LENGTH: 24
<212> TYPE: DNA
<213> ORGANISM: Artificial
<220> FEATURE:
<223> OTHER INFORMATION: primer R21

<400> SEQUENCE: 59
gctcaccagt tcgatgatta acgg                                            24
```

```
<210> SEQ ID NO 60
<211> LENGTH: 22
<212> TYPE: DNA
<213> ORGANISM: Artificial
<220> FEATURE:
<223> OTHER INFORMATION: primer R25

<400> SEQUENCE: 60
gagtgactgt caccgcaagt gc                                              22

<210> SEQ ID NO 61
<211> LENGTH: 22
<212> TYPE: DNA
<213> ORGANISM: Artificial
<220> FEATURE:
<223> OTHER INFORMATION: primer R27

<400> SEQUENCE: 61
gcatcgccgg ctgatttctt cg                                              22

<210> SEQ ID NO 62
<211> LENGTH: 30
<212> TYPE: DNA
<213> ORGANISM: Artificial
<220> FEATURE:
<223> OTHER INFORMATION: primer: Pfu_D143K-F

<400> SEQUENCE: 62
ggagaagtcc taaaacatgc tgttaaagat                                      30

<210> SEQ ID NO 63
<211> LENGTH: 30
<212> TYPE: DNA
<213> ORGANISM: Artificial
<220> FEATURE:
<223> OTHER INFORMATION: primer: Pfu_D143K-R

<400> SEQUENCE: 63
atctttaaca gcttttttta ggacttctcc                                      30

<210> SEQ ID NO 64
<211> LENGTH: 30
<212> TYPE: DNA
<213> ORGANISM: Artificial
<220> FEATURE:
<223> OTHER INFORMATION: primer: Pfu_D143H-F

<400> SEQUENCE: 64
ggagaagtcc taaaacatgc tgttaaagat                                      30

<210> SEQ ID NO 65
<211> LENGTH: 30
<212> TYPE: DNA
<213> ORGANISM: Artificial
<220> FEATURE:
<223> OTHER INFORMATION: primer: Pfu_D143H-R

<400> SEQUENCE: 65
atctttaaca gcatgtttta ggacttctcc                                      30

<210> SEQ ID NO 66
<211> LENGTH: 34
<212> TYPE: DNA
<213> ORGANISM: Artificial
<220> FEATURE:
<223> OTHER INFORMATION: primer: Pfu_R109E-F

<400> SEQUENCE: 66
```
caaggaactg caacagaaac atttagagtt cccc 34

<210> SEQ ID NO 67
<211> LENGTH: 34
<212> TYPE: DNA
<213> ORGANISM: Artificial
<220> FEATURE:
<223> OTHER INFORMATION: primer: Pfu_R109E-R

<400> SEQUENCE: 67
ggggaactct aaatgtttct gttgcagttc cttg 34

<210> SEQ ID NO 68
<211> LENGTH: 40
<212> TYPE: DNA
<213> ORGANISM: Artificial
<220> FEATURE:
<223> OTHER INFORMATION: primer: Pfu_D147R-F

<400> SEQUENCE: 68
cctaaaagat gctgttaaaa gagcctctct agtgagtgac 40

<210> SEQ ID NO 69
<211> LENGTH: 40
<212> TYPE: DNA
<213> ORGANISM: Artificial
<220> FEATURE:
<223> OTHER INFORMATION: primer: Pfu_D147R-R

<400> SEQUENCE: 69
gtcactcact agagaggctc ttttaacagc atcttttagg 40

<210> SEQ ID NO 70
<211> LENGTH: 35
<212> TYPE: DNA
<213> ORGANISM: Artificial
<220> FEATURE:
<223> OTHER INFORMATION: primer: Pfu_E139A-F

<400> SEQUENCE: 70
ggttgtagtt cttggagcag tcctaaaaga tgctg 35

<210> SEQ ID NO 71
<211> LENGTH: 35
<212> TYPE: DNA
<213> ORGANISM: Artificial
<220> FEATURE:
<223> OTHER INFORMATION: primer: Pfu_E139A-R

<400> SEQUENCE: 71
cagcatcttt taggactgct ccaagaacta caacc 35

<210> SEQ ID NO 72
<211> LENGTH: 35
<212> TYPE: DNA
<213> ORGANISM: Artificial
<220> FEATURE:
<223> OTHER INFORMATION: primer: Pfu_E139R-F

<400> SEQUENCE: 72
ggttgtagtt cttggaagag tcctaaaaga tgctg 35

<210> SEQ ID NO 73
<211> LENGTH: 35
<212> TYPE: DNA
<213> ORGANISM: Artificial

```
<220> FEATURE:
<223> OTHER INFORMATION: primer: Pfu_E139R-R

<400> SEQUENCE: 73
cagcatcttt taggactctt ccaagaacta caacc                                        35
```